US008846865B2

(12) United States Patent
Briers et al.

(10) Patent No.: US 8,846,865 B2
(45) Date of Patent: Sep. 30, 2014

(54) ENDOLYSIN OBPGPLYS

(75) Inventors: Yves Briers, Rohr AG (CH); Rob Lavigne, Merksem (BE); Maarten Walmagh, Herk-de-Stad (BE); Stefan Miller, Regensburg (DE)

(73) Assignees: Lysando AG, Triesenberg (LI); Katholieke Universiteit Leuven, K.U. Leuven R&D, Leuven (BE)

( * ) Notice: Subject to any disclaimer, the term of this patent is extended or adjusted under 35 U.S.C. 154(b) by 9 days.

(21) Appl. No.: 13/390,033

(22) PCT Filed: Aug. 24, 2010

(86) PCT No.: PCT/EP2010/062351
§ 371 (c)(1),
(2), (4) Date: Apr. 11, 2012

(87) PCT Pub. No.: WO2011/023702
PCT Pub. Date: Mar. 3, 2011

(65) Prior Publication Data
US 2012/0189608 A1  Jul. 26, 2012

(30) Foreign Application Priority Data

Aug. 24, 2009  (EP) .................................... 09168527

(51) Int. Cl.
*A61K 38/43* (2006.01)
*C07K 14/00* (2006.01)
*C12N 9/26* (2006.01)
*A61K 38/00* (2006.01)
*A61K 38/04* (2006.01)
*C12N 9/36* (2006.01)

(52) U.S. Cl.
CPC ............... *C12N 9/2462* (2013.01); *A61K 38/00* (2013.01); *C12Y 302/01017* (2013.01)
USPC ............ 530/350; 435/201; 514/1.1; 514/2.3; 514/2.4; 514/2.8; 424/94.61

(58) Field of Classification Search
None
See application file for complete search history.

(56) References Cited

U.S. PATENT DOCUMENTS

| 7,572,602 B1 * | 8/2009 | Donovan ...................... 435/69.7 |
| 2011/0027249 A1 * | 2/2011 | Donovan ...................... 424/94.3 |
| 2011/0243915 A1 | 10/2011 | Briers et al. ................ 424/94.6 |

FOREIGN PATENT DOCUMENTS

| EP | 0 510 907 | 10/1992 |
| WO | WO 2010/023207 | 3/2010 |
| WO | WO 2010/149792 | 12/2010 |
| WO | WO 2010/149795 | 12/2010 |

OTHER PUBLICATIONS

Sigma Catalog 1997, p. 1089.*
Arima et al., "Bactericidal action of lysozymes attached with various sizes of hydrophobic peptides to the C-terminal using genetic modification," *FEBS Letters*, 415(1):114-118, 1997.
Loessner, "Bacteriophage endolysins—current state of research and applications," *Current Opinion in Microbiology*, 8(4):480-487, 2005.
Orito et al., "*Bacillus amyloliquefaciens* phage endolysin can enhance permeability of *Pseudomonas aeruginosa* outer membrane and induce cell lysis," *Applied Microbiology and Biotechnology*, 6591):105-109, 2004.
PCT International Preliminary Report on Patentability issued in International application No. PCT/EP2010/062351, dated Mar. 8, 2012.
PCT International Search Report and Written Opinion issued in International application No. PCT/EP2010/062351, dated Nov. 11, 2010.

* cited by examiner

*Primary Examiner* — David J Steadman
(74) *Attorney, Agent, or Firm* — Parker Highlander PLLC

(57) ABSTRACT

The present invention relates to a polypeptide with an amino acid sequence according to SEQ ID NO: 1 and fragments or derivatives thereof. The present invention further relates to fusion proteins comprising said polypeptide and an additional peptide stretch fused to said polypeptide at the N- or C-terminus. Moreover, the present invention relates to nucleic acid molecules encoding said polypeptide or fusion protein, vectors comprising said nucleic acid molecules and host cells comprising either said nucleic acid molecules or said vectors. In addition, the present invention relates to said polypeptide or fusion protein for use as a medicament, in particular for the treatment or prevention of Gram-negative bacterial infections, as diagnostic means, as cosmetic substance or as sanitizing agent. The present invention also relates to the use of said polypeptide or fusion protein for the treatment or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to a pharmaceutical composition comprising said polypeptide or fusion protein.

24 Claims, 6 Drawing Sheets

MKNSEKNASIIMSIQRTLASLSLYGGRIDGLFGEKCRGAIILMLNKVYPNFSTNKLPSNTYE
AESVFTFLQTALAGVGLYTITIDGKWGGTSQGAIDALVKSYRQITEAERAGSTLPLGLATVM
SKHMSIEQLRAMLPTDRQGYAEVYIDPLNETMDIFEINTPLRIAHFMAQILHETACFKYTEE
LASGKAYEGRADLGNTRPGDGPLFKGRGLLQITGRLNYVKCQVYLREKLKDPTFDITSSVTC
AQQLSESPLLAALASGYFWRFIKPKLNETADKDDIYWVSVYVNGYAKQANPYYPNRDKEPNH
MKERVQMLAVTKKALGIV (B)

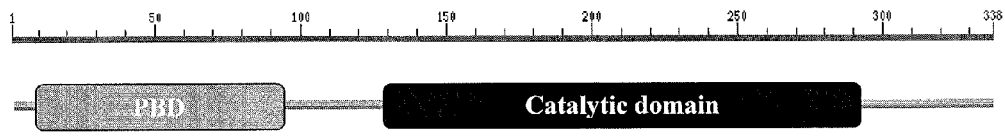

Figure 2

ATGAAAAATAGCGAGAAGAATGCATCGATAATTATGTCGATACAGAGAACGCTCGCTTCACT
CTCACTCTATGGAGGCCGCATCGACGGCCTCTTTGGAGAGAAGTGTCGTGGGGCTATCATCT
TGATGCTGAATAAGGTCTATCCTAATTTCAGCACCAACAAACTTCCGAGTAACACATATGAA
GCGGAATCCGTGTTCACGTTTCTCCAGACTGCTTTGGCTGGTGTTGGTCTTTATACCATTAC
TATTGATGGTAAATGGGGTGGTACTTCTCAAGGTGCTATTGACGCCCTCGTCAAGTCTTACC
GTCAAATTACCGAAGCGGAGCGAGCTGGGTCGACGTTGCCATTAGGTCTTGCTACTGTGATG
TCTAAGCATATGTCTATTGAACAGTTGAGAGCAATGCTCCCTACCGATAGACAAGGATATGC
TGAAGTTTATATCGATCCTTTAAATGAGACGATGGATATATTTGAAATAAATACTCCATTAC
GAATTGCTCATTTCATGGCCCAAATCCTCCACGAAACGGCGTGTTTTAAATATACCGAAGAA
CTGGCGAGCGGTAAGGCTTATGAGGGTCGTGCTGATTTAGGTAATACTCGACCAGGTGATGG
ACCACTGTTTAAAGGTCGTGGATTATTACAAATTACCGGGCGACTGAATTATGTGAAATGCC
AAGTGTATTTGAGAGAAGTTAAAGGACCCTACTTTCGACATTACGTCGTCTGTAACTTGT
GCCCAACAGCTCTCCGAAAGTCCACTTCTTGCTGCATTGGCATCGGGCTACTTCTGGAGATT
CATCAAACCTAAACTCAATGAAACGGCTGATAAAGACGATATCTATTGGGTTTCTGTTTATG
TCAATGGTTACGCTAAACAAGCGAATCCTTATTACCCTAACCGGGATAAGGAACCCAACCAT
ATGAAAGAACGTGTCCAAATGCTTGCAGTGACAAAGAAAGCACACGGAATAGTTTAA

Figure 3

```
ATGAAAAATAGCGAGAAGAATGCATCGATAATTATGTCGATACAGAGAACGCTCGCTTCACT
CTCACTCTATGGAGGCCGCATCGACGGCCTCTTTGGAGAGAAGTGTCGTGGGGCTATCATCT
TGATGCTGAATAAGGTCTATCCTAATTTCAGCACCAACAAACTTCCGAGTAACACATATGAA
GCGGAATCCGTGTTCACGTTTCTCCAGACTGCTTTGGCTGGTGTTGGTCTTTATACCATTAC
TATTGATGGTAAATGGGGTGGTACTTCTCAAGGTGCTATTGACGCCCTCGTCAAGTCTTACC
GTCAAATTACCGAAGCGGAGCGAGCTGGGTCGACGTTGCCATTAGGTCTTGCTACTGTGATG
TCTAAGCATATGTCTATTGAACAGTTGAGAGCAATGCTCCCTACCGATAGACAAGGATATGC
TGAAGTTTATATCGATCCTTTAAATGAGACGATGGATATATTTGAAATAAATACTCCATTAC
GAATTGCTCATTTCATGGCCCAAATCCTCCACGAAACGGCGTGTTTTAAATATACCGAAGAA
CTGGCGAGCGGTAAGGCTTATGAGGGTCGTGCTGATTTAGGTAATACTCGACCAGGTGATGG
ACCACTGTTTAAAGGTCGTGGATTATTACAAATTACCGGGCGACTGAATTATGTGAAATGCC
AAGTGTATTTGAGAGAGAAGTTAAAGGACCCTACTTTCGACATTACGTCGTCTGTAACTTGT
GCCCAACAGCTCTCCGAAAGTCCACTTCTTGCTGCATTGGCATCGGGCTACTTCTGGAGATT
CATCAAACCTAAACTCAATGAAACGGCTGATAAAGACGATATCTATTGGGTTTCTGTTTATG
TCAATGGTTACGCTAAACAAGCGAATCCTTATTACCCTAACCGGGATAAGGAACCCAACCAT
ATGAAAGAACGTGTCCAAATGCTTGCAGTGACAAAGAAAGCACTCGGAATAGTT
```

Figure 4

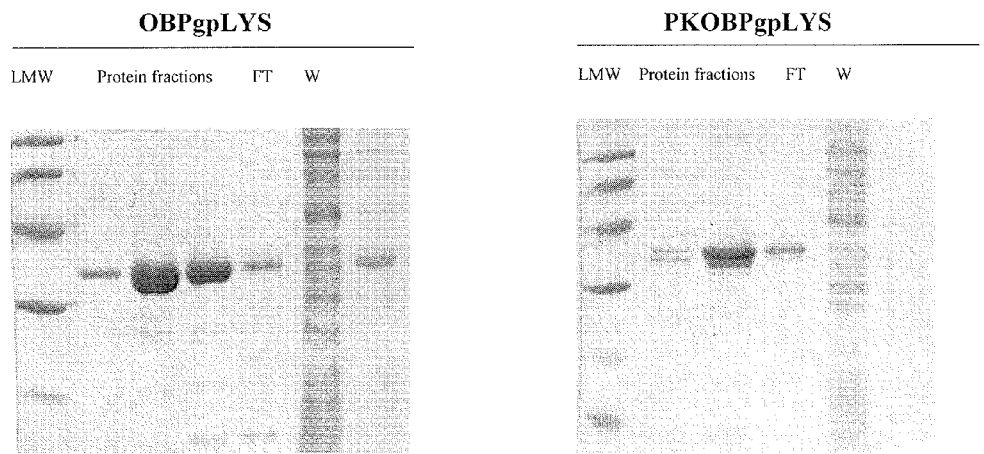

ENDOLYSIN OBPGPLYS

This application is a national phase application under 35 U.S.C. §371 of International Application No. PCT/EP2010/062351 filed 24 Aug. 2010, which claims priority to European Application No. 09 168 527.1 filed on 24 Aug. 2009. The entire text of each of the above-referenced disclosures is specifically incorporated herein by reference without disclaimer.

The present invention relates to a polypeptide with an amino acid sequence according to SEQ ID NO: 1 and fragments or derivatives thereof. The present invention further relates to fusion proteins comprising said polypeptide and an additional peptide stretch fused to said polypeptide at the N- or C-terminus. Moreover, the present invention relates to nucleic acid molecules encoding said polypeptide or fusion protein, vectors comprising said nucleic acid molecules and host cells comprising either said nucleic acid molecules or said vectors. In addition, the present invention relates to said polypeptide or fusion protein for use as a medicament, in particular for the treatment or prevention of Gram-negative bacterial infections, as diagnostic means, as cosmetic substance or as sanitizing agent. The present invention also relates to the use of said polypeptide or fusion protein for the treatment or prevention of Gram-negative bacterial contamination of foodstuff, of food processing equipment, of food processing plants, of surfaces coming into contact with foodstuff, of medical devices, of surfaces in hospitals and surgeries. Furthermore, the present invention relates to a pharmaceutical composition comprising said polypeptide or fusion protein.

Gram-negative bacteria possess an outer membrane, with its characteristic asymmetric bilayer as a hallmark. The outer membrane bilayer consists of an inner monolayer containing phospholipids (primarily phosphatidyl ethanolamine) and an outer monolayer that is mainly composed of a single glycolipid, lipopolysaccharide (LPS). There is an immense diversity of LPS structures in the bacterial kingdom and the LPS structure may be modified in response to prevailing environmental conditions. The stability of the LPS layer and interaction between different LPS molecules is mainly achieved by the electrostatic interaction of divalent ions ($Mg^{2+}$, $Ca^{2+}$) with the anionic components of the LPS molecule (phosphate groups in the lipid A and the inner core and carboxyl groups of KDO). Furthermore, the dense and ordered packing of the hydrophobic moiety of lipid A, favored by the absence of unsaturated fatty acids, forms a rigid structure with high viscosity. This makes it less permeable for lipophilic molecules and confers additional stability to the outer membrane (OM).

Various types of agents having bactericidal or bacteriostatic activity are known, e.g. antibiotics, endolysins, antimicrobial peptides and defensins. Increasingly microbial resistance to antibiotics, however, is creating difficulties in treating more and more infections caused by bacteria. Particular difficulties arise with infections caused by Gram-negative bacteria like *Pseudomonas aeruginosa* and Enterobacteriaceae.

Endolysins are peptidoglycan hydrolases encoded by bacteriophages (or bacterial viruses). They are synthesized during late gene expression in the lytic cycle of phage multiplication and mediate the release of progeny virions from infected cells through degradation of the bacterial peptidoglycan. They are either β(1,4)-glycosylases (lysozymes), transglycosylases, amidases or endopeptidases. Antimicrobial application of endolysins was already suggested in 1991 by Gasson (GB2243611). Although the killing capacity of endolysins has been known for a long time, the use of these enzymes as antibacterials was ignored due to the success and dominance of antibiotics. Only after the appearance of multiple antibiotic resistant bacteria this simple concept of combating human pathogens with endolysins received interest. A compelling need to develop totally new classes of antibacterial agents emerged and endolysins used as 'enzybiotics'—a hybrid term of 'enzymes' and 'antibiotics'—perfectly met this need. In 2001, Fischetti and coworkers demonstrated for the first time the therapeutic potential of bacteriophage Cl endolysin towards group A streptococci (Nelson et al., 2001). Since then many publications have established endolysins as an attractive and complementary alternative to control bacterial infections, particularly by Gram positive bacteria. Subsequently different endolysins against other Gram positive pathogens such as *Streptococcus pneumoniae* (Loeffler et al., 2001), *Bacillus anthracia* (Schuch et al., 2002), *S. agalactiae* (Cheng et al., 2005) and *Staphylococcus aureus* (Rashel et al, 2007) have proven their efficacy as enzybiotics. Nowadays, the most important challenge of endolysin therapy lies in the insensitivity of Gram-negative bacteria towards the exogenous action of endolysins, since the outer membrane shields the access of endolysins from the peptidoglycan. This currently prevents the expansion of the range of effective endolysins to important Gram-negative pathogens.

Antimicrobial peptides (AMPs) represent a wide range of short, cationic or amphipatic, gene encoded peptide antibiotics that can be found in virtually every organism. Different AMPs display different properties, and many peptides in this class are being intensively researched not only as antibiotics, but also as templates for cell penetrating peptides. Despite sharing a few common features (e.g., cationicity, amphipathicity and short size), AMP sequences vary greatly, and at least four structural groups (α-helical, β-sheet, extended and looped) have been proposed to accommodate the diversity of the observed AMP conformations. Likewise, several modes of action as antibiotics have been proposed, and it was shown e.g. that the primary target of many of these peptides is the cell membrane whereas for other peptides the primary target is cytoplasmic invasion and disruption of core metabolic functions. AMPs may become concentrated enough to exhibit cooperative activity despite the absence of specific target binding; for example, by forming a pore in the membrane, as is the case for most AMPs. However, this phenomenon has only been observed in model phospholipid bilayers, and in some cases, AMP concentrations in the membrane that were as high as one peptide molecule per six phospholipid molecules were required for these events to occur. These concentrations are close to, if not at, full membrane saturation. As the minimum inhibitory concentration (MIC) for AMPs are typically in the low micromolar range, scepticism has understandably arisen regarding the relevance of these thresholds and their importance in vivo (Melo et al., Nature reviews, Microbiology, 2009, 245).

Defensins are a large family of small, cationic, cysteine- and arginine-rich antimicrobial peptides, found in both vertebrates and invertebrates. Defensins are divided into five groups according to the spacing pattern of cysteines: plant, invertebrate, α-, β-, and θ-defensins. The latter three are mostly found in mammals. α-defensins are proteins found in neutrophils and intestinal epithelia. β-defensins are the most widely distributed and are secreted by leukocytes and epithelial cells of many kinds. θ-defensins have been rarely found so far e.g. in leukocytes of rhesus macaques. Defensins are active against bacteria, fungi and many enveloped and non-enveloped viruses. However, the concentrations needed for efficient killing of bacteria are mostly high, i.e. in the micromolar range. Activity of many peptides may be limited in presence of physiological salt conditions, divalent cations and serum. Depending on the content of hydrophobic amino acid residues defensins also show haemolytic activity.

Thus, there is a need for new antimicrobial agents against Gram-negative bacteria.

This object is solved by the subject matter defined in the claims.

The following figures serve to illustrate the invention.

BRIEF DESCRIPTION OF THE DRAWINGS

FIG. 1 shows the endolysin OBPgpLYS according to the present invention. In (A) the amino acid sequence of the endolysin OBPgpLYS (SEQ ID NO: 1) according to the present invention is depicted. In (B) the primary structure of the OBPgpLYS comprising an additional His$_6$-tag is given showing the results of a functional analysis using BLASTp and Pfam analysis. The predicted N-terminal peptidoglycan binding domain (PBD, amino acid residues 7-96) is underlined and the C-terminal catalytic domain (amino acid residues 126-292) of the lysozyme-like superfamily is written in italics. The complete amino acid sequence of the OBPgpLYS comprising an additional His$_6$-tag at the C-terminus shown in (B) is depicted in SEQ ID NO: 47.

FIG. 2 shows the nucleotide sequence (SEQ ID NO: 101) of the endolysin of phage OBP.

FIG. 3 shows the nucleotide sequence (SEQ ID NO: 3) of the endolysin OBPgpLYS (SEQ ID NO: 1) according to the present invention.

FIG. 4 shows a picture of a Coomassie-stained SDS-PAGE showing the results of the expression and purification of the unmodified endolysin OBPgpLYS (SEQ ID NO: 47) and its modified endolysin variant PKOBPgpLYS (SEQ ID NO: 49). The lane LMW pertains to a size marker (LMW ladder). The following three lanes pertain to protein fractions of the purified protein in Elution Buffer (20 mM NaH$_2$PO$_4$-NaOH pH7.4; 0.5 M NaCl; 500 mM imidazole) after Ni$^{2+}$ affinity chromatography. The lane FT pertains to the flow through and the lane W to waste fractions. Only minor secondary bands are visible in the purified protein fractions, indicating the high purity of the recombinant protein (>90%).

FIGS. 5A to F show in a graphic representation the antibacterial activities of different compositions of unmodified OBPgpLYS (SEQ ID NO: 47) and the modified PKOBPgpLYS (SEQ ID NO: 49) on several exponential growing Gram-negative bacteria after an incubation at room temperature and without shaking. Each species of Gram-negative bacteria was incubated for 30 minutes with a composition comprising 0.5 mM EDTA but no endolysin, with a composition comprising 1.315 µM unmodified OBPgpLYS but no EDTA, with a composition comprising 1.315 µM modified PKOBPgpLYS but no EDTA, with a composition comprising 1.315 µM unmodified OBPgpLYS and 0.5 mM EDTA and with a composition comprising 1.315 µM modified PKOBPgpLYS and 0.5 mM EDTA.

Figure 5:
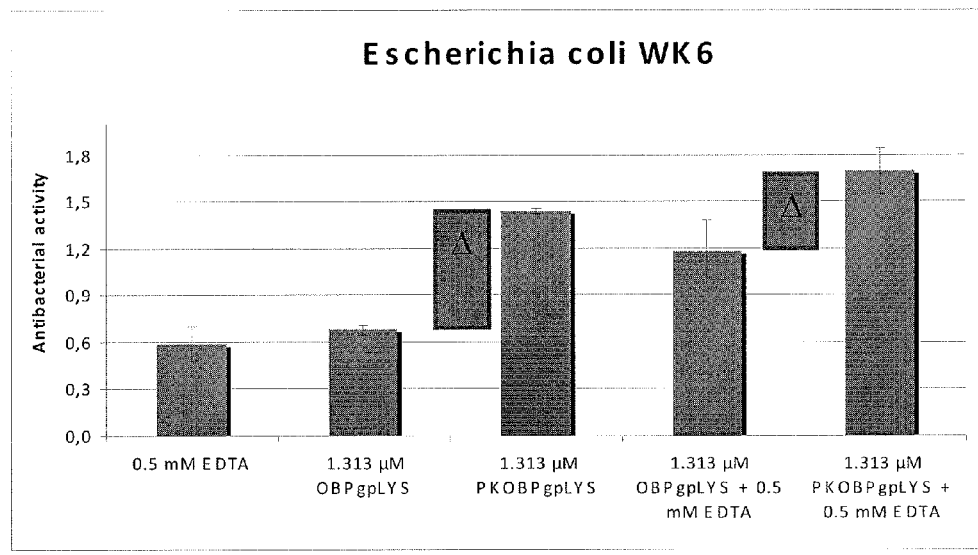
In FIG. 5 A the antibacterial activity on *Escherichia coli* WK 6 cells is represented, in FIG. 5B the antibacterial activity on *Salmonella typhimurium* LT2 (SGSC N° 2317) cells, in FIG. 5C the antibacterial activity on *Pseudomonas aeruginosa* PAO1p cells, in FIG. 5D the antibacterial activity on *Pseudomonas aeruginosa* Br667 cells, in FIG. 5E the antibacterial activity on *Pseudomonas putida* G1 cells and in FIG. 5F the antibacterial activity on *Burkholderia pseudomallei* cells. "Δ" gives the difference of antibacterial activity between the respective OBPgpLYS and PKOBPgpLYS samples. The error bars render the standard deviations of the mean.
Figure 5:
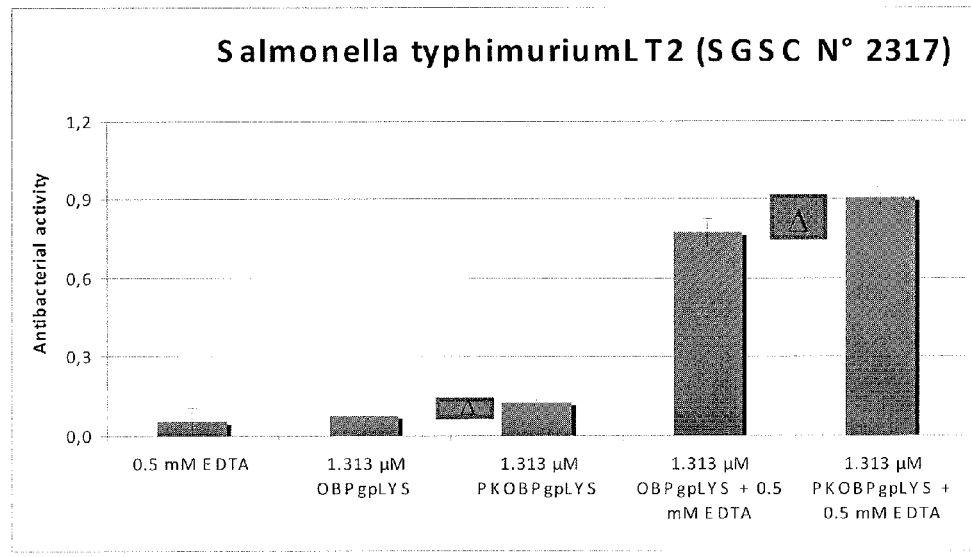
Figure 5:
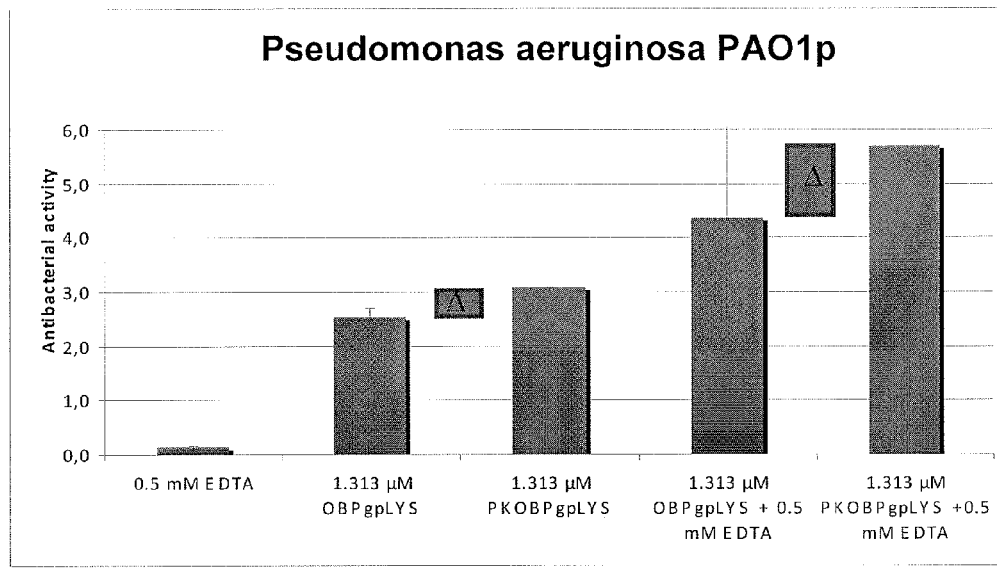
Figure 5:
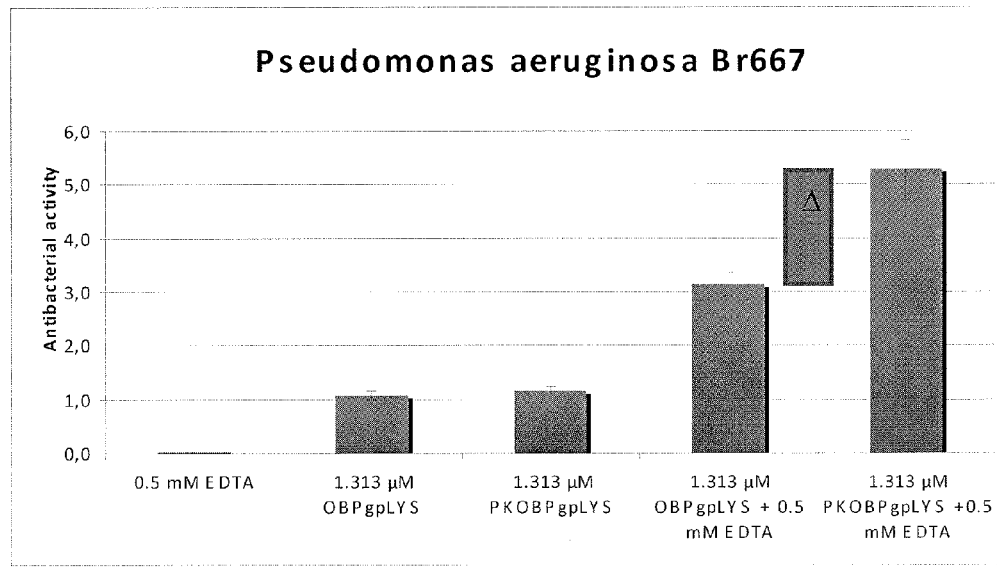
Figure 5:
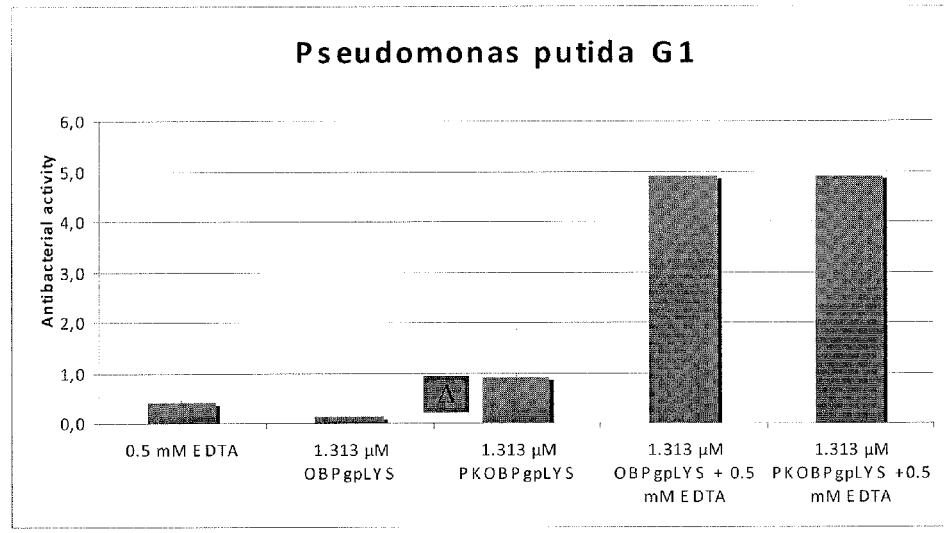
Figure 5:
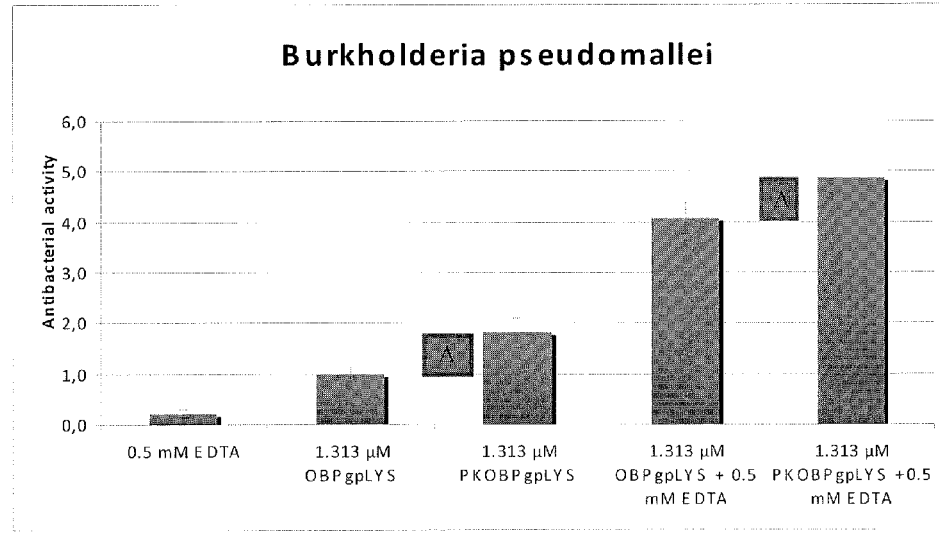

The term "protein" as used herein refers synonymously to the term "polypeptide". The term "protein" as used herein refers to a linear polymer of amino acid residues linked by peptide bonds in a specific sequence. The amino-acid residues of a protein may be modified by e.g. covalent attachments of various groups such as carbohydrates and phosphate. Other substances may be more loosely associated with the polypeptide chains, such as heme or lipid, giving rise to the conjugated proteins which are also comprised by the term "protein" as used herein. The various ways in which the polypeptide chains fold have been elucidated, in particular with regard to the presence of alpha helices and beta-pleated sheets. The term "protein" as used herein refers to all four classes of proteins being all-alpha, all-beta, alpha/beta and alpha plus beta.

The term "fusion protein" as used herein refers to an expression product resulting from the fusion of two nucleic acid sequences. Such a protein may be produced, e.g., in recombinant DNA expression systems. Moreover, the term "fusion protein" as used herein refers to a fusion of a first amino acid sequence as e.g. an endolysin, with a second or further amino acid sequence. The second or further amino acid sequence is preferably a peptide stretch, in particular a cationic peptide, a polycationic peptide, an amphipatic peptide, a sushi peptide, a defensin, a hydrophobic peptide or an antimicrobial peptide. Preferably, said second and/or further amino acid sequence is foreign to and not substantially homologous with any domain of the first amino acid sequence.

The term "peptide stretch" as used herein refers to any kind of peptide linked to a protein such as an endolysin. In particular the term "peptide stretch" as used herein refers to a cationic peptide, a polycationic peptide, an amphipatic peptide, a sushi peptide, a defensin, a hydrophobic peptide and/or an antimicrobial peptide. However, a peptide stretch in the meaning of the present invention does not refer to His$_6$-tags, Strep-tags, Avi-tags, Myc-tags, Gst-tags, JS-tags, cystein-tags, FLAG-tags or other tags known in the art, thioredoxin or maltose binding proteins (MBP). The term "tag" in contrast to the term "peptide stretch" as used herein refers to a peptide which can be useful to facilitate expression and/or affinity purification of a polypeptide, to immobilize a polypeptide to a surface or to serve as a marker or a label moiety for detection of a polypeptide e.g. by antibody binding in different ELISA assay formats as long as the function making the tag useful for one of the above listed facilitation is not caused by the positively charge of said peptide. However, the His$_6$-tag may, depending on the respective pH, also be positively charged, but is used as affinity purification tool as it binds to immobilized divalent cations and is not used as a peptide stretch according to the present invention.

The term "peptide" as used herein refers to short polypeptides consisting of from about 2 to about 100 amino acid residues, more preferably from about 4 to about 50 amino acid residues, more preferably from about 5 to about 30 amino acid residues, wherein the amino group of one amino acid residue is linked to the carboxyl group of another amino acid residue by a peptide bond. A peptide may have a specific function. A peptide can be a naturally occurring peptide or a synthetically designed and produced peptide. The peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). Preferred naturally occurring peptides are e.g. antimicrobial peptides, defensins, and sushi peptides. Preferred synthetically produced peptides are e.g. polycationic, amphiphatic or hydrophobic peptides. A peptide in the meaning of the present invention does not refer to His-tags, Strep-tags, thioredoxin or maltose binding proteins (MBP) or the like, which are used to purify or locate proteins.

The term "endolysin" as used herein refers to an enzyme which is suitable to hydrolyse bacterial cell walls. "Endolysins" comprise at least one "enzymatically active domain" (EAD) having at least one of the following activities: endopeptidase, N-acetyl-muramoyl-L-alanine-amidase (amidase), N-acetyl-muramidase, N-acetyl-glucosaminidase (lysozyme) or transglycosylases. In addition, the endolysins may contain also regions which are enzymatically inactive, and bind to the cell wall of the host bacteria, the so-called CBDs (cell wall binding domains). The endolysin may contain two or more CBDs. However, the term "endolysin" as used herein refers also to enzymes having at least one EAD but no CBDs. Generally, the cell wall binding domain is able to bind different components on the surface of bacteria. Preferably, the cell wall binding domain is a peptidoglycan binding domain and binds to the bacteria's peptidoglycan structure. The different domains of an endolysin can be connected by a domain linker.

The term "domain linker" as used herein refers to an amino acid sequence functioning to connect single protein domains with one another. As a rule domain linkers form no or only few regular secondary structure like α-helices or β-sheets and can occupy different conformations with the respective structural context. Methods to detect domain linker and properties of linker sequences are well known in the art as e.g. described in Bae et al., 2005, Bioinformatics, 21, 2264-2270 or George & Heringa, 2003, Protein Engineering, 15, 871-879.

The term "wild type" or "wt" as used herein refers to the amino acid sequence of the endolysin OBPgpLYS as depicted in SEQ ID NO: 86. The nucleic acid sequence encoding the wild type endolysin OBPgpLYS is depicted in SEQ ID NO: 101.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence.

The term "substitution" as used herein refers to the exchange of an amino acid residue located at a certain position for a different one.

The term "cell wall" as used herein refers to all components that form the outer cell enclosure of the Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "EAD" as used herein refers to the enzymatically active domain of an endolysin. The EAD is responsible for hydrolysing bacterial peptidoglycans. It exhibits at least one enzymatic activity of an endolysin. The EAD can also be composed of more than one enzymatically active module. The term "EAD" is used herein synonymously with the term "catalytic domain".

As used herein, the term "cationic peptide" refers to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides.

The term "polycationic peptide" as used herein refers to a synthetically produced peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP) as used herein refers to any peptide that has microbicidal and/or microbistatic activity. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties.

The term "defensin" as used herein refers to a peptide present within animals, preferably mammals, more preferably humans, wherein the defensin plays a role in the innate host defense system as the destruction of foreign substances such as infectious bacteria and/or infectious viruses and/or fungi. A defensin is a non-antibody microbicidal and/or tumoricidal protein, peptide or polypeptide. Examples for "defensins" are "mammalian defensins," alpha-defensins, beta-defensins, indolicidin and magainins. The term "defensins" as used herein refers both to an isolated form from animal cells or to a synthetically produced form, and refers also to variants which substantially retain the cytotoxic activities of their parent proteins, but whose sequences have been altered by insertion or deletion of one or more amino acid residues.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities.

The term "amphipathic peptide" as used herein refers to peptides having both hydrophilic and hydrophobic functional groups. Preferably, the term "amphipathic peptide" as used herein refers to a peptide having a defined arrangement of hydrophilic and hydrophobic groups e.g. amphipatic peptides may be e.g. alpha helical, having predominantly non polar side chains along one side of the helix and polar residues along the remainder of its surface.

The term "hydrophobic group" as used herein refers to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a nonaqueous environment. Examples of amino acid residues with hydrophobic side chains are valine, isoleucine, leucine, methionine, phenylalanine, tryptophan, cysteine, alanine, tyrosine, histidine, threonin, serine, proline and glycine residues.

The present invention relates to new antibacterial agents against Gram-negative bacteria. In particular the present invention relates to a polypeptide comprising an amino acid sequence according to SEQ ID NO: 1 or fragments or derivatives thereof The polypeptide comprising an amino acid sequence according to SEQ ID NO: 1 is preferably encoded by a nucleotide sequence according to SEQ ID NO: 3.

The endolysin OBPgpLYS having an amino acid sequence according to SEQ ID NO: 1 has a length of 328 amino acids. It comprises a N-terminal cell wall binding domain (CBD) and a C-terminal enzymatic active domain (EAD). The N-terminal CBD is a peptidoglycan binding domain (PGB, aa 7-96) having an amino acid sequence according to SEQ ID NO: 4. The C-terminal EAD is a catalytic domain (aa 126-292) complying with the catalytic domain of the lysozyme-like superfamiliy and having an amino acid sequence according to SEQ ID NO: 5. The PGB and the catalytic domain of the endolysin OBPgpLYS are connected by a domain linker.

Thus, preferred fragments of the polypeptide according to the present invention are polypeptides comprising an amino acid sequence according to SEQ ID NO: 4 and/or according to SEQ ID NO: 5. Another preferred fragment of the polypeptide according to the present invention comprises an amino acid sequence according to SEQ ID NO: 69. The fragment having an amino acid sequence according to SEQ ID NO: 69 differs from the polypeptide having an amino acid sequence according to SEQ ID NO: 1 in that the starting methionine residue has been deleted.

The derivatives according to the present invention are polypeptides comprising an amino acid sequence according to SEQ ID NO: 1, 4, 5 and/or 69 but having additional modification and/or alterations. Said modifications and/or alterations can be mutations in particular deletions, insertions, additions, substitutions or any combinations thereof and/or chemical changes of the amino acid residues, e.g. biotinylation, acetylation, pegylation, chemical changes of the amino-, SH— or carboxyl-groups. Said derivatives according to the present invention exhibit the lytic activity of the OBPgpLYS (SEQ ID NO: 1) and/or the activity of the fragments according to the present invention. Said activity can be about 10, 20, 30, 40, 50, 60, 70, 80, 90, 100, 110, 120, 130, 140, 150, 160, 170, 180, 190 or about 200% of the activity of the OBPgpLYS and/or the activity of the fragments according to the present invention. The activity can be measured by assays well known in the art by a person skilled in the art as e.g. the plate lysis assay or the liquid lysis assay which are e.g. described in (Briers et al., *J. Biochem. Biophys Methods* 70: 531-533, (2007)).

Preferred derivatives according to the present invention are polypeptides comprising an amino acid sequence according to SEQ ID NO: 86 and 87. Said derivatives differ from the polypeptides having an amino acid sequence according to SEQ ID NO: 1 and SEQ ID NO: 69, respectively, in that the leucine residue has been substituted by a histidine residue at positions 325 and 324, respectively. The polypeptide comprising an amino acid sequence according to SEQ ID NO: 86 is preferably encoded by a nucleotide sequence according to SEQ ID NO: 101.

In a preferred embodiment of the present invention the polypeptide, fragment and/or derivative according to the present invention comprises additionally a tag such as a $His_6$-tag, Strep-tag, Avi-tag, Myc-tag, Gst-tag, JS-tag, cystein-tag, FLAG-tag or other tags known in the art at the N-terminus or at the C-terminus. In a preferred embodiment of the present invention said tag is linked to the polypeptide, fragment and/or derivative according to the present invention at the C-terminus. Said tag may be linked to said polypeptide, fragment and/or derivative over additional amino acid residues. Said additional amino acid residues may be consist of at least 1, 2, 3, 4, 5, 6, 7, 8, 9 or 10 additional amino acid residues. In a preferred embodiment of the present invention the tag is linked to the polypeptide, fragment and/or derivative according to the present invention by the additional amino acid residues Leu-Glu or Lys-Gly.

In a preferred embodiment the present invention relates to polypeptides comprising an amino acid sequence according to SEQ ID NO: 47 or SEQ ID NO: 88. The polypeptide having an amino acid sequence according to SEQ ID NO: 47 and SEQ ID NO: 88, respectively, comprises in comparison to the polypeptide having an amino acid sequence according to SEQ ID NO: 1 and SEQ ID NO: 86, respectively, an additional C-terminal $His_6$-tag linked to the C-terminus of the polypeptide having an amino acid sequence according to SEQ ID NO: 1 and SEQ ID NO: 86, respectively, by the additional amino acid residues lysine and glycine (Lys-Gly). The polypeptide comprising an amino acid sequence according to SEQ ID NO: 47 is preferably encoded by a nucleotide sequence according to SEQ ID NO: 48. The polypeptide comprising an amino acid sequence according to SEQ ID NO: 88 is preferably encoded by a nucleotide sequence according to SEQ ID NO: 89.

A further aspect of the present invention are fusion proteins composed of an polypeptide, fragment and/or derivative according to the present invention and a peptide stretch fused to the polypeptide, fragment and/or derivative according to the present invention at the N- or C-terminus.

The peptide stretch of the fusion protein according to the present invention is preferably covalently bound to the polypeptide, fragment and/or derivative according to the present invention. Preferably, said peptide stretch consists of at least 5, more preferably at least of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100 amino acid residues. Especially preferred is a peptide stretch comprising about 5 to about 100 amino acid residues, about 5 to about 50 or about 5 to about 30 amino acid residues. More preferred is a peptide stretch comprising about 6 to about 42 amino acid residues, about 6 to about 39 amino acid residues, about 6 to about 38 amino acid residues, about 6 to about 31 amino acid residues, about 6 to about 25 amino acid residues, about 6 to about 24 amino acid residues, about 6 to about 22 amino acid residues, about 6 to about 21 amino acid residues, about 6 to about 20 amino acid residues, about 6 to about 19 amino acid residues, about 6 to about 16 amino acid residues, about 6 to about 14 amino acid residues, about 6 to about 12 amino acid residues, about 6 to about 10 amino acid residues or about 6 to about 9 amino acid residues. Preferably, the peptide stretch is no tag such as a $His_6$-tag, Strep-tag, Avi-tag, Myc-tag, Gst-tag, JS-tag, cystein-tag, FLAG-tag or other tags known in the art and no thioredoxin or maltose binding proteins (MBP). However, the peptide stretch may comprise in addition such tag or tags or the like, which are used to purify or locate proteins.

Figure 6:
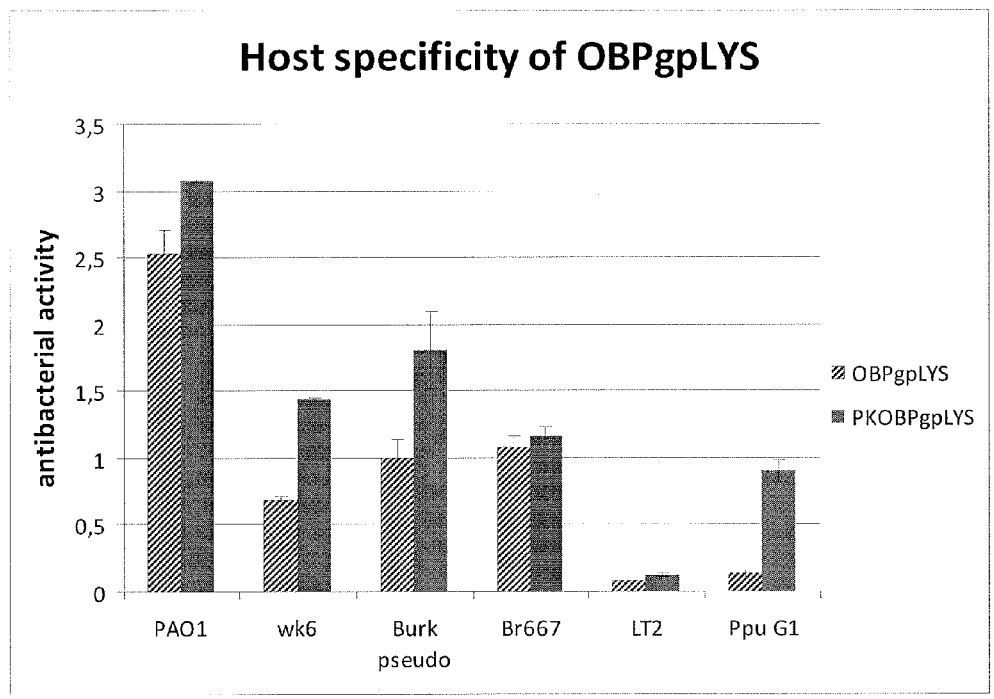
FIG. 6 shows in a graphic representation the host specificity of the unmodified OBPgpLYS (SEQ ID NO: 47) and the modified PKOBPgpLYS (SEQ ID NO: 49). Each species of Gram-negative bacteria was incubated for 30 minutes with a composition comprising each 1.315 µM unmodified OBPgpLYS or modified PKOBPgpLYS. The bar chart gives the antibacterial activities of the unmodified OBPgpLYS and modified OBPgpLYS on *Pseudomonas aeruginosa* PAO1p cells (PAO1), *Escherichia coli* WK6 cells (wk6), *Burkholderia pseudomallei* cells (Burk pseudo), *Pseudomonas aeruginosa* Br667 cells (Br667), *Salmonella typhimurium* LT2 cells (LT2) and *Pseudomonas putida* G1 cells (Ppu G1). The error bars indicate the standard deviations of the mean.

Preferably, the peptide stretch has the function to lead the fusion protein according to the present invention through the outer membrane of Gram-negative bacteria but has no or only low activity when administered without being fused to the polypeptide, fragment and/or derivative according to the present invention. The function to lead the fusion protein through the outer membrane of Gram-negative bacteria is caused by the potential of the membrane or LPS disrupting activity of said peptide stretch. To determine whether a peptide stretch has membrane or LPS disrupting activity said peptide stretch can be fused to a polypeptide according to the present invention as e.g. described in the Examples of the present invention. Subsequently, the antibacterial activity of the fusion protein consisting of the polypeptide according to the present invention and the peptide stretch to be tested can be compared to the polypeptide according the present invention having no peptide stretch as also described in the Examples of the present invention and e.g. shown in FIGS. 5A to F and 6. Preferably, said tests may be carried out on *Escherichia coli* WK6 and/or *Pseudomonas aeruginosa* PAO1p cells as used in the Examples of the present invention. In case the fusion protein has an increased antibacterial activity in comparison to the polypeptide according to the present invention without said peptide stretch for at least one of the tested gram-negative bacteria species then said peptide stretch has a membrane or LPS disrupting activity. Preferably, the antibacterial activity (in logarithmic units $(=\log_{10} N_0/N_i)$) of the polypeptide according to the present invention is increased by at least about 5%, more preferably by at least about 10%, by a peptide stretch having membrane or LPS disrupting activity.

In one aspect of the present invention the fused peptide stretch is an amphipathic peptide, which comprises one or more of the positively charged amino acid residues of lysine, arginine and/or histidine, combined to one or more of the hydrophobic amino acid residues of valine, isoleucine, leucine, methionine, phenylalanine, tryptophan, cysteine, alanine, tyrosine, histidine, threonin, serine, proline and/or glycine. Side chains of the amino acid residues are preferably oriented in order that cationic and hydrophobic surfaces are clustered at opposite sides of the peptide. Preferably, more than about 30, 40, 50, 60 or 70% of the amino acids in said peptide are positively charged amino acids. Preferably, more than about 30, 40, 50, 60 or 70% of the amino acid residues in said peptide are hydrophobic amino acid residues. Advantageously, the amphipathic peptide is fused at the N-terminal and/or the C-terminal end of the polypeptide, fragment and/or derivative according to the present invention having cell wall degrading activity, thus enhancing the amphipathicity of the latter proteins.

In a preferred embodiment at least about 30, 40, 50, 60 or 70% of the said amino acid residues of the amphipathic peptide are either arginine or lysine residues and/or at least about 30, 40, 50, 60 or 70% of the said amino acid residues of the amphipathic peptide are of the hydrophobic amino acid residues valine, isoleucine, leucine, methionine, phenylalanine, tryptophan, cysteine, alanine, tyrosine, histidine, threonin, serine, proline and/or glycine.

Preferred amphipatic peptides are Pleurocidin according to SEQ ID NO: 6, Cecropin P1 according to SEQ ID NO: 7, Buforin II according to SEQ ID NO: 8, Buforin I according to SEQ ID NO: 9 and Magainin according to SEQ ID NO: 10. Further preferred amphipatic peptides are Cathelidicine e.g. LL-37 according to SEQ ID NO: 11.

In a further aspect of the present invention the fused peptide stretch is an antimicrobial peptide, which comprises a positive net charge and around 50% hydrophobic amino acid residues. The antimicrobial peptides are amphipathic, with a length of about 12 to about 50 amino acid residues.

Preferred antimicrobial peptides are listed in the following table.

| Peptid | Sequenz | |
|---|---|---|
| LL-37 | LLGDFFRKSKEKIGKEFKRIVQRIKDFLRNLVPRTES | SEQ ID NO: 11 |
| SMAP-29 | RGLRRLGRKIAHGVKKYGPTVLRIIRIAG | SEQ ID NO: 12 |
| Indolicidin | ILPWKWPWWPWRR | SEQ ID NO: 13 |
| Protegrin | RGGRLCYCRRRFCVCVGR | SEQ ID NO: 14 |
| Cecropin P1 | SWLSKTAKKLENSAKKRISEGIAIAIQGGPR | SEQ ID NO: 7 |
| Magainin | GIGKFLHSAKKFGKAFVGEIMNS | SEQ ID NO: 10 |
| Pleurocidin | GWGSFFKKAAHVGKHVGKAALTHYL | SEQ ID NO: 6 |
| Cecropin A (A. aegypti) | GGLKKLGKKLEGAGKRVFNAAEKALPVVAGAKALRK | SEQ ID NO: 15 |
| Cecropin A (D. melanogaster) | GWLKKIGKKIERVGQHTRDATIQGLGIPQQAANVAATARGS | SEQ ID NO: 16 |
| Buforin II | TRSSRAGLQFPVGRVHRLLRK | SEQ ID NO: 8 |
| Sarcotoxin IA | GWLKKIGKKIERVGQHTRDATIQGLGIAQQAANVAATAR | SEQ ID NO: 17 |
| Ascaphine | GIKDWIKGAAKKLIKTVASHIANQ | SEQ ID NO: 50 |
| Apidaecine | ANRPVYIPPPRPPHPRL | SEQ ID NO: 51 |
| Nigrocine | GLLSKVLGVGKKVLCGVSGLVC | SEQ ID NO: 52 |

-continued

| Peptid | Sequenz | | |
|---|---|---|---|
| Pseudin 1 | GLNTLKKVFQGLHEAIKLINNHVQ | SEQ ID NO: | 53 |
| Parasin 1 | KGRGKQGGKVRAKAKTRSS | SEQ ID NO: | 72 |
| Lycotoxin | IWLTALKFLGKHAAKKLAKQQLSKL | SEQ ID NO: | 73 |
| Ranalexin | FLGGLIVPAMICAVTKKC | SEQ ID NO: | 117 |
| Melittin | GIGAVLKVLT TGLPALISWI KRKRQQ | SEQ ID NO: | 119 |

In a further aspect of the present invention the fused peptide stretch is a sushi peptide which is described by Ding J L, Li P, Ho B Cell Mol Life Sci. 2008 April; 65(7-8):1202-19. The Sushi peptides: structural characterization and mode of action against Gram-negative bacteria.

Preferred sushi peptides are sushi peptides S1 and S3 and multiples thereof; FASEB J. 2000 September; 14(12):1801-13.

In a further aspect of the present invention the fused peptide stretch is a defensin, preferably Cathelicidine, Cecropin P1, Cecropin A or Magainin II.

In a further aspect of the present invention the fused peptide stretch is a hydrophobic peptide, preferably having the amino acid sequence Phe-Phe-Val-Ala-Pro (SEQ ID NO:18).

Further preferred peptide stretches are listed in the following table:

| | | |
|---|---|---|
| Alpha 4 | PNRAKRVITTFRT | SEQ ID NO: 68 |
| Artilysin1 | GFFIPAVILPSIAFLIVP | SEQ ID NO: 70 |
| Artilysin2 | GKPGWLIKKALVFKKLIRRPLKRLA | SEQ ID NO: 71 |
| WLBU2 variant | KRWVKRVKRVKRWVKRVVRVVKRWVKR | SEQ ID NO: 118 |

In one aspect of the present invention the fused peptide stretch is an cationic and/or polycationic peptide, which comprises one or more of the positively charged amino acid residues of lysine, arginine and/or histidine, in particular of lysine and/or arginine. Preferably, more than about 20, 30, 40, 50, 60, 70, 75, 80, 85, 90, 95 or 99% of the amino acid residues in said peptide stretch are positively charged amino acid residues, in particular lysine and/or arginine residues. Especially preferred are peptide stretches consisting of about 100% positively charged amino acid residues, in particular arginine and/or lysine residues, wherein preferably about 60% to about 70% of said positively charged amino acid residues are lysine residues and about 30% to about 40% of said positively charged amino acid residues are arginine residues. More preferred is a peptide stretch consisting of about 100% positively charged amino acid residues, in particular arginine and/or lysine residues, wherein preferably about 64% to about 68% of said positively charged amino acid residues are lysine and about 32% to about 36% of said positively charged amino acid residues are arginine. Peptide stretches consisting of either only arginine or only lysine are also preferred.

Especially preferred are cationic and/or polycationic peptide stretches comprising at least one motive according to SEQ ID NO: 19 (KRKKRK). In particular cationic peptide stretches comprising at least 2, 3, 4, 5, 6, 7, 8, 9, 10, 11, 12, 13, 14, 15, 16 or 17 motives according to SEQ ID NO: 19 (KRKKRK) are preferred. More preferred are cationic peptide stretches comprising at least one KRK motive (lys-arg-lys), preferable at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 KRK motives.

In another preferred embodiment of the present invention the cationic peptide stretch comprises beside the positively charged amino acid residues, in particular lysine and/or arginine residues, neutrally charged amino acid residues, in particular glycine and/or serine residues. Preferred are cationic peptide stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% neutrally charged amino acid residues, in particular glycine and/or serine residues. Preferred are polypeptide stretches consisting of about 4% to about 8% serine residues, of about 33% to about 36% arginine residues and of about 56% to about 63% lysine residues. Especially preferred are polypeptide stretches comprising at least one motive according to SEQ ID NO: 40 (KRXKR), wherein X is any other amino acid residue than lysine, arginine and histidine. Especially preferred are polypeptide stretches comprising at least one motive according to SEQ ID NO: 41 (KRSKR). More preferred are cationic stretches comprising at least about 2, 3, 4, 5, 6, 7, 8, 9, 10, 11, 12, 13, 14, 15, 16, 17, 18, 19 or about 20 motives according to SEQ ID NO: 40 (KRXKR) or SEQ ID NO: 41 (KRSKR).

Also preferred are polypeptide stretches consisting of about 9 to about 16% glycine residues, of about 4 to about 11% serine residues, of about 26 to about 32% arginine residues and of about 47 to about 55% lysine residues. Especially preferred are polypeptide stretches comprising at least one motive according to SEQ ID NO: 42 (KRGSG). More preferred are cationic stretches comprising at least about 2, 3, 4, 5, 6, 7, 8, 9, 10, 11, 12, 13, 14, 15, 16, 17, 18, 19 or about 20 motives according to SEQ ID NO: 42 (KRGSG).

In another preferred embodiment of the present invention the cationic peptide stretch comprises beside the positively charged amino acid residues, in particular lysine and/or arginine residues, hydrophobic amino acid residues, in particular valine, isoleucine, leucine, methionine, phenylalanine, tryptophan, cysteine, alanine, tyrosine, histidine, threonin, serine, proline and/or glycine residues. Preferred are cationic peptide stretches consisting of about 70% to about 100%, or about 80% to about 95%, or about 85% to about 90% positively charged amino acid residues, in particular lysine and/or arginine residues and of about 0% to about 30%, or about 5% to about 20%, or about 10% to about 20% hydrophobic amino acid residues in particular valine, isoleucine, leucine, methionine, phenylalanine, tryptophan, cysteine, alanine, tyrosine, histidine, threonin, serine, proline and/or glycine residues.

Especially preferred are peptide stretches selected from the group consisting of the following sequences:

| Peptide stretch | length | SEQ ID NO: |
|---|---|---|
| KRKKRK | 6 | SEQ ID NO: 19 |
| KRKKRKKRK | 9 | SEQ ID NO: 20 |
| RRRRRRRRR | 9 | SEQ ID NO: 21 |
| KKKKKKKK | 8 | SEQ ID NO: 22 |
| KRKKRKKRKK | 10 | SEQ ID NO: 23 |
| KRKKRKKRKKRK | 12 | SEQ ID NO: 24 |
| KRKKRKKRKKRKKR | 14 | SEQ ID NO: 25 |
| KKKKKKKKKKKKKKKK | 16 | SEQ ID NO: 26 |
| KRKKRKKRKRKKRKKRKK | 19 | SEQ ID NO: 27 |
| RRRRRRRRRRRRRRRRRRR | 19 | SEQ ID NO: 28 |
| KKKKKKKKKKKKKKKKKKK | 19 | SEQ ID NO: 29 |
| KRKKRKKRKRSKRKKRKKRK | 20 | SEQ ID NO: 30 |
| KRKKRKKRKRSKRKKRKKRKK | 21 | SEQ ID NO: 31 |
| KRKKRKKRKRKRKKRKKRKRK | 21 | SEQ ID NO: 32 |
| KRKKRKKRKRGSGKRKKRKKRK | 22 | SEQ ID NO: 33 |
| KRKKRKKRKRGSGSGKRKKRKKRK | 24 | SEQ ID NO: 34 |
| KRKKRKKRKKRKKRKKRKKRKKRKK | 25 | SEQ ID NO: 35 |
| KRKKRKKRKRSKRKKRKKRKRSKRKKRKKRK | 31 | SEQ ID NO: 36 |
| KRKKRKKRKRGSGSGKRKKRKKRKRKGSGSGKRKKRKKRK | 38 | SEQ ID NO: 37 |
| KRKKRKKRKRKKRKKRKKRKKRKKRKKRKKRKKRKKRKK | 39 | SEQ ID NO: 38 |
| KRKKRKKRKRSKRKKRKKRKRSKRKKRKKRKRSKRKKRKKRK | 42 | SEQ ID NO: 39 |

Especially preferred is a fusion protein comprising a polypeptide, fragment and/or derivative according to the present invention and a peptide stretch having an amino acid sequence according to SEQ ID NO: 20. More preferred are fusion proteins having an amino acid sequence according to SEQ ID NO: 43 and SEQ ID NO: 115. Also preferred are fusion proteins an amino acid sequence according to SEQ ID NO: 49 and SEQ ID NO: 116. The fusion proteins having an amino acid sequence according to SEQ ID NO: 49 and SEQ ID NO: 116, respectively, comprises in comparison to the fusion proteins having an amino acid sequence according to SEQ ID NO: 43 and SEQ ID NO: 115, respectively, an additional C-terminal $His_6$-tag linked to the C-terminus of the fusion protein having an amino acid sequence according to SEQ ID NO: 43 and SEQ ID NO: 115, respectively, by the additional amino acid residues lysine and glycine (Lys-Gly). The fusion proteins having an amino acid sequence according to SEQ ID NO: 43 and SEQ ID NO: 115 and SEQ ID NO: 49 and SEQ ID NO: 116, respectively, differ in that the fusion proteins having an amino acid sequence according to SEQ ID NO: 115 and SEQ ID NO: 116 has each a substitution of the leucine residue to a histidine residue at position 336.

In another preferred embodiment of the present invention the peptide stretches of the fusion protein according to the present invention comprise modifications and/or alterations of the amino acid sequences. Such alterations and/or modifications may comprise mutations such as deletions, insertions and additions, substitutions or combinations thereof and/or chemical changes of the amino acid residues, e.g. biotinylation, acetylation, peglyation, chemical changes of the amino-, SH— or carboxyl-groups.

A fusion protein according to the present invention as already outlined above is composed of
 (a) an polypeptide, fragment and/or derivative according to the present invention, and
 (b) a peptide stretch fused to said polypeptide, fragment and/or derivative at the N- or C-Terminus, and optionally
 (c) a tag, such as a $His_6$-tags, Strep-tags, Avi-tags, Myc-tags, Gst-tags, JS-tags, cystein-tags, FLAG-tags or other tags known in the art at the N- or C-Terminus.

In case the peptide stretch is fused to the polypeptide, fragment and/or derivative according to the present invention at the C-Terminus, the fusion protein comprises the additional tag preferably at the N-terminus. In an especially preferred embodiment of the present invention the peptide stretch is fused to the polypeptide, fragment and/or derivative according to the present invention at the N-Terminus. In case said fusion protein comprises an additional tag said tag is preferably at the C-terminus.

The two and three components of the fusion protein, respectively, as outlined above may be linked to each other over additional amino acid residues e.g. due to cloning reasons. Moreover, the peptide stretch may be linked to the starting methionine residue of the fusion protein by additional amino acid residues. Said additional amino acid residues may be consist of at least 1, 2, 3, 4, 5, 6, 7, 8, 9 or 10 additional amino acid residues. In a preferred embodiment of the present invention the peptide stretch is linked to the polypeptide, fragment and/or derivative according to the present invention by the additional amino acid residues Gly-Ser or Gly-Gly-Ser. The additional amino acid residues linking the starting methionine residue and the peptide stretch are preferably Gly-Ser. In case the fusion protein additionally comprises a tag, the polypeptide, fragment and/or derivative according to the present invention is preferably linked to said tag by the additional amino acid residues Leu-Glu or Lys-Gly.

The following table exemplifies the above outlined assembly of specifically preferred fusion proteins according to the present invention listed in the first column starting with the starting methionine residue at the N-terminus in the second column and ending with the optional tag at the C-terminus in the last column:

| Fusion protein according to the present invention (SEQ ID NO:) | First amino acid residue (N-term) | additional amino acid residues | peptide stretch (SEQ ID NO:) | additional amino acid residues | polypeptide, fragment, derivative according to the present invention (SEQ ID NO:) | additional amino acid residues | tag (C-term) |
|---|---|---|---|---|---|---|---|
| SEQ: 43 | Met | — | SEQ: 20 | Gly-Ser | SEQ: 69 | — | — |
| SEQ: 49 | Met | — | SEQ: 20 | Gly-Ser | SEQ: 69 | Lys-Gly | HIS$_6$-tag |
| SEQ: 54 | Met | — | SEQ: 50 | Gly-Ser | SEQ: 87 | — | — |
| SEQ: 55 | Met | — | SEQ: 50 | Gly-Ser | SEQ: 87 | Leu-Glu | HIS$_6$-tag |
| SEQ: 56 | Met | — | SEQ: 51 | Gly-Ser | SEQ: 87 | — | — |
| SEQ: 57 | Met | — | SEQ: 51 | Gly-Ser | SEQ: 87 | Leu-Glu | HIS$_6$-tag |
| SEQ: 58 | Met | — | SEQ: 52 | Gly-Ser | SEQ: 87 | — | — |
| SEQ: 59 | Met | — | SEQ: 52 | Gly-Ser | SEQ: 87 | Leu-Glu | HIS$_6$-tag |
| SEQ: 60 | Met | — | SEQ: 53 | Gly-Ser | SEQ: 87 | — | — |
| SEQ: 61 | Met | — | SEQ: 53 | Gly-Ser | SEQ: 87 | Leu-Glu | HIS$_6$-tag |
| SEQ: 62 | Met | — | SEQ: 17 | Gly-Ser | SEQ: 87 | — | — |
| SEQ: 63 | Met | — | SEQ: 17 | Gly-Ser | SEQ: 87 | Leu-Glu | HIS$_6$-tag |
| SEQ: 64 | Met | — | SEQ: 12 | Gly-Ser | SEQ: 87 | — | — |
| SEQ: 65 | Met | — | SEQ: 12 | Gly-Ser | SEQ: 87 | Leu-Glu | HIS$_6$-tag |
| SEQ: 66 | Met | — | SEQ: 15 | Gly-Ser | SEQ: 87 | — | — |
| SEQ: 67 | Met | — | SEQ: 15 | Gly-Ser | SEQ: 87 | Leu-Glu | HIS$_6$-tag |
| SEQ: 74 | Met | Gly-Ser | SEQ: 68 | Gly-Ser-Ser | SEQ: 87 | — | — |
| SEQ: 75 | Met | Gly-Ser | SEQ: 68 | Gly-Ser-Ser | SEQ: 87 | Lys-Gly | HIS$_6$-tag |
| SEQ: 76 | Met | Gly-Ser | SEQ: 69 | Gly-Ser-Ser | SEQ: 87 | — | — |
| SEQ: 77 | Met | Gly-Ser | SEQ: 69 | Gly-Ser-Ser | SEQ: 87 | Lys-Gly | HIS$_6$-tag |
| SEQ: 78 | Met | Gly-Ser | SEQ: 70 | Gly-Ser-Ser | SEQ: 87 | — | — |
| SEQ: 79 | Met | Gly-Ser | SEQ: 70 | Gly-Ser-Ser | SEQ: 87 | Lys-Gly | HIS$_6$-tag |
| SEQ: 80 | Met | Gly-Ser | SEQ: 71 | Gly-Ser-Ser | SEQ: 87 | — | — |
| SEQ: 81 | Met | Gly-Ser | SEQ: 71 | Gly-Ser-Ser | SEQ: 87 | Lys-Gly | HIS$_6$-tag |
| SEQ: 82 | Met | Gly-Ser | SEQ: 72 | Gly-Ser-Ser | SEQ: 87 | — | — |
| SEQ: 83 | Met | Gly-Ser | SEQ: 72 | Gly-Ser-Ser | SEQ: 87 | Lys-Gly | HIS$_6$-tag |
| SEQ: 84 | Met | Gly-Ser | SEQ: 73 | Gly-Ser-Ser | SEQ: 87 | — | — |
| SEQ: 85 | Met | Gly-Ser | SEQ: 73 | Gly-Ser-Ser | SEQ: 87 | Lys-Gly | HIS$_6$-tag |
| SEQ: 115 | Met | — | SEQ: 20 | Gly-Ser | SEQ: 87 | — | — |
| SEQ: 116 | Met | — | SEQ: 20 | Gly-Ser | SEQ: 87 | Lys-Gly | HIS$_6$-tag |

The present invention further relates to an isolated nucleic acid molecule encoding the polypeptide, fragment, derivative and/or fusion protein according to the present invention. Especially preferred isolated nucleic acid molecules according to the present invention comprise a nucleic acid sequence according to SEQ ID NO: 2, 3, 48, 89 or 101. The present invention further relates to a vector comprising the nucleic acid molecule according to the present invention. Said vector may provide for the constitutive or inducible expression of said polypeptide, fragment, derivative and/or fusion protein according to the present invention.

The invention also relates to a method for obtaining said polypeptide, fragment, derivative and/or fusion proteins from a micro-organism, such as a genetically modified suitable host cell which expresses said polypeptide, fragment, derivative and/or fusion proteins. Said host cell may be a micro-organism such as bacteria or yeast or an animal cell as e.g. a mammalian cell, in particular a human cell. In one embodiment of the present invention the host cell is an *Escherichia coli* cell. The host may be selected due to mere biotechnological reasons, e.g. yield, solubility, costs, etc. but may be also selected from a medical point of view, e.g. a non-pathological bacteria or yeast or human cells. Another aspect of the present invention is related to a method for genetically transforming a suitable host cell in order to obtain the expression of the polypeptide, fragment, derivative and/or fusion proteins according to the present invention, wherein the host cell is genetically modified by the introduction of a genetic material encoding said polypeptide, fragment, derivative and/or fusion proteins into the host cell and obtain their translation and expression by genetic engineering methods well known by the man skilled in the art.

In a further aspect the present invention relates to a composition, preferably a pharmaceutical composition, comprising a polypeptide, fragment, derivative and/or fusion protein according to the present invention and/or a host transformed with a nucleic acid molecule or a vector comprising a nucleotide sequence encoding a polypeptide, fragment, derivative and/or fusion protein according to the present invention.

In a preferred embodiment of the present invention the composition comprises additionally agents permeabilizing the outer membrane of Gram-negative bacteria such metal chelators as e.g. EDTA, TRIS, lactic acid, lactoferrin, polymyxin, citric acid and/or other substances as described e.g. by Vaara (Agents that increase the permeability of the outer membrane. Vaara M. Microbiol Rev. 1992 September; 56(3): 395-441). Also preferred are compositions comprising combinations of the above mentioned permeabilizing agents. Especially preferred is a composition comprising about 10 µM to about 100 mM EDTA, more preferably about 50 µM to about 10 mM EDTA, more preferably about 0.5 mM to about 10 mM EDTA, more preferably about 0.5 mM to about 2 mM EDTA, more preferably about 0.5 mM to about 1 mM EDTA. Also preferred is a composition comprising about 0.5 mM to about 2 mM EDTA, more preferably about 1 mM EDTA and additionally about 10 to about 100 mM TRIS.

The present invention also relates to a polypeptide, fragment, derivative and/or fusion protein according to the present invention and/or a host transformed with a nucleic acid comprising a nucleotide sequence encoding a polypeptide, fragment, derivative and/or fusion protein according to the present invention for use as a medicament. In a further aspect the present invention relates to the use of a polypeptide, fragment, derivative and/or fusion protein according to the present invention and/or a host transformed with a vector comprising a nucleic acid molecule comprising a nucleotide sequence encoding a polypeptide, fragment, derivative and/or fusion protein according to the present invention in the manufacture of a medicament for the treatment and/or prevention of a disorder, disease or condition associated with Gram-negative bacteria. In particular the treatment and/or prevention of the disorder, disease or condition may be caused by Gram-negative bacteria of bacterial groups, families, genera or species comprising strains pathogenic for humans or animals like Enterobacteriaceae (*Escherichia*, especially *E. coli, Salmonella, Shigella, Citrobacter, Edwardsiella, Enterobacter, Hafnia, Klebsiella*, especially *K. pneumoniae, Morganella, Proteus, Providencia, Serratia, Yersinia*), Pseudomonadaceae (*Pseudomonas*, especially *P. aeruginosa, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella,* Spirochaetaceae (*Treponema* and *Borrelia*), Leptospiraceae, *Campylobacter, Helicobacter, Spirillum, Streptobacillus,* Bacteroidaceae (*Bacteroides, Fusobacterium, Prevotella, Porphyromonas*), *Acinetobacter*, especially *A. baumanii*. In particular, the treatment and/or prevention of the disorder, disease or condition may be caused by *Pseudomonas aeruginosa, Pseudomonas putida, Burkholderia pseudomallei, E. coli* and/or *Salmonella typhimurium*.

The present invention further relates to a medicament comprising a polypeptide, fragment, derivative and/or fusion protein according to the present invention and/or a host transformed with a nucleic acid comprising a nucleotide sequence encoding a polypeptide, fragment, derivative and/or fusion protein according to the present invention.

In a further aspect the present invention relates to a method of treating a disorder, disease or condition in a subject in need of treatment and/or prevention, which method comprises administering to said subject an effective amount of a polypeptide, fragment, derivative and/or fusion protein according to the present invention and/or an effective amount of a host transformed with a nucleic acid comprising a nucleotide sequence encoding a polypeptide, fragment, derivative and/or fusion protein according to the present invention or a composition according to the present invention. The subject may be a human or an animal.

In particular said method of treatment may be for the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis caused by Gram-negative bacteria, in particular by the Gram-negative bacteria as listed above.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of a polypeptide, fragment, derivative and/or fusion protein according to the present invention and/or an effective amount of a host transformed with a nucleic acid comprising a nucleotide sequence encoding a polypeptide, fragment, derivative and/or fusion protein according to the present invention or a composition according to the present invention to a site of infection (or site endangered to be infected) a formulation may be used that protects the active compounds from environmental influences such as proteases, oxidation, immune response etc., until it reaches the site of infection. Therefore, the formulation may be capsule, dragee, pill, suppository, injectable solution or any other medical reasonable galenic formulation. Preferably, the galenic formulation may comprise suitable carriers, stabilizers, flavourings, buffers or other suitable reagents. For example, for topical application the formulation may be a lotion or plaster, for nasopharyngeal application the formulation may be saline solution to be applied via a spray to the nose.

Preferably, a polypeptide, fragment, derivative and/or fusion protein according to the present invention is used for medical treatment, if the infection to be treated (or prevented) is caused by multiresistant bacterial strains, in particular by strains resistant against one or more of the following antibiotics: streptomycin, tetracycline, cephalothin, gentamicin, cefotaxime, cephalosporin, ceftazidime or imipenem. Furthermore, a polypeptide, fragment, derivative and/or fusion protein according to the present invention can be used in methods of treatment by administering it in combination with conventional antibacterial agents, such as antibiotics, lantibiotics, bacteriocins or endolysins, etc.

The present invention also relates to a pharmaceutical pack comprising one or more compartments, wherein at least one compartment comprises one or more polypeptide, fragment, derivative and/or fusion protein according to the present invention and/or one or more hosts transformed with a nucleic acid comprising a nucleotide sequence encoding a polypeptide, fragment, derivative and/or fusion protein according to the present invention or a composition according to the present invention.

In another aspect the present invention relates to a process of preparation of a pharmaceutical composition, said process comprising admixing one or more polypeptide, fragment, derivative and/or fusion protein according to the present invention and/or one or more hosts transformed with a nucleic acid comprising a nucleotide sequence encoding a polypeptide, fragment, derivative and/or fusion protein according to the present invention with a pharmaceutically acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the polypeptide, fragment, derivative and/or fusion protein according to the present invention in order to degrade already existing or freshly settling pathogenic Gram-negative bacteria.

In a further aspect the present invention relates to the polypeptide, fragment, derivative and/or fusion protein according to the present invention for use as diagnostic means in medicinal, food or feed or environmental diagnostics, in particular as a diagnostic means for the diagnostic of bacteria infection caused in particular by Gram-negative bacteria. In this respect the polypeptide, fragment, derivative and/or fusion protein according to the present invention may be used as a tool to specifically degrade pathogenic bacteria, in particular Gram-negative pathogenic bacteria. The degradation of the bacterial cells by the polypeptide, fragment, derivative and/or fusion protein according to the present invention can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the polypeptide, fragment, derivative and/or fusion protein according to the present invention for the treatment or prevention of Gram-negative bacterial contamination of foodstuff, of food processing equipment, of food processing plants, of surfaces coming into contact with foodstuff such as shelves and food deposit areas and in all other situations, where pathogenic, facultative pathogenic or other undesirable bacteria can potentially infest food material, of medical devices and of all kind of surfaces in hospitals and surgeries.

In particular, a polypeptide, fragment, derivative and/or fusion protein of the present invention may be used prophylactically as sanitizing agent. Said sanitizing agent may be used before or after surgery, or for example during hemodialysis. Moreover, premature infants and immunocompromised persons, or those subjects with need for prosthetic devices may be treated with a fusion protein according to the present invention. Said treatment may be either prophylactically or during acute infection. In the same context, nosocomial infections, especially by antibiotic resistant strains like *Pseudomonas aeruginosa* (FQRP), *Acinetobacter* species and Enterobacteriaceae such as *E. coli, Salmonella, Shigella, Citrobacter, Edwardsiella, Enterobacter, Hafnia, Klebsiella, Morganella, Proteus, Providencia, Serratia* and *Yersinia* species may be treated prophylactically or during acute phase with a polypeptide, fragment, derivative and/or fusion protein of the present invention. Therefore, a polypeptide, fragment, derivative and/or fusion protein according to the present invention may be used as a disinfectant also in combination with other ingredients useful in a disinfecting solution like detergents, tensids, solvents, antibiotics, lantibiotics, or bacteriocins.

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

EXAMPLE 1

Modified Endolysin Variants of *Pseudomonas putida* Phage OBP

OBPgpLYS having an amino acid sequence according to SEQ ID NO: 1 is a modular endolysin of 332 amino acid residues originating from *Pseudomonas putida* phage OBP with a putative N-terminal peptidoglycan binding domain and a C-terminal catalytic chitinase domain. OPBgpLYS having an amino acid sequence according to SEQ ID NO: 47 comprises in comparison to OBPgpLYS having an amino acid sequence according to SEQ ID NO: 1 an additional C-terminal His$_6$-tag linked to the C-terminus by the additional amino acid residues lysin and glycin (Lys-Gly)

Purified genomic DNA of phage OBP was used as a template for the amplification of the open reading frame (ORF) of OBPgpLYS in standard PCR reaction with Pfu polymerase (Fermentas, Ontario, Canada) using the following PCR parameters:

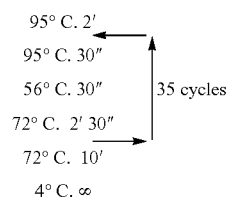

Therefore a standard 5' primer (5' ATGAAAAATAGC-GAGAAGAAT 3' (SEQ ID NO: 44)) and a standard 3' primer (5' AACTATTCCGAGTGCTTTCTTTGT 3' (SEQ ID NO: 45)) was used. To extend the 5' end of the ORF which encodes OBPgpLYS with a gene fragment encoding the polycationic 9-mer peptide Lys-Arg-Lys-Lys-Arg-Lys-Lys-Arg-Lys- (SEQ ID NO: 20) a tail PCR (with same parameters as standard PCR above) with an extended 5' primer (5' ATGGGATC-CAAACGCAAGAAACGTAAGAAACG-CAAAAAAAATAGCGAG AAGAAT 3' (SEQ ID NO: 46)) and the standard 3' primer according to SEQ ID NO: 45 was applied. Both the original unmodified OBPgpLYS PCR fragment and the extended fragment were ligated in the pEXP5CT/TOPO® expression vector (Invitrogen, Carlsbad, Calif., USA) by following the TA-cloning protocol of the manufacturer.

Recombinant expression of OBPgpLYS having an amino acid sequence according to SEQ ID NO: 47 and PKOBPg-pLYS having an amino acid sequence according to SEQ ID NO: 49 is performed in exponentially growing E. coli BL21 (λDE3) pLysS cells (Invitrogen) after induction with 1 mM IPTG (isopropylthiogalactoside) at 37° C. for a period of 4 hours. Both proteins were purified by $Ni^{2+}$ affinity chromatography (Akta FPLC, GE Healthcare) using the C-terminal 6× His-tag, encoded by the pEXP5CT/TOPO® expression vector. The $Ni^{2+}$ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM $NaH_2PO_4$-NaOH on pH 7.4) at a flow rate of 0.5 ml/min.
2. Loading of the total lysate (with wanted endolysin) on the Histrap HP 1 ml column at a flow rate of 0.5 ml/min.
3. Washing of the column with 15 column volumes of Washing Buffer at a flow rate of 1 ml/min.
4. Elution of bounded endolysin from the column with 10 column volumes of Elution Buffer (500 mM imidazole, 0.5 M NaCl and 20 mM $NaH_2PO_4$-NaOH on pH 7.4) at a flow rate of 0.5 ml/min The total yields of both purified recombinant proteins per liter E. coli expression culture is shown in Table 1. The values were determined by spectrophotometric measurement of the protein concentration and the total volume of the purified stock solution at a wavelength of 280 nm. Purified stock solutions consisting of OBPgpLYS and PKOBPgpLYS, respectively, in Elution Buffer (20 mM $NaH_2PO_4$-NaOH pH7.4; 0.5 M NaCl; 500 mM imidazole) were at least 90% pure as determined visually on SDS-PAGE gels.

TABLE 1

Yields of purified recombinant OBPgpLYS endolysin and its PK-modified PKOBPgpLYS per liter E. coli expression culture.

| Endolysins | Expression yield |
| --- | --- |
| OBPgpLYS (SEQ ID NO: 47) | 3.3 mg |
| PKOBPgpLYS (SEQ ID NO: 49) | 4.7 mg |

To determine the anti-Gram-negative spectrum of the endolysins OBPgpLYS according to SEQ ID NO: 47 and PKOBPgpLYS according to SEQ ID NO: 49, a combination of 1.313 µM of each endolysin and 0.5 mM EDTA was tested on the clinical multiresistant P. aeruginosa strain Br667, Pseudomonas putida G1 (host of phage OBP) and a range of other Gram-negative pathogens (P. aeruginosa PAO1p, P. aeruginosa Br667, P. putida G1, Burkholderia pseudomallei, Escherichia coli WK6 and Salmonella typhimurium) (see Table 3). Exponential growing bacterial cells ($OD_{600\ nm}$ of 0.6) were 100-fold diluted to a final density of about $10^6$ cells/ml of each strain was incubated for 30 minutes at room temperature without shaking with unmodified endolysin OBPgpLYS (SEQ ID NO: 47) and modified endolysin PKOBPgpLYS (SEQ ID NO: 49) each in combination without and with 0.5 mM EDTA. For incubation, the endolysins were used each in buffer (20 mM $NaH_2PO_4$-NaOH pH7.4; 0.5 M NaCl; 0.5 M imidazole) and the incubation took place at a final concentration of endolysin of 1,313 µM. As a control each strain was also incubated for 30 minutes with 0.5 mM EDTA (in same buffer as outlined above) but no endolysin. After incubation cell suspensions were diluted three times (respectively $10^5$-$10^4$-$10^3$ cells/ml) and 100 µl of each dilution was plated out on LB-medium. The residual colonies were counted after an overnight incubation at 37° C. Based on the counted cell numbers the antibacterial activity as the relative inactivation in logarithmic units (=$\log_{10} N_0/N_1$ with $N_0$=number of untreated cells and $N_i$=number of treated cells, both counted after incubation) was calculated (Table 2). All samples were replicated in threefold. Averages +/− standard deviations are represented. The maximal reduction observed is dependent on the detection level of 10 cells/ml and the initial cell density.

TABLE 2

Antibacterial activity of unmodified endolysin (OBPgpLYS) and its modified endolysin variant (PKOBPgpLYS) with and without EDTA-$Na_2$ on different exponential growing Gram-negative species in logarithmic units.

| | 0.5 mM EDTA | 1.313 µM OBPgpLYS | 1.313 µM PKOBPgpLYS | 1.313 µM OBPgpLYS + 0.5 mM EDTA | 1.313 µM PKOBPgpLYS + 0.5 mM EDTA |
| --- | --- | --- | --- | --- | --- |
| P. aeruginosa PAO1p | 0.130 +/− 0.023 | 2.531 +/− 0.173 | 3.079 +/− 0.015 | 4.357 +/− 1.857 | >5.687 |

TABLE 2-continued

Antibacterial activity of unmodified endolysin (OBPgpLYS) and its modified endolysin variant (PKOBPgpLYS) with and without EDTA-Na$_2$ on different exponential growing Gram-negative species in logarithmic units.

|  | 0.5 mM EDTA | 1.313 µM OBPgpLYS | 1.313 µM PKOBPgpLYS | 1.313 µM OBPgpLYS + 0.5 mM EDTA | 1.313 µM PKOBPgpLYS + 0.5 mM EDTA |
|---|---|---|---|---|---|
| P. aeruginosa Br667 | 0.031 +/− 0.023 | 1.082 +/− 0.083 | 1.163 +/− 0.063 | 3.144 +/− 0.223 | 5.272 +/− 0.573 |
| P. putida G1 | 0.412 +/− 0.055 | 0.141 +/− 0.027 | 0.904 +/− 0.079 | 4.891 +/− 0.000 | >4.891 |
| Burkholderia pseudomallei | 0.220 +/− 0.081 | 0.997 +/− 0.131 | 1.806 +/− 0.287 | 4.08 +/− 0.301 | >4.861 |
| Escherichia coli WK6 | 0.592 +/− 0.113 | 0.681 +/− 0.032 | 1.434 +/− 0.018 | 1.179 +/− 0.200 | 1.695 +/− 0.147 |
| Salmonella typhimurium | 0.054 +/− 0.048 | 0.076 +/− 0.011 | 0.127 +/− 0.013 | 0.774 +/− 0.052 | 0.908 +/− 0.037 |

While the global efficacy of the OBPgpLYS treatment is species dependent, the results in Table 2 show an added effect of the PKOBPgpLYS compared to unmodified OBPgpLYS for all bacterial species tested, both in the absence as the presence of 0.5 mM EDTA. For *Pseudomonas* and *Burkholderia* species, a clear synergistic effect with EDTA is observed for the PKOBPgpLYS activity.

TABLE 3

List of used Gram-negative strains

| Grain-negative strain | Source | Reference |
|---|---|---|
| Pseudomonas aeruginosa PAO1p | Burn wound isolate, Queen Astrid Hospital, Brussels | Pirnay et al., 2003* |
| Pseudomonas aeruginosa Br667 | Burn wound isolate, Queen Astrid Hospital, Brussels | Pirnay et al., 2003* |
| Pseudomonas putida G1 | Soil isolate, Moskow | Prof V. Krylov** |
| Burkholderia pseudomallei | Clinical isolate, UZ Gasthuisberg, Leuven | Prof J. Verhaegen*** |
| Escherichia coli WK6 | Standard laboratory expression strain | Stratagene**** |
| Salmonella typhimurium LT2 | SGSC N° 2317 | Prof C. Michiels***** |

*Pirnay JP, De Vos D, Cochez C, Bilocq F, Pirson J, Struelens M, Duinslaeger L, Cornelis P, Zizi M, Vanderkelen A. (2003). Molecular epidemiology of Pseudomonas aeruginosa colonization in a burn unit: persistence of a multidrug-resistant clone and a silver sulfadiazine-resistant clone. *J Clin Microbiol.*, 41(3): 1192-1202.

**State Research Institute for Genetics and Selection of Industrial Microorganisms, Moscow 113545, 1st Dorozhnii projezd, 1, Russia

***Afd. Experiment. Laboratoriumgeneesk., UZ Herestraat 49 - bus 7003, 3000 Leuven, Belgium

****STANSSENS, P., OPSOMER, C., MCKEOWNY, M., KRAMER, W., ZABEAU, M. and FRITZ, H.-J. (1989). Efficient oligonucleotide-directed construction of mutations in expression vectors by the gapped duplex DNA method using alternating selectable markers. NucleiC Acids Research 17, 4441-4454.

*****Centr. Levensmidd.- & Microb. Technol., Kasteelpark Arenberg 23 - bus 2457, 3001 Heverlee, Belgium

EXAMPLE 2

Effect of Different EDTA Concentrations on the Antibacterial Activity of OBPgpLYS and PKOBPgpLYS To determine the influence of EDTA on the antibacterial activity of unmodified and modified endolysins the antibacterial activity of the unmodified OBPgpLYS endolysin (SEQ ID NO: 47) and the PKOBPgpLYS endolysin (SEQ ID NO: 49) was tested on *Pseudomonas aeruginosa* PAO1p cells (Pirnay J P et al. *J Clin Microbiol.*, 41(3):1192-1202 (2003)) using different concentrations of EDTA and endolysins. Exponential growing bacterial cells (OD$_{600\ nm}$ of 0.6) were 100-fold diluted to a final density of about $10^6$ cells/ml and incubated for 30 minutes at room temperature without shaking with unmodified endolysin OBPgpLYS (SEQ ID NO: 47) and modified endolysin PKOBPgpLYS (SEQ ID NO: 49). For incubation, the endolysins were used each in buffer (20 mM NaH$_2$PO$_4$-NaOH pH7.4; 0.5 M NaCl; 0.5 M imidazole) at final concentrations of endolysin of 0.013 µM, 0.131 µM and 1.315 µM. Thereby, the following different EDTA concentrations were used: 0 mM, 0.05 mM, 0.5 mM and 10 mM. As a control one sample was also incubated for 30 minutes with no endolysin, instead of there was buffer (20 mM NaH$_2$PO$_4$-NaOH pH7.4; 0.5 M NaCl; 0.5 M imidazole) added. After incubation cell suspensions were diluted three times (respectively $10^5$-$10^4$-$10^3$ cells/ml) and 100 µl of each dilution was plated out on LB-medium. The residual colonies were counted after an overnight incubation at 37° C. Based on the counted cell numbers the antibacterial activity as the relative inactivation in logarithmic units (=$\log_{10} N_0/N_i$ with $N_0$=number of untreated cells and $N_i$=number of treated cells, both counted after incubation) was calculated (Table 4). All samples were replicated in threefold. Averages +/− standard deviations are represented. The maximal reduction observed (5.69 log units) is dependent on the detection level of 10 cells/ml and the initial cell density. "Δ" gives the difference of activity between the respective OBPgpLYS and PKOBPgpLYS samples.

TABLE 4

Antibacterial activity of unmodified endolysin (OBPgpLYS) and its modified endolysin variant (PKOBPgpLYS) in combination with different EDTA-Na$_2$ concentrations on exponential growing *Pseudomonas aeruginosa* PAO1p cells in logarithmic units
Concentration of EDTA-Na$_2$ (in mM)

|  | 0 | 0.05 | 0.5 | 10 |
|---|---|---|---|---|
| No endolysin | / | 0.028 +/− 0.008 | 0.130 +/− 0.023 | 1.827 +/− 0.052 |
| 0.013 µM OBPgpLYS | 0.956 +/− 0.110 | / | 4.626 +/− 0.287 | / |
| 0.013 µM PKOBPgpLYS | 0.992 +/− 0.181 | / | 5.204 +/− 0.000 | / |
| Δ | 0.036 | | 0.578 | |
| 0.131 µM OBPgpLYS | 2.158 +/− 0.027 | / | 4.599 +/− 0.275 | / |
| 0.131 µM PKOBPgpLYS | 2.529 +/− 0.184 | / | 5.671 +/− 0.000 | / |
| Δ | 0.371 | | 1.072 | |
| 1.315 µM OBPgpLYS | 2.531 +/− 0.173 | 2.762 +/− 0.091 | 4.357 +/− 1.857 | 4.888 +/− 0.275 |
| 1.315 µM PKOBPgpLYS | 3.079 +/− 0.015 | 4.145 +/− 0.015 | >5.687 | >5.687 |
| Δ | 0.548 | 1.383 | >1.330 | >0.799 |

As shown in Table 4 unmodified endolysin OBPgpLYS reduces cell numbers significantly with more than 2.5 log units for 1.315 µM and with +/−1 log unit for 0.013 µM, compared to the negative control. Modified endolysin PKOBPgpLYS results in an added 0.5 log units reduction for exponentially growing PAO1p cells. The observed antibacterial effect can be increased to more as 5.69 log units reduction (beneath the detection level) by combining PKOBPgpLYS with the outer membrane permeabilizer EDTA-Na$_2$ at a concentration of 0.5 and 10 mM EDTA. The difference in activity between the unmodified OBPgpLYS and the PK-modified OBPgpLYS increases by raising the amount of added endolysin (from 0.013-1.315 µM endolysin).

EXAMPLE 3

Cloning, Expression and Purification of an OBPgpLYS Derivative Modified with Various Peptide Stretches on the N-Terminus of the Endolysin The OBPgpLYS derivative according to SEQ ID NO:86 is a modular endolysin originating from *Pseudomonas putida* phage OBP with an N-terminal peptidoglycan binding and C-terminal catalytic domain. The OBPgpLYS derivative is encoded by the nucleic acid molecule according to SEQ ID NO: 101. Purified Plasmid DNA (see Example 1) was used to produce a nucleic acid molecule according to SEQ ID NO: 101 with a BamH I (5'-GGA TCC-3') restriction site at the 5'-end of the nucleic acid molecule and an Xho I (5'-CTC GAG-3') restriction site at the 3'-end of the nucleic acid molecule.

The following peptide stretches in table 5 were used for production of fusion proteins with the endolysin OBPgpLYS derivative. The resulting fusion proteins are also listed in table 5.

TABLE 5

Peptide stretches and their respective nucleic acid sequence for production of specific fusion proteins

| Peptide stretch | Nucleic acid molecule encoding the peptide stretch | Amino acid sequence of resulting fusion protein |
|---|---|---|
| Ascaphine (SEQ ID NO: 50) | SEQ ID NO: 90 | SEQ ID NO: 55 |
| Apidaecine (SEQ ID NO: 51) | SEQ ID NO: 91 | SEQ ID NO: 57 |
| Sarcotoxin IA (SEQ ID NO: 17) | SEQ ID NO: 92 | SEQ ID NO: 63 |
| SMAP-29 (SEQ ID NO: 12) | SEQ ID NO: 93 | SEQ ID NO: 65 |
| Cecropin A (A. aegypti) (SEQ ID NO: 15) | SEQ ID NO: 94 | SEQ ID NO: 67 |

The nucleic acid molecules encoding the respective peptide stretches were synthetically produced with a Nde I (5'-CAT ATG-3') restriction site at the 5'-end of the nucleic acid molecule and a BamH I (5'-GGA TCC-3') restriction site at the 3'-end of the nucleic acid molecule.

Fusion proteins are constructed by linking at least two nucleic acid sequences using standard cloning techniques as described e.g. by Sambrook et al. 2001, Molecular Cloning: A Laboratory Manual. Therefore the nucleic acid molecules encoding the peptide stretches were cleaved in a digest with the respective restriction enzymes Nde I and BamH I. Subsequently the cleaved nucleic acids encoding the peptide stretches were ligated into the pET21 b expression vector (Novagen, Darmstadt, Germany), which was also cleaved in a digest with the respective restriction enzymes Nde I and BamH I before.

Afterwards, the nucleic acid molecule encoding the endolysin OBPgpLYS derivative was cleaved in a digest with the restriction enzyme BamH I and Xho I, so that the endolysin could be ligated into the pET21b expression vector (Novagen, Darmstadt, Germany).

Thus, the nucleic acid molecule encoding the peptide stretch is ligated into the respective vector at the 5'-end of the nucleic acid molecule encoding the endolysin OBPgpLYS derivative. Moreover, the nucleic acid molecule encoding the endolysin OBPgpLYS derivative is ligated into the respective plasmid, so that a nucleic acid molecule encoding a His$_6$-tag consisting of six histidine residues is associated at the 3'-end of the nucleic acid molecule encoding the endolysin.

The sequence of the endolysin-peptide-fusions was controlled via DNA-sequencing and correct clones were transformed into E. coli T7 Express lysY/Iq (New England Biolabs, Frankfurt, Germany) for protein expression.

Recombinant expression of the fusion proteins according to SEQ ID NO: 55, 57, 63, 65, 67 is performed in E. coli T7 Express lysY/Iq (New England Biolabs, Frankfurt, Germany). The cells were growing until an optical density of OD600 nm of 0.5-0.8 was reached. Then the expression of the fusion protein was induced with 0.5 mM IPTG (isopropylthiogalactoside) and the expression was performed at 37° C. for a period of 4 hours.

Cells were harvested by centrifugation for 15 min at 4000 g and disrupted via sonication on ice. Soluble and insoluble fraction of the E. coli crude extract were separated by centrifugation (Sorvall, SS34, 30 min, 15000 rpm). All proteins were purified by $Ni^{2+}$ affinity chromatography (Äkta FPLC, GE Healthcare) using the C-terminal 6× His-tag, encoded by the pET21b vector.

The $Ni^{2+}$ affinity chromatography is performed in 4 subsequent steps, all at room temperature:
1. Equilibration of the Histrap FE 5 ml column (GE Healthcare) with up to 10 column volumes of Washing Buffer (20 mM imidazole, 1 M NaCl and 20 mM Hepes on pH 7.4) at a flow rate of 3-5 ml/min.
2. Loading of the total lysate (with wanted fusion protein) on the Histrap FF 5 ml column at a flow rate of 3-5 ml/min.
3. Washing of the column with up to 10 column volumes of Washing Buffer to remove unbound sample followed by a second washing step with 10% Elution buffer (500 mM imidazole, 0.5 M NaCl and 20 mM Hepes on pH 7.4) at a flow rate of 3-5 ml/min.
4. Elution of bounded fusion proteins from the column with a linear gradient of 4 column volumes of Elution Buffer (500 mM imidazole, 0.5 M NaCl and 20 mM Hepes on pH 7.4) to 100% at a flow rate of 3-5 ml/min Purified stock solutions of fusion proteins in Elution Buffer (20 mM Hepes pH 7.4; 0.5 M NaCl; 500 mM imidazole) were at least 60% pure as determined visually on SDS-PAGE gels (data not shown). .

EXAMPLE 4

Antimicrobial Activity of the Endolysin OBPgpLYS Derivative Modified with Various Peptide Stretches on the N-Terminus Acinetobacter baumannii DSMZ 30007 and Pseudomonas aeruginosa PAO1p cells (Burn wound isolate, Queen Astrid Hospital, Brussels; Pirnay JP et al. (2003), world-wide-web at ncbi.nlm.nih.gov/pubmed/12624051?ordinalpos=3&itool = EntrezSystem2.PEntrez.Pubmed.Pubmed_ResultsPanel. Pubmed_DefaultReportPanel.P ubmed_RVDocSum J Clin Microbiol., 41(3):1192-1202) were used as test strains. Overnight cultures were diluted 10-fold in fresh LB medium and grown to $OD_{600}$=0.6. The culture was spun down and diluted 10-fold in dilution buffer (10 mM HEPES, 0.5 mM EDTA; pH 7.4). Bacteria were incubated at room temperature with each 10 µg undialyzed fusion protein at a final concentration of 100 µg/ml in buffer (20 mM $NaH_2PO_4$-NaOH pH 7.4; 0.5 M NaCl; 0.5 M imidazole). After 1 hour cell dilution series were made in PBS and plated on LB. Additionally, a negative control was plated using buffer (20 mM $NaH_2PO_4$-NaOH pH 7.4; 0.5 M NaCl; 0.5 M imidazole). The residual colonies were counted after an overnight incubation at 37° C. Based on the counted cell numbers the antibacterial activity as logarithmic units (=$log_{10}N_0/N_i$ with $N_0$=number of untreated cells and $N_i$=number of treated cells) was calculated (Table 5). All samples were replicated at least in four-fold.

TABLE 6

Antimicrobial activity of the OBPgpLYS derivative modified with various peptide stretches against gram-negative bacteria

| Fusion protein | Enzyme part | Peptide stretch (N-terminal unless otherwise indicated) | Activity against Acinetobacter baumannii DSMZ 30007 | Activity against Pseudomonas aeruginosa PAO1p cells |
|---|---|---|---|---|
| SEQ ID NO: 88 | SEQ ID NO: 87 | — | ++ | + |
| SEQ ID NO: 55 | SEQ ID NO: 87 | Ascaphine (SEQ ID NO: 50) | +++ | Not determined |
| SEQ ID NO: 57 | SEQ ID NO: 87 | Apidaecine (SEQ ID NO: 51) | +++ | Not determined |
| SEQ ID NO: 63 | SEQ ID NO: 87) | Sarcotoxin IA (SEQ ID NO: 17) | +++ | ++ |
| SEQ ID NO: 65 | SEQ ID NO: 87 | SMAP-29 (SEQ ID NO:12) | +++ | ++ |
| SEQ ID NO: 67 | SEQ ID NO: 87 | Cecropin A (SEQ ID NO: 15) | +++ | +++ |

Abreviations:
+: 1 log;
++: 2-3 log;
+++: 4 or more logs;
not determined means that this strain was not tested with the respective fusion protein.

The fusion proteins in Table 6 without any tag and linker were also tested with the activity assays described above. They all showed antimicrobial activity against the used bacterial strains in Table 6.

EXAMPLE 5

N-Terminal Antibacterial Peptide Fusion to Endolysin of Pseudomonas putida Phage OBP OBPgpLys derivative, the modular endolysin of P. putida phage OBP, was N-terminally fused to a set of natural antibacterial peptide tags (Table 7) in order to investigate its anti Gram-negative activity.

vitrogen, Carlsbad, Calif., USA) by following the TA cloning protocol of the manufacturer. Pure plasmid was cutted once in

TABLE 7

List of antibacterial peptide tags which were fused to the OBPgpLYS derivative

| Tag | Description + size | Amino acid sequence | Nucleic acid sequence | Reference |
| --- | --- | --- | --- | --- |
| α4-helix of T4-lysozyme | Amphipathic helix (13 aa) | PNRAKRVITTFRT (SEQ ID NO: 68) | SEQ ID NO: 95 | Matthews et al., 1974* |
| Pentapeptide (designed) | Hydrophobic (5 aa) | FFVAP (SEQ ID NO: 18) | SEQ ID NO: 96 | Briers Y (not published) |
| Artilysin 1 (designed) | Hydrophobic (18 aa) | GFFIPAVILPSIAFLIVP (SEQ ID NO: 70) | SEQ ID NO: 97 | Walmagh, M. (Not published) |
| Artilysin 2 (designed) | Amphipathic helix (25 aa) | GKPGWLIKKALVFKKLIRRPLKRLAS (SEQ ID NO: 71) | SEQ ID NO: 98 | Walmagh, M (Not published) |
| Parasin 1 | Alpha-helical peptide (19 aa) | KGRGKQGGKVRAKAKTRSS (SEQ ID NO: 72) | SEQ ID NO: 99 | Park, Y et al., 1998** |
| Lycotoxin 1 | Amphiphatic helix (25 aa) | IWLTALKFLGKHAAKKLAKQQLSKLS (SEQ ID NO: 73) | SEQ ID NO: 100 | Yan & Adams, 1988*** |

*Matthews, B. W. and Remington, S. J. (1974). The three dimensional structure of the lysozyme from bacteriophage T4. Proc. Natl. Acad. Sci. USA, 71: 4178-4182
**In Yup Park, Chan Bae Park, Mi Sun Kim, Sun Chang Kim (1998). Parasin I, an antimicrobial peptide derived from histone H2A in the catfish, Parasilurus asotus. FEBS Letters 437 258-262
***Yan, L and Adams, M. A. (1998). Lycotoxins, Antimicrobial Peptides from Venom of the Wolf Spider, Lycosa carolinensis J. Biol. Chem, 273: 2059-2066.

Methodology of Tag Modification of the OBPgpLys Derivative

Except for the pentapeptide tag, all antibacterial peptide tags were fused to the ORF which encodes for the OBPgpLYS derivative using an adapted version of the Ligation Independent Cloning (LIC) as e.g. described in Berrow et al. 2007. Here fore, an unique Ecl136II restriction site was inserted in front of the WT endolysin gene by a tail PCR with a specific designed 5' primer (5'-GGAATGGGGAGCTCCTC-CAAAAATAGCGAGAAG-3'; SEQ ID NO:102) and the standard OBPgpLys derivative reverse primer (5'-AACTAT-TCCGTGTGCTTTCTTTGT-3'; SEQ ID NO:103) on pure genomic DNA of phage OBP. This extended fragment was then ligated in the pEXPSCT/TOPO® expression vector (Invitrogen, Carlsbad, Calif., USA) by following the TA cloning protocol of the manufacturer. Pure plasmid was cutted once in an Ecl136II restriction digest and hybridized peptide cassettes (created by hybridization of primer pairs, see Table 8) were inserted into the cutted plasmid without a necessary ligation step (LIC). For the N-terminal pentapeptide tag fusion a tail PCR with an extended 5' primer which encodes for this pentapeptide (5'-ATGGGATCCTTCTTCGTAGCA CCGGGCTCCTCCAAAAATAGCGAGAAG-3'; SEQ ID NO:104) and the standard OBPgpLys derivative reverse primer (5'-AACTATTCCGTGTGCTTTCTTTGT-3'; SEQ ID NO:103) was applied on phage OBP genomic DNA. Correct insertion of the fragments in the expression vector was verified by sequencing analysis before introducing the construct into a suitable Escherichia coli BL21(DE3)pLysS expression strain.

TABLE 8

Used primer pairs for hybridization of antibacterial peptide tags to ORF encoding the OBPgpLys derivative

| Tag | forward primer | reverse primer |
| --- | --- | --- |
| α4-helix of T4-lysozyme | 5'TTGGAATGGGGAGCCCGAACCGTGCAAAACG TGTAATCA 3'; SEQ ID NO: 105 | 5'TATTTTTGGAGGAGCCGGTACGGAAGGTGGTGAT TACACGTT 3'; SEQ ID NO: 106 |
| Artilysin 1 (designed) | 5'TTATGGGCTTCTTCATCCCGGCAGTAATCCTGC CCTCCA 3'; SEQ ID NO: 107 | 5'TATTTTTGGATCTGCCGCCCGGTACGATCAGGAAT GCGATGGAGGGCAGGATT 3'; SEQ ID NO: 108 |
| Artilysin 2 (designed) | 5'TTATGGGCAAACCGGGCTGGCTGATCAAAAG GCACTGGTATTCAAGA 3'; SEQ ID NO: 109 | 5'TATTTTTGGATCTGCCGCCTGCCAGTCTCTTCAGC GGACGACGGATCAGTTTCTTGAATACCAG 3'; SEQ ID NO: 110 |

TABLE 8-continued

Used primer pairs for hybridization of antibacterial peptide tags to ORF encoding the OBPgpLys derivative

| Tag | forward primer | reverse primer |
| --- | --- | --- |
| Parasin 1 | 5'TTGGAATGGGGAGCAAAGGCCGTGGCAAGCA GGGAGGCAAAGTACGTG 3'; SEQ ID NO: 111 | 5'TATTTTTGGAGGAGCCTGAGGAACGGGTCTTTGCT TTTGCACGTACTTTGC 3'; SEQ ID NO: 112 |
| Lycotoxin 1 | 5'GGAATGGGGAGCATCTGGCTGACCGCACTGA AATTCCTCGGCAAACACGCCGCAA 3'; SEQ ID NO: 113 | 5'TATTTTTGGAGGAGCCCAGTTTGGATAATTGCTGT TTTGCCAGTTTCTTTGCGGCGTGTT 3'; SEQ ID NO: 114 |

Large Scale Recombinant Expression of Modified OBPg-pLYS Derivative Fusion Variants Standard expression is performed in Lysogeny Broth (LB) in exponentially growing cells (OD600 nm=0.6) induced with 1 mM isopropyl-beta-D-thiogalactopyranoside. Expression parameters like temperature, time and expression strain varied on a protein specific basis in order to optimize the soluble expression levels of the modified endolysins (see Table 9).

For purification, cells from an expression culture (500-600 ml) are harvested (4500 rpm, 30 min, 4° C.) and resuspended in ⅟25 volumes of lysis buffer (10 mM imidazole, 20 mM NaH2PO4, 0.5 M NaCl, pH 7.4). This suspension is frozen/thawed three times prior to sonication (8×30 s, amplitude 40% on a Vibra Cell™, Sonics, Dandurry, Conn., USA) and filtered through 0.45 and 0.22 µm Durapore membrane filters (Millipore, Billerica, Mass., USA). Purification of the His-tagged fusion protein was performed by a one-step protocol employing Ni2+-affinity chromatography (HisTrap HP 1 ml column, GE Healthcare, Buckinghamshire, UK) according to the manufacturer's instructions. The Ni2+ affinity chromatography is performed in 4 subsequent steps, all on room temperature:

1. Equilibration of the Histrap HP 1 ml column (GE Healthcare) with 10 column volumes of Washing Buffer (60 mM imidazole, 0.5 mM NaCl and 20 mM NaH2P04-NaOH on pH 7.4) at a flow rate of 0.5 ml/min.

2. Loading of the total lysate (with wanted endolysin) on the Histrap HP 1 ml column at a flow rate of 0.5 ml/min.

3. Washing of the column with 15 column volumes of Washing Buffer at a flow rate of 1 ml/min.

4. Elution of bounded endolysin from the column with 10 column volumes of Elution Buffer (500 mM imidazole, 0.5 M NaCl and 20 mM NaH2P04-NaOH on pH 7.4) at a flow rate of 0.5 ml/min The wash buffer included a low imidazole concentration which varied on protein specific base to ensure higher purity of the protein (see Table 9). The total yields of recombinant proteins per liter E. coli expression culture is also shown in Table 3. The values were determined by spectrophotometric measurement of the protein concentration and the total volume of the purified stock solution at a wavelength of 280 nm. Purified stock solutions were at least 60% pure as determined visually on SDS-PAGE gels.

TABLE 9

Expression parameters and obtained protein yields per liter expression culture of N-terminal modified endolysins. RP = E. coli BL21(DE3)pLysS Codon min RP strain, RIL = E. coli BL21(DE3)pLysS Codon Plus RIL strain

| Modified endolysin | Temperature/ time | Protein Yield (in mg/l) | [imidazole] (in mM) |
| --- | --- | --- | --- |
| α4-OBPgpLys (SEQ ID NO: 75) | 16/overnight | 1.28 | 60 |
| Pentapeptide-OBPgpLys (SEQ ID NO: 77) | 16/overnight | 1.10 | 65 |
| Artilysin1-OBPgpLys (SEQ ID NO: 79) | 16/overnight | <0.1 | 50 |
| Artilysin2-OBPgpLys (SEQ ID NO: 81) | 16/overnight | 1.32 | 50 |
| Parasin1-OBPgpLys (SEQ ID NO: 83) | 16/overnight | 0.38 | 50 |
| Lycotoxin1-OBPgpLys (SEQ ID NO: 85) | 16/overnight | 1.71 | 50 |

In Vitro Antibacterial Activity and Host Range of Modified OBPgpLys Derivative Variants Exponential growing Gram-negative bacterial cells (OD600 nm=0.6) were 100-fold diluted to a final density of about 106 cells/ml and incubated for 30 minutes at room temperature without shaking with the different modified OBPgpLYS derivative variants. After incubation cell suspensions were diluted three times (respectively 105-104-103 cells/ml) and 100 µl of each dilution was plated out on LB-medium. The residual colonies were counted after an overnight incubation on 37° C. Based on the counted cell numbers the antibacterial activity as the relative inactivation in logarithmic units (=log $10 N_0/N_i$, with $N_0$=number of untreated cells and $N_i$=number of treated cells, both counted after incubation) is calculated (Table 10). All samples were replicated in threefold. Averages +/− standard deviations are represented.

TABLE 10

In vitro antibacterial activity of different modified OBPgpLYS derivative variants on a range of exponential growing Gram-negative species with 0.5 mM EDTA. Initial density is $10^6$ cells/ml and incubation proceeds for 30 minutes without shaking at RT. Protein concentration is 1500 nM, except for Artilys1-OBPgplys (800 nM).

| | P. aeruginosa PAO1p | P. putida G1 | E. coli X1-1 | Salmonella typhimurium LT2 |
|---|---|---|---|---|
| 1500 nM α4-OBPgpLys (SEQ ID NO: 75) | ++ | ++ | ++ | + |
| 1500 nM Pentapeptide-OBPgpLys (SEQ ID NO: 77) | ++ | +++ | ++ | + |
| 800 nM Artilysin1-OBPgpLys (SEQ ID NO: 79) | Not determined | ++ | + | + |
| 1500 nM Artilysin2-OBPgpLys (SEQ ID NO: 81) | ++ | ++ | ++ | + |
| 1500 nM Parasin2-OBPgpLys (SEQ ID NO: 83) | +++ | +++ | +++ | ++ |
| 1500 nM Lycotoxin1-OBPgpLys (SEQ ID NO: 85) | ++ | +++ | ++ | + |
| 1500 nM OBPgpLYS (SEQ ID NO: 88) | + | + | + | + |

Abreviations: +: about 0.5 log; ++: 1-2 log; +++: 3-4 or more logs; not determined means that this strain was not tested with the respective fusion protein.

---

The invention claimed is:

1. A fusion polypeptide comprising (i) the amino acid sequence of SEQ ID NO: 1, or a fragment thereof, wherein the fragment comprises an amino acid sequence selected from the group consisting of SEQ ID NO: 4 and 5, or comprises the amino acid sequences of SEQ ID NO: 4 and 5, and (ii) a heterologous polypeptide.

2. The fusion polypeptide according to claim 1, further comprising a tag.

3. The fusion polypeptide according to claim 2, wherein said fusion polypeptide comprises the amino acid sequence of SEQ ID NO: 47.

4. A fusion protein comprising (i) a polypeptide comprising the amino acid sequence of SEQ ID NO: 1, or a fragment thereof, wherein the fragment comprises an amino acid sequence selected from the group consisting of SEQ ID NO: 4 and 5, or comprises the amino acid sequences of SEQ ID NO: 4 and 5, and (ii) a heterologous peptide fused to said polypeptide at the N- or C-terminus, wherein said heterologous peptide is a cationic peptide, polycationic peptide, amphipathic peptide, sushi peptide, defensin, hydrophobic peptide and/or an antimicrobial peptide.

5. The fusion protein according to claim 4, wherein said heterologous peptide comprises 5 to 100 amino acid residues.

6. The fusion protein according to claim 4, wherein said cationic and/or polycationic peptide comprises at least one amino acid residue selected from the group consisting of arginine, histidine and lysine residues.

7. The fusion protein according to claim 4, wherein the amphipathic peptide comprises at least one positively charged amino acid residue selected from the group consisting of lysine, arginine and histidine residues, combined to at least one hydrophobic amino acid residue selected from the group consisting of valine, isoleucine, leucine, methionine, phenylalanine, tryptophan, cysteine, alanine, tyrosine, histidine, threonine, serine, proline and glycine residues.

8. The fusion protein according to claim 4, wherein the heterologous peptide comprises an amino acid sequence selected from the group consisting SEQ ID NO: 19-39 and KRK.

9. The fusion protein according to claim 4, wherein said fusion protein comprises an amino acid sequence selected from the group consisting SEQ ID NO: 43 and 49.

10. A pharmaceutical or cosmetic composition comprising the fusion polypeptide according to claim 1.

11. A pharmaceutical or cosmetic composition comprising the fusion protein of claim 4.

12. The fusion polypeptide according to claim 2, wherein the tag comprises a His$_6$-tag.

13. The fusion protein according to claim 5, wherein said heterologous peptide comprises 5 to 50 amino acid residues.

14. The fusion protein according to claim 13, wherein said heterologous peptide comprises 5 to 30 amino acid residues.

15. The fusion protein according to claim 6, wherein at least 70% of the amino acid residues comprised in said heterologous peptide are arginine, histidine and/or lysine residues.

16. The fusion protein according to claim 15, wherein at least 70% of the amino acid residues comprised in said heterologous peptide are arginine and/or lysine residues.

17. The fusion protein according to claim 7, wherein at least 70% of the amino acid residues in said amphipathic peptide are either arginine or lysine residues and at least 30% of the amino acid residues in said amphipathic peptide are valine, isoleucine, leucine, methionine, phenylalanine, tryptophan, cysteine, alanine, tyrosine, histidine, threonine, serine, proline or glycine residues.

18. The fusion protein according to claim 4, wherein the heterologous peptide comprises an amino acid sequence selected from the group consisting of SEQ ID NO: 6, 8, 10, 11, and 15.

19. The fusion protein according to claim 4, wherein the heterologous peptide comprises the amino acid sequence of SEQ ID NO: 14.

20. The fusion protein according to claim 4, wherein the heterologous peptide comprises an amino acid sequence selected from the group consisting of SEQ ID NO: 7, 9, 12, 16, and 17.

21. The fusion protein according to claim 4, wherein the heterologous peptide comprises the amino acid sequence of SEQ ID NO: 13.

22. The fusion protein according to claim 4, wherein the heterologous peptide comprises the amino acid sequence of SEQ ID NO: 18.

23. A fusion polypeptide comprising (i) the amino acid sequence of SEQ ID NO: 86 or 87 and (ii) a heterologous polypeptide.

24. A fusion protein comprising (i) a polypeptide comprising the amino acid sequence of SEQ ID NO: 86 or 87, and (ii) a heterologous peptide fused to said polypeptide at the N- or C-terminus, wherein said heterologous peptide is a cationic peptide, polycationic peptide, amphipathic peptide, sushi peptide, defensin, hydrophobic peptide and/or an antimicrobial peptide.

* * * * *

SEQUENCE LISTING

```
<160> NUMBER OF SEQ ID NOS: 119

<210> SEQ ID NO 1
<211> LENGTH: 328
<212> TYPE: PRT
<213> ORGANISM: unknown
<220> FEATURE:
<223> OTHER INFORMATION: OBPgpLYS

<400> SEQUENCE: 1

Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Lys His Met
        115                 120                 125

Ser Ile Glu Gln Leu Arg Ala Met Leu Pro Thr Asp Arg Gln Gly Tyr
    130                 135                 140

Ala Glu Val Tyr Ile Asp Pro Leu Asn Glu Thr Met Asp Ile Phe Glu
```

```
                145                 150                 155                 160
        Ile Asn Thr Pro Leu Arg Ile Ala His Phe Met Ala Gln Ile Leu His
                        165                 170                 175

Glu Thr Ala Cys Phe Lys Tyr Thr Glu Glu Leu Ala Ser Gly Lys Ala
                        180                 185                 190

Tyr Glu Gly Arg Ala Asp Leu Gly Asn Thr Arg Pro Gly Asp Gly Pro
                        195                 200                 205

Leu Phe Lys Gly Arg Gly Leu Leu Gln Ile Thr Gly Arg Leu Asn Tyr
                        210                 215                 220

Val Lys Cys Gln Val Tyr Leu Arg Glu Lys Leu Lys Asp Pro Thr Phe
        225                 230                 235                 240

Asp Ile Thr Ser Ser Val Thr Cys Ala Gln Gln Leu Ser Glu Ser Pro
                        245                 250                 255

Leu Leu Ala Ala Leu Ala Ser Gly Tyr Phe Trp Arg Phe Ile Lys Pro
                        260                 265                 270

Lys Leu Asn Glu Thr Ala Asp Lys Asp Ile Tyr Trp Val Ser Val
                        275                 280                 285

Tyr Val Asn Gly Tyr Ala Lys Gln Ala Asn Pro Tyr Tyr Pro Asn Arg
                        290                 295                 300

Asp Lys Glu Pro Asn His Met Lys Glu Arg Val Gln Met Leu Ala Val
        305                 310                 315                 320

Thr Lys Lys Ala Leu Gly Ile Val
                        325

<210> SEQ ID NO 2
<211> LENGTH: 987
<212> TYPE: DNA
<213> ORGANISM: Bacteriophage OBP

<400> SEQUENCE: 2
atgaaaaata gcgagaagaa tgcatcgata attatgtcga tacagagaac gctcgcttca        60
ctctcactct atggaggccg catcgacggc ctctttggag agaagtgtcg tggggctatc       120
atcttgatgc tgaataaggt ctatcctaat ttcagcacca acaaacttcc gagtaacaca       180
tatgaagcgg aatccgtgtt cacgtttctc cagactgctt tggctggtgt tggtctttat       240
accattacta ttgatggtaa atggggtggt acttctcaag gtgctattga cgccctcgtc       300
aagtcttacc gtcaaattac cgaagcggag cgagctgggt cgacgttgcc attaggtctt       360
gctactgtga tgtctaagca tatgtctatt gaacagttga gagcaatgct ccctaccgat       420
agacaaggat atgctgaagt ttatatcgat cctttaaatg agacgatgga tatatttgaa       480
ataaatactc cattacgaat tgctcatttc atggcccaaa tcctccacga aacggcgtgt       540
tttaaatata ccgaagaact ggcgagcggt aaggcttatg agggtcgtgc tgatttaggt       600
aatactcgac caggtgatgg accactgttt aaaggtcgtg gattattaca aattaccggg       660
cgactgaatt atgtgaaatg ccaagtgtat ttgagagaga agttaaagga ccctactttc       720
gacattacgt cgtctgtaac ttgtgcccaa cagctctccg aaagtccact tcttgctgca       780
ttggcatcgg gctacttctg gagattcatc aaacctaaac tcaatgaaac ggctgataaa       840
gacgatatct attgggtttc tgtttatgtc aatggttacg ctaaacaagc gaatccttat       900
taccctaacc gggataagga acccaaccat atgaaagaac gtgtccaaat gcttgcagtg       960
acaaagaaag cactcggaat agtttaa                                           987

<210> SEQ ID NO 3
```

<211> LENGTH: 984
<212> TYPE: DNA
<213> ORGANISM: unknown
<220> FEATURE:
<223> OTHER INFORMATION: OBPgpLYS

<400> SEQUENCE: 3

```
atgaaaaata gcgagaagaa tgcatcgata attatgtcga tacagagaac gctcgcttca    60
ctctcactct atggaggccg catcgacggc ctctttggag agaagtgtcg tgggctatc    120
atcttgatgc tgaataaggt ctatcctaat ttcagcacca acaaacttcc gagtaacaca    180
tatgaagcgg aatccgtgtt cacgtttctc cagactgctt tggctggtgt tggtctttat    240
accattacta ttgatggtaa atggggtggt acttctcaag gtgctattga cgccctcgtc    300
aagtcttacc gtcaaattac cgaagcgag cgagctgggt cgacgttgcc attaggtctt    360
gctactgtga tgtctaagca tatgtctatt gaacagttga gagcaatgct ccctaccgat    420
agacaaggat atgctgaagt ttatatcgat cctttaaatg agacgatgga tatatttgaa    480
ataaatactc cattacgaat tgctcatttc atggcccaaa tcctccacga aacggcgtgt    540
tttaaatata ccgaagaact ggcgagcggt aaggcttatg agggtcgtgc tgatttaggt    600
aatactcgac aggtgatgg accactgttt aaaggtcgtg gattattaca aattaccggg    660
cgactgaatt atgtgaaatg ccaagtgtat ttgagagaga agttaaagga ccctactttc    720
gacattacgt cgtctgtaac ttgtgcccaa cagctctccg aaagtccact tcttgctgca    780
ttggcatcgg gctacttctg agagattcatc aaacctaaac tcaatgaaac ggctgataaa    840
gacgatatct attgggtttc tgtttatgtc aatggttacg ctaaacaagc gaatccttat    900
taccctaacc gggataagga acccaaccat atgaaagaac gtgtccaaat gcttgcagtg    960
acaaagaaag cactcggaat agtt                                            984
```

<210> SEQ ID NO 4
<211> LENGTH: 90
<212> TYPE: PRT
<213> ORGANISM: unknown
<220> FEATURE:
<223> OTHER INFORMATION: PGB of OBPgpLYS

<400> SEQUENCE: 4

```
Asn Ala Ser Ile Ile Met Ser Ile Gln Arg Thr Leu Ala Ser Leu Ser
1               5                   10                  15

Leu Tyr Gly Gly Arg Ile Asp Gly Leu Phe Gly Glu Lys Cys Arg Gly
                20                  25                  30

Ala Ile Ile Leu Met Leu Asn Lys Val Tyr Pro Asn Phe Ser Thr Asn
            35                  40                  45

Lys Leu Pro Ser Asn Thr Tyr Glu Ala Glu Ser Val Phe Thr Phe Leu
        50                  55                  60

Gln Thr Ala Leu Ala Gly Val Gly Leu Tyr Thr Ile Thr Ile Asp Gly
65                  70                  75                  80

Lys Trp Gly Gly Thr Ser Gln Gly Ala Ile
                85                  90
```

<210> SEQ ID NO 5
<211> LENGTH: 167
<212> TYPE: PRT
<213> ORGANISM: unknown
<220> FEATURE:
<223> OTHER INFORMATION: EAD of OBPgpLYS

<400> SEQUENCE: 5

Lys His Met Ser Ile Glu Gln Leu Arg Ala Met Leu Pro Thr Asp Arg
1               5                   10                  15

Gln Gly Tyr Ala Glu Val Tyr Ile Asp Pro Leu Asn Glu Thr Met Asp
            20                  25                  30

Ile Phe Glu Ile Asn Thr Pro Leu Arg Ile Ala His Phe Met Ala Gln
        35                  40                  45

Ile Leu His Glu Thr Ala Cys Phe Lys Tyr Thr Glu Glu Leu Ala Ser
    50                  55                  60

Gly Lys Ala Tyr Glu Gly Arg Ala Asp Leu Gly Asn Thr Arg Pro Gly
65              70                  75                  80

Asp Gly Pro Leu Phe Lys Gly Arg Gly Leu Leu Gln Ile Thr Gly Arg
                85                  90                  95

Leu Asn Tyr Val Lys Cys Gln Val Tyr Leu Arg Glu Lys Leu Lys Asp
                100                 105                 110

Pro Thr Phe Asp Ile Thr Ser Ser Val Thr Cys Ala Gln Gln Leu Ser
            115                 120                 125

Glu Ser Pro Leu Leu Ala Ala Leu Ala Ser Gly Tyr Phe Trp Arg Phe
        130                 135                 140

Ile Lys Pro Lys Leu Asn Glu Thr Ala Asp Lys Asp Ile Tyr Trp
145                 150                 155                 160

Val Ser Val Tyr Val Asn Gly
                165

<210> SEQ ID NO 6
<211> LENGTH: 25
<212> TYPE: PRT
<213> ORGANISM: unknown
<220> FEATURE:
<223> OTHER INFORMATION: amphiphatic peptide Pleurocidin

<400> SEQUENCE: 6

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 7
<211> LENGTH: 31
<212> TYPE: PRT
<213> ORGANISM: unknown
<220> FEATURE:
<223> OTHER INFORMATION: amphiphatic peptide Cecropin P1

<400> SEQUENCE: 7

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 8
<211> LENGTH: 21
<212> TYPE: PRT
<213> ORGANISM: unknown
<220> FEATURE:
<223> OTHER INFORMATION: amphiphatic peptide Buforin II

<400> SEQUENCE: 8

Thr Arg Ser Ser Arg Ala Gly Leu Gln Phe Pro Val Gly Arg Val His
1               5                   10                  15

Arg Leu Leu Arg Lys
        20

<210> SEQ ID NO 9
<211> LENGTH: 39
<212> TYPE: PRT
<213> ORGANISM: unknown
<220> FEATURE:
<223> OTHER INFORMATION: amphiphatic peptide Buforin I

<400> SEQUENCE: 9

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 10
<211> LENGTH: 23
<212> TYPE: PRT
<213> ORGANISM: unknown
<220> FEATURE:
<223> OTHER INFORMATION: amphiphatic peptide Magainin

<400> SEQUENCE: 10

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 11
<211> LENGTH: 37
<212> TYPE: PRT
<213> ORGANISM: unknown
<220> FEATURE:
<223> OTHER INFORMATION: amphiphatic peptide LL-37

<400> SEQUENCE: 11

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 12
<211> LENGTH: 29
<212> TYPE: PRT
<213> ORGANISM: unknown
<220> FEATURE:
<223> OTHER INFORMATION: antimicrobial peptide SMAP-29

<400> SEQUENCE: 12

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 13
<211> LENGTH: 13
<212> TYPE: PRT
<213> ORGANISM: unknown
<220> FEATURE:

<223> OTHER INFORMATION: antimicrobial peptide Indolicidin

<400> SEQUENCE: 13

Ile Leu Pro Trp Lys Trp Pro Trp Trp Pro Trp Arg Arg
1               5                   10

<210> SEQ ID NO 14
<211> LENGTH: 18
<212> TYPE: PRT
<213> ORGANISM: unknown
<220> FEATURE:
<223> OTHER INFORMATION: antimicrobial peptide Protegrin

<400> SEQUENCE: 14

Arg Gly Gly Arg Leu Cys Tyr Cys Arg Arg Arg Phe Cys Val Cys Val
1               5                   10                  15

Gly Arg

<210> SEQ ID NO 15
<211> LENGTH: 36
<212> TYPE: PRT
<213> ORGANISM: unknown
<220> FEATURE:
<223> OTHER INFORMATION: antimicrobial peptide Cecropin A (A.aegypti)

<400> SEQUENCE: 15

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35

<210> SEQ ID NO 16
<211> LENGTH: 40
<212> TYPE: PRT
<213> ORGANISM: unknown
<220> FEATURE:
<223> OTHER INFORMATION: antimicrobial peptide Cecropin A (D. melanogaster)

<400> SEQUENCE: 16

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala
            20                  25                  30

Asn Val Ala Ala Thr Ala Arg Gly
        35                  40

<210> SEQ ID NO 17
<211> LENGTH: 39
<212> TYPE: PRT
<213> ORGANISM: unknown
<220> FEATURE:
<223> OTHER INFORMATION: antimicrobial peptide Sarcotoxin IA

<400> SEQUENCE: 17

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
        35

```
<210> SEQ ID NO 18
<211> LENGTH: 5
<212> TYPE: PRT
<213> ORGANISM: unknown
<220> FEATURE:
<223> OTHER INFORMATION: synthetic peptide

<400> SEQUENCE: 18

Phe Phe Val Ala Pro
1               5

<210> SEQ ID NO 19
<211> LENGTH: 6
<212> TYPE: PRT
<213> ORGANISM: unknown
<220> FEATURE:
<223> OTHER INFORMATION: synthetic peptide

<400> SEQUENCE: 19

Lys Arg Lys Lys Arg Lys
1               5

<210> SEQ ID NO 20
<211> LENGTH: 9
<212> TYPE: PRT
<213> ORGANISM: unknown
<220> FEATURE:
<223> OTHER INFORMATION: synthetic peptide

<400> SEQUENCE: 20

Lys Arg Lys Lys Arg Lys Lys Arg Lys
1               5

<210> SEQ ID NO 21
<211> LENGTH: 9
<212> TYPE: PRT
<213> ORGANISM: unknown
<220> FEATURE:
<223> OTHER INFORMATION: synthetic peptide

<400> SEQUENCE: 21

Arg Arg Arg Arg Arg Arg Arg Arg Arg
1               5

<210> SEQ ID NO 22
<211> LENGTH: 8
<212> TYPE: PRT
<213> ORGANISM: unknown
<220> FEATURE:
<223> OTHER INFORMATION: synthetic peptide

<400> SEQUENCE: 22

Lys Lys Lys Lys Lys Lys Lys Lys
1               5

<210> SEQ ID NO 23
<211> LENGTH: 10
<212> TYPE: PRT
<213> ORGANISM: unknown
<220> FEATURE:
<223> OTHER INFORMATION: synthetic peptide

<400> SEQUENCE: 23

Lys Arg Lys Lys Arg Lys Lys Arg Lys Lys
1               5                   10
```

<210> SEQ ID NO 24
<211> LENGTH: 12
<212> TYPE: PRT
<213> ORGANISM: unknown
<220> FEATURE:
<223> OTHER INFORMATION: synthetic peptide

<400> SEQUENCE: 24

Lys Arg Lys Lys Arg Lys Lys Arg Lys Lys Arg Lys
1               5                   10

<210> SEQ ID NO 25
<211> LENGTH: 14
<212> TYPE: PRT
<213> ORGANISM: unknown
<220> FEATURE:
<223> OTHER INFORMATION: synthetic peptide

<400> SEQUENCE: 25

Lys Arg Lys Lys Arg Lys Lys Arg Lys Lys Arg Lys Lys Arg
1               5                   10

<210> SEQ ID NO 26
<211> LENGTH: 16
<212> TYPE: PRT
<213> ORGANISM: unknown
<220> FEATURE:
<223> OTHER INFORMATION: synthetic peptide

<400> SEQUENCE: 26

Lys Lys Lys Lys Lys Lys Lys Lys Lys Lys Lys Lys Lys Lys Lys Lys
1               5                   10                  15

<210> SEQ ID NO 27
<211> LENGTH: 19
<212> TYPE: PRT
<213> ORGANISM: unknown
<220> FEATURE:
<223> OTHER INFORMATION: synthetic peptide

<400> SEQUENCE: 27

Lys Arg Lys Lys Arg Lys Lys Arg Lys Lys Arg Lys Lys Arg Lys Lys
1               5                   10                  15

Arg Lys Lys

<210> SEQ ID NO 28
<211> LENGTH: 19
<212> TYPE: PRT
<213> ORGANISM: unknown
<220> FEATURE:
<223> OTHER INFORMATION: synthetic peptide

<400> SEQUENCE: 28

Arg Arg Arg Arg Arg Arg Arg Arg Arg Arg Arg Arg Arg Arg Arg Arg
1               5                   10                  15

Arg Arg Arg

<210> SEQ ID NO 29
<211> LENGTH: 19
<212> TYPE: PRT
<213> ORGANISM: unknown
<220> FEATURE:
<223> OTHER INFORMATION: synthetic peptide

<400> SEQUENCE: 29

```
Lys Lys Lys Lys Lys Lys Lys Lys Lys Lys Lys Lys Lys Lys Lys
1               5                   10                  15

Lys Lys Lys

<210> SEQ ID NO 30
<211> LENGTH: 20
<212> TYPE: PRT
<213> ORGANISM: unknown
<220> FEATURE:
<223> OTHER INFORMATION: synthetic peptide

<400> SEQUENCE: 30

Lys Arg Lys Lys Arg Lys Lys Arg Lys Arg Ser Lys Arg Lys Lys Arg
1               5                   10                  15

Lys Lys Arg Lys
            20

<210> SEQ ID NO 31
<211> LENGTH: 21
<212> TYPE: PRT
<213> ORGANISM: unknown
<220> FEATURE:
<223> OTHER INFORMATION: synthetic peptide

<400> SEQUENCE: 31

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 32
<211> LENGTH: 21
<212> TYPE: PRT
<213> ORGANISM: unknown
<220> FEATURE:
<223> OTHER INFORMATION: synthetic peptide

<400> SEQUENCE: 32

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 33
<211> LENGTH: 22
<212> TYPE: PRT
<213> ORGANISM: unknown
<220> FEATURE:
<223> OTHER INFORMATION: synthetic peptide

<400> SEQUENCE: 33

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 34
<211> LENGTH: 24
<212> TYPE: PRT
<213> ORGANISM: unknown
<220> FEATURE:
<223> OTHER INFORMATION: synthetic peptide

<400> SEQUENCE: 34
```

```
Lys Arg Lys Lys Arg Lys Lys Arg Lys Gly Ser Gly Ser Gly Lys
1               5                   10                  15

Arg Lys Lys Arg Lys Lys Arg Lys
            20
```

<210> SEQ ID NO 35
<211> LENGTH: 25
<212> TYPE: PRT
<213> ORGANISM: unknown
<220> FEATURE:
<223> OTHER INFORMATION: synthetic peptide

<400> SEQUENCE: 35

```
Lys Arg Lys Lys Arg Lys Lys Arg Lys Lys Arg Lys Lys Arg Lys
1               5                   10                  15

Arg Lys Lys Arg Lys Lys Arg Lys Lys
            20                  25
```

<210> SEQ ID NO 36
<211> LENGTH: 31
<212> TYPE: PRT
<213> ORGANISM: unknown
<220> FEATURE:
<223> OTHER INFORMATION: synthetic peptide

<400> SEQUENCE: 36

```
Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30
```

<210> SEQ ID NO 37
<211> LENGTH: 38
<212> TYPE: PRT
<213> ORGANISM: unknown
<220> FEATURE:
<223> OTHER INFORMATION: synthetic peptide

<400> SEQUENCE: 37

```
Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35
```

<210> SEQ ID NO 38
<211> LENGTH: 39
<212> TYPE: PRT
<213> ORGANISM: unknown
<220> FEATURE:
<223> OTHER INFORMATION: synthetic peptide

<400> SEQUENCE: 38

```
Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
        35
```

<210> SEQ ID NO 39
<211> LENGTH: 42

```
<212> TYPE: PRT
<213> ORGANISM: unknown
<220> FEATURE:
<223> OTHER INFORMATION: synthetic peptide

<400> SEQUENCE: 39

Lys Arg Lys Lys Arg Lys Lys Arg Lys Ser Lys Arg Lys Lys Arg
1               5                   10                  15

Lys Lys Arg Lys Arg Ser Lys Arg Lys Arg Lys Lys Arg Lys Arg
            20                  25                  30

Ser Lys Arg Lys Lys Arg Lys Lys Arg Lys
            35                  40

<210> SEQ ID NO 40
<211> LENGTH: 5
<212> TYPE: PRT
<213> ORGANISM: unknown
<220> FEATURE:
<223> OTHER INFORMATION: synthetic peptide
<220> FEATURE:
<221> NAME/KEY: misc_feature
<222> LOCATION: (3)..(3)
<223> OTHER INFORMATION: wherein Xaa is any other amino acid residue
      than lysine, arginine and histidine

<400> SEQUENCE: 40

Lys Arg Xaa Lys Arg
1               5

<210> SEQ ID NO 41
<211> LENGTH: 5
<212> TYPE: PRT
<213> ORGANISM: unknown
<220> FEATURE:
<223> OTHER INFORMATION: synthetic peptide

<400> SEQUENCE: 41

Lys Arg Ser Lys Arg
1               5

<210> SEQ ID NO 42
<211> LENGTH: 5
<212> TYPE: PRT
<213> ORGANISM: unknown
<220> FEATURE:
<223> OTHER INFORMATION: synthetic peptide

<400> SEQUENCE: 42

Lys Arg Gly Ser Gly
1               5

<210> SEQ ID NO 43
<211> LENGTH: 339
<212> TYPE: PRT
<213> ORGANISM: unknown
<220> FEATURE:
<223> OTHER INFORMATION: PKOBPgpLYS

<400> SEQUENCE: 43

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
            20                  25                  30

Ser Leu Tyr Gly Gly Arg Ile Asp Gly Leu Phe Gly Glu Lys Cys Arg
            35                  40                  45
```

Gly Ala Ile Ile Leu Met Leu Asn Lys Val Tyr Pro Asn Phe Ser Thr
 50              55                  60

Asn Lys Leu Pro Ser Asn Thr Tyr Glu Ala Glu Ser Val Phe Thr Phe
 65              70                  75                  80

Leu Gln Thr Ala Leu Ala Gly Val Gly Leu Tyr Thr Ile Thr Ile Asp
                 85                  90                  95

Gly Lys Trp Gly Gly Thr Ser Gln Gly Ala Ile Asp Ala Leu Val Lys
                100                 105                 110

Ser Tyr Arg Gln Ile Thr Glu Ala Glu Arg Ala Gly Ser Thr Leu Pro
                115                 120                 125

Leu Gly Leu Ala Thr Val Met Ser Lys His Met Ser Ile Glu Gln Leu
130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
                180                 185                 190

Lys Tyr Thr Glu Glu Leu Ala Ser Gly Lys Ala Tyr Glu Gly Arg Ala
                195                 200                 205

Asp Leu Gly Asn Thr Arg Pro Gly Asp Gly Pro Leu Phe Lys Gly Arg
210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
                260                 265                 270

Ala Ser Gly Tyr Phe Trp Arg Phe Ile Lys Pro Lys Leu Asn Glu Thr
                275                 280                 285

Ala Asp Lys Asp Asp Ile Tyr Trp Val Ser Val Tyr Val Asn Gly Tyr
                290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala Leu
                325                 330                 335

Gly Ile Val

<210> SEQ ID NO 44
<211> LENGTH: 21
<212> TYPE: DNA
<213> ORGANISM: Artificial Sequence
<220> FEATURE:
<223> OTHER INFORMATION: OBPgpLYS forward primer

<400> SEQUENCE: 44
atgaaaaata gcgagaagaa t                                          21

<210> SEQ ID NO 45
<211> LENGTH: 24
<212> TYPE: DNA
<213> ORGANISM: Artificial Sequence
<220> FEATURE:
<223> OTHER INFORMATION: OBPgpLYS reverse primer

<400> SEQUENCE: 45
aactattccg agtgctttct ttgt                                       24

```
<210> SEQ ID NO 46
<211> LENGTH: 54
<212> TYPE: DNA
<213> ORGANISM: Artificial Sequence
<220> FEATURE:
<223> OTHER INFORMATION: PKOBPgpLYS forward primer

<400> SEQUENCE: 46
atgggatcca aacgcaagaa acgtaagaaa cgcaaaaaaa atagcgagaa gaat          54

<210> SEQ ID NO 47
<211> LENGTH: 336
<212> TYPE: PRT
<213> ORGANISM: unknown
<220> FEATURE:
<223> OTHER INFORMATION: OBPgpLYS with His-tag

<400> SEQUENCE: 47
```

Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Lys His Met
        115                 120                 125

Ser Ile Glu Gln Leu Arg Ala Met Leu Pro Thr Asp Arg Gln Gly Tyr
    130                 135                 140

Ala Glu Val Tyr Ile Asp Pro Leu Asn Glu Thr Met Asp Ile Phe Glu
145                 150                 155                 160

Ile Asn Thr Pro Leu Arg Ile Ala His Phe Met Ala Gln Ile Leu His
                165                 170                 175

Glu Thr Ala Cys Phe Lys Tyr Thr Glu Glu Leu Ala Ser Gly Lys Ala
            180                 185                 190

Tyr Glu Gly Arg Ala Asp Leu Gly Asn Thr Arg Pro Gly Asp Gly Pro
        195                 200                 205

Leu Phe Lys Gly Arg Gly Leu Leu Gln Ile Thr Gly Arg Leu Asn Tyr
    210                 215                 220

Val Lys Cys Gln Val Tyr Leu Arg Glu Lys Leu Lys Asp Pro Thr Phe
225                 230                 235                 240

Asp Ile Thr Ser Ser Val Thr Cys Ala Gln Gln Leu Ser Glu Ser Pro
                245                 250                 255

Leu Leu Ala Ala Leu Ala Ser Gly Tyr Phe Trp Arg Phe Ile Lys Pro
            260                 265                 270

Lys Leu Asn Glu Thr Ala Asp Lys Asp Ile Tyr Trp Val Ser Val
        275                 280                 285

Tyr Val Asn Gly Tyr Ala Lys Gln Ala Asn Pro Tyr Tyr Pro Asn Arg
    290                 295                 300

Asp Lys Glu Pro Asn His Met Lys Glu Arg Val Gln Met Leu Ala Val
305                 310                 315                 320

Thr Lys Lys Ala Leu Gly Ile Val Lys Gly His His His His His
                325                 330                 335

<210> SEQ ID NO 48
<211> LENGTH: 1011
<212> TYPE: DNA
<213> ORGANISM: unknown
<220> FEATURE:
<223> OTHER INFORMATION: OBPgpLYS with additional His-tag

<400> SEQUENCE: 48

```
atgaaaaata gcgagaagaa tgcatcgata attatgtcga tacagagaac gctcgcttca    60
ctctcactct atggaggccg catcgacggc ctctttggag agaagtgtcg tggggctatc   120
atcttgatgc tgaataaggt ctatcctaat ttcagcacca acaaacttcc gagtaacaca   180
tatgaagcgg aatccgtgtt cacgtttctc cagactgctt tggctggtgt tggtctttat   240
accattacta ttgatggtaa atggggtggt acttctcaag gtgctattga cgccctcgtc   300
aagtcttacc gtcaaattac cgaagcggag cgagctgggt cgacgttgcc attaggtctt   360
gctactgtga tgtctaagca tatgtctatt gaacagttga gagcaatgct ccctaccgat   420
agacaaggat atgctgaagt ttatatcgat cctttaaatg agacgatgga tatatttgaa   480
ataaatactc cattacgaat tgctcatttc atggcccaaa tcctccacga acggcgtgt    540
tttaaatata ccgaagaact ggcgagcggt aaggcttatg agggtcgtgc tgatttaggt   600
aatactcgac aggtgatgg accactgttt aaaggtcgtg gattattaca aattaccggg   660
cgactgaatt atgtgaaatg ccaagtgtat ttgagagaga agttaaagga ccctactttc   720
gacattacgt cgtctgtaac ttgtgcccaa cagctctccg aaagtccact tcttgctgca   780
ttggcatcgg gctacttctg gagattcatc aaacctaaac tcaatgaaac ggctgataaa   840
gacgatatct attgggtttc tgtttatgtc aatggttacg ctaaacaagc gaatccttat   900
taccctaacc gggataagga acccaaccat atgaagaac gtgtccaaat gcttgcagtg   960
acaaagaaag cactcggaat agttaagggt catcatcacc atcaccattg a           1011
```

<210> SEQ ID NO 49
<211> LENGTH: 347
<212> TYPE: PRT
<213> ORGANISM: unknown
<220> FEATURE:
<223> OTHER INFORMATION: PKOBPgpLYS with additional His-tag

<400> SEQUENCE: 49

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
                20                  25                  30

Ser Leu Tyr Gly Gly Arg Ile Asp Gly Leu Phe Gly Glu Lys Cys Arg
            35                  40                  45

Gly Ala Ile Ile Leu Met Leu Asn Lys Val Tyr Pro Asn Phe Ser Thr
        50                  55                  60

Asn Lys Leu Pro Ser Asn Thr Tyr Glu Ala Glu Ser Val Phe Thr Phe
65                  70                  75                  80

Leu Gln Thr Ala Leu Ala Gly Val Gly Leu Tyr Thr Ile Thr Ile Asp
                85                  90                  95

Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
        115                 120                 125

Leu Gly Leu Ala Thr Val Met Ser Lys His Met Ser Ile Glu Gln Leu
    130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
            180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
    210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
            260                 265                 270

Ala Ser Gly Tyr Phe Trp Arg Phe Ile Lys Pro Lys Leu Asn Glu Thr
        275                 280                 285

Ala Asp Lys Asp Ile Tyr Trp Val Ser Val Tyr Val Asn Gly Tyr
290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala Leu
                325                 330                 335

Gly Ile Val Lys Gly His His His His His
            340                 345

<210> SEQ ID NO 50
<211> LENGTH: 24
<212> TYPE: PRT
<213> ORGANISM: unknown
<220> FEATURE:
<223> OTHER INFORMATION: antimicrobial peptide ascaphine

<400> SEQUENCE: 50

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 51
<211> LENGTH: 17
<212> TYPE: PRT
<213> ORGANISM: unknown
<220> FEATURE:
<223> OTHER INFORMATION: antimicrobial peptide apidaecine

<400> SEQUENCE: 51

Ala Asn Arg Pro Val Tyr Ile Pro Pro Pro Arg Pro Pro His Pro Arg
1               5                   10                  15

Leu

<210> SEQ ID NO 52
<211> LENGTH: 22
<212> TYPE: PRT
<213> ORGANISM: unknown
<220> FEATURE:
<223> OTHER INFORMATION: antimicrobial peptide Nigrocine

<400> SEQUENCE: 52

Gly Leu Leu Ser Lys Val Leu Gly Val Gly Lys Lys Val Leu Cys Gly
1               5                   10                  15

Val Ser Gly Leu Val Cys
            20

<210> SEQ ID NO 53
<211> LENGTH: 24
<212> TYPE: PRT
<213> ORGANISM: unknown
<220> FEATURE:
<223> OTHER INFORMATION: antimicrobial peptide Pseudin

<400> SEQUENCE: 53

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 54
<211> LENGTH: 354
<212> TYPE: PRT
<213> ORGANISM: unknown
<220> FEATURE:
<223> OTHER INFORMATION: Ascaphine5-OBPgpLYS

<400> SEQUENCE: 54

Met Gly Ile Lys Asp Trp Ile Lys Gly Ala Ala Lys Lys Leu Ile Lys
1               5                   10                  15

Thr Val Ala Ser His Ile Ala Asn Gln Gly Ser Lys Asn Ser Glu Lys
            20                  25                  30

Asn Ala Ser Ile Ile Met Ser Ile Gln Arg Thr Leu Ala Ser Leu Ser
        35                  40                  45

Leu Tyr Gly Gly Arg Ile Asp Gly Leu Phe Gly Glu Lys Cys Arg Gly
    50                  55                  60

Ala Ile Ile Leu Met Leu Asn Lys Val Tyr Pro Asn Phe Ser Thr Asn
65                  70                  75                  80

Lys Leu Pro Ser Asn Thr Tyr Glu Ala Glu Ser Val Phe Thr Phe Leu
                85                  90                  95

Gln Thr Ala Leu Ala Gly Val Gly Leu Tyr Thr Ile Thr Ile Asp Gly
            100                 105                 110

Lys Trp Gly Gly Thr Ser Gln Gly Ala Ile Asp Ala Leu Val Lys Ser
        115                 120                 125

Tyr Arg Gln Ile Thr Glu Ala Glu Arg Ala Gly Ser Thr Leu Pro Leu
    130                 135                 140

Gly Leu Ala Thr Val Met Ser Lys His Met Ser Ile Glu Gln Leu Arg
145                 150                 155                 160

Ala Met Leu Pro Thr Asp Arg Gln Gly Tyr Ala Glu Val Tyr Ile Asp
                165                 170                 175

Pro Leu Asn Glu Thr Met Asp Ile Phe Glu Ile Asn Thr Pro Leu Arg
            180                 185                 190

Ile Ala His Phe Met Ala Gln Ile Leu His Glu Thr Ala Cys Phe Lys

```
                   195                 200                 205

Tyr Thr Glu Glu Leu Ala Ser Gly Lys Ala Tyr Glu Gly Arg Ala Asp
    210                 215                 220

Leu Gly Asn Thr Arg Pro Gly Asp Pro Leu Phe Lys Gly Arg Gly
225                 230                 235                 240

Leu Leu Gln Ile Thr Gly Arg Leu Asn Tyr Val Lys Cys Gln Val Tyr
                245                 250                 255

Leu Arg Glu Lys Leu Lys Asp Pro Thr Phe Asp Ile Thr Ser Ser Val
            260                 265                 270

Thr Cys Ala Gln Gln Leu Ser Glu Ser Pro Leu Leu Ala Ala Leu Ala
        275                 280                 285

Ser Gly Tyr Phe Trp Arg Phe Ile Lys Pro Lys Leu Asn Glu Thr Ala
290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
                325                 330                 335

Met Lys Glu Arg Val Gln Met Leu Ala Val Thr Lys Ala His Gly
            340                 345                 350

Ile Val

<210> SEQ ID NO 55
<211> LENGTH: 362
<212> TYPE: PRT
<213> ORGANISM: unknown
<220> FEATURE:
<223> OTHER INFORMATION: Ascaphine5-OBPgpLYS with additional His-tag

<400> SEQUENCE: 55

Met Gly Ile Lys Asp Trp Ile Lys Gly Ala Ala Lys Lys Leu Ile Lys
1               5                   10                  15

Thr Val Ala Ser His Ile Ala Asn Gln Gly Ser Lys Asn Ser Glu Lys
            20                  25                  30

Asn Ala Ser Ile Ile Met Ser Ile Gln Arg Thr Leu Ala Ser Leu Ser
        35                  40                  45

Leu Tyr Gly Gly Arg Ile Asp Gly Leu Phe Gly Glu Lys Cys Arg Gly
    50                  55                  60

Ala Ile Ile Leu Met Leu Asn Lys Val Tyr Pro Asn Phe Ser Thr Asn
65                  70                  75                  80

Lys Leu Pro Ser Asn Thr Tyr Glu Ala Glu Ser Val Phe Thr Phe Leu
                85                  90                  95

Gln Thr Ala Leu Ala Gly Val Gly Leu Tyr Thr Ile Thr Ile Asp Gly
            100                 105                 110

Lys Trp Gly Gly Thr Ser Gln Ala Ile Asp Ala Leu Val Lys Ser
        115                 120                 125

Tyr Arg Gln Ile Thr Glu Ala Glu Arg Ala Gly Ser Thr Leu Pro Leu
    130                 135                 140

Gly Leu Ala Thr Val Met Ser Lys His Met Ser Ile Glu Gln Leu Arg
145                 150                 155                 160

Ala Met Leu Pro Thr Asp Arg Gln Gly Tyr Ala Glu Val Tyr Ile Asp
                165                 170                 175

Pro Leu Asn Glu Thr Met Asp Ile Phe Glu Ile Asn Thr Pro Leu Arg
            180                 185                 190

Ile Ala His Phe Met Ala Gln Ile Leu His Glu Thr Ala Cys Phe Lys
        195                 200                 205
```

-continued

```
Tyr Thr Glu Glu Leu Ala Ser Gly Lys Ala Tyr Gly Arg Ala Asp
    210                 215                 220

Leu Gly Asn Thr Arg Pro Gly Asp Gly Pro Leu Phe Lys Gly Arg Gly
225                 230                 235                 240

Leu Leu Gln Ile Thr Gly Arg Leu Asn Tyr Val Lys Cys Gln Val Tyr
                245                 250                 255

Leu Arg Glu Lys Leu Lys Asp Pro Thr Phe Asp Ile Thr Ser Ser Val
            260                 265                 270

Thr Cys Ala Gln Gln Leu Ser Glu Ser Pro Leu Leu Ala Ala Leu Ala
        275                 280                 285

Ser Gly Tyr Phe Trp Arg Phe Ile Lys Pro Lys Leu Asn Glu Thr Ala
290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
                325                 330                 335

Met Lys Glu Arg Val Gln Met Leu Ala Val Thr Lys Lys Ala His Gly
            340                 345                 350

Ile Val Leu Glu His His His His His
            355                 360
```

<210> SEQ ID NO 56
<211> LENGTH: 347
<212> TYPE: PRT
<213> ORGANISM: unknown
<220> FEATURE:
<223> OTHER INFORMATION: Apidaecine-OBPgpLYS

<400> SEQUENCE: 56

```
Met Ala Asn Arg Pro Val Tyr Ile Pro Pro Arg Pro Pro His Pro
1               5                   10                  15

Arg Leu Gly Ser Lys Asn Ser Glu Lys Asn Ala Ser Ile Ile Met Ser
            20                  25                  30

Ile Gln Arg Thr Leu Ala Ser Leu Ser Leu Tyr Gly Gly Arg Ile Asp
        35                  40                  45

Gly Leu Phe Gly Glu Lys Cys Arg Gly Ala Ile Ile Leu Met Leu Asn
    50                  55                  60

Lys Val Tyr Pro Asn Phe Ser Thr Asn Lys Leu Pro Ser Asn Thr Tyr
65                  70                  75                  80

Glu Ala Glu Ser Val Phe Thr Phe Leu Gln Thr Ala Leu Ala Gly Val
                85                  90                  95

Gly Leu Tyr Thr Ile Thr Ile Asp Gly Lys Trp Gly Gly Thr Ser Gln
            100                 105                 110

Gly Ala Ile Asp Ala Leu Val Lys Ser Tyr Arg Gln Ile Thr Glu Ala
        115                 120                 125

Glu Arg Ala Gly Ser Thr Leu Pro Leu Gly Leu Ala Thr Val Met Ser
    130                 135                 140

Lys His Met Ser Ile Glu Gln Leu Arg Ala Met Leu Pro Thr Asp Arg
145                 150                 155                 160

Gln Gly Tyr Ala Glu Val Tyr Ile Asp Pro Leu Asn Glu Thr Met Asp
                165                 170                 175

Ile Phe Glu Ile Asn Thr Pro Leu Arg Ile Ala His Phe Met Ala Gln
            180                 185                 190

Ile Leu His Glu Thr Ala Cys Phe Lys Tyr Thr Glu Glu Leu Ala Ser
        195                 200                 205
```

Gly Lys Ala Tyr Glu Gly Arg Ala Asp Leu Gly Asn Thr Arg Pro Gly
            210                 215                 220

Asp Gly Pro Leu Phe Lys Gly Arg Gly Leu Leu Gln Ile Thr Gly Arg
225                 230                 235                 240

Leu Asn Tyr Val Lys Cys Gln Val Tyr Leu Arg Glu Lys Leu Lys Asp
                    245                 250                 255

Pro Thr Phe Asp Ile Thr Ser Ser Val Thr Cys Ala Gln Gln Leu Ser
                260                 265                 270

Glu Ser Pro Leu Leu Ala Ala Leu Ala Ser Gly Tyr Phe Trp Arg Phe
            275                 280                 285

Ile Lys Pro Lys Leu Asn Glu Thr Ala Asp Lys Asp Ile Tyr Trp
            290                 295                 300

Val Ser Val Tyr Val Asn Gly Tyr Ala Lys Gln Ala Asn Pro Tyr Tyr
305                 310                 315                 320

Pro Asn Arg Asp Lys Glu Pro Asn His Met Lys Glu Arg Val Gln Met
                325                 330                 335

Leu Ala Val Thr Lys Lys Ala His Gly Ile Val
            340                 345

<210> SEQ ID NO 57
<211> LENGTH: 355
<212> TYPE: PRT
<213> ORGANISM: unknown
<220> FEATURE:
<223> OTHER INFORMATION: Apidaecine-OBPgpLYS with additional His-tag

<400> SEQUENCE: 57

Met Ala Asn Arg Pro Val Tyr Ile Pro Pro Arg Pro Pro His Pro
1               5                   10                  15

Arg Leu Gly Ser Lys Asn Ser Glu Lys Asn Ala Ser Ile Ile Met Ser
                20                  25                  30

Ile Gln Arg Thr Leu Ala Ser Leu Ser Leu Tyr Gly Gly Arg Ile Asp
            35                  40                  45

Gly Leu Phe Gly Glu Lys Cys Arg Gly Ala Ile Ile Leu Met Leu Asn
50                  55                  60

Lys Val Tyr Pro Asn Phe Ser Thr Asn Lys Leu Pro Ser Asn Thr Tyr
65                  70                  75                  80

Glu Ala Glu Ser Val Phe Thr Phe Leu Gln Thr Ala Leu Ala Gly Val
                85                  90                  95

Gly Leu Tyr Thr Ile Thr Ile Asp Gly Lys Trp Gly Gly Thr Ser Gln
            100                 105                 110

Gly Ala Ile Asp Ala Leu Val Lys Ser Tyr Arg Gln Ile Thr Glu Ala
        115                 120                 125

Glu Arg Ala Gly Ser Thr Leu Pro Leu Gly Leu Ala Thr Val Met Ser
    130                 135                 140

Lys His Met Ser Ile Glu Gln Leu Arg Ala Met Leu Pro Thr Asp Arg
145                 150                 155                 160

Gln Gly Tyr Ala Glu Val Tyr Ile Asp Pro Leu Asn Glu Thr Met Asp
                165                 170                 175

Ile Phe Glu Ile Asn Thr Pro Leu Arg Ile Ala His Phe Met Ala Gln
            180                 185                 190

Ile Leu His Glu Thr Ala Cys Phe Lys Tyr Thr Glu Glu Leu Ala Ser
        195                 200                 205

Gly Lys Ala Tyr Glu Gly Arg Ala Asp Leu Gly Asn Thr Arg Pro Gly
    210                 215                 220

```
Asp Gly Pro Leu Phe Lys Gly Arg Gly Leu Leu Gln Ile Thr Gly Arg
225                 230                 235                 240

Leu Asn Tyr Val Lys Cys Gln Val Tyr Leu Arg Glu Lys Leu Lys Asp
            245                 250                 255

Pro Thr Phe Asp Ile Thr Ser Ser Val Thr Cys Ala Gln Gln Leu Ser
        260                 265                 270

Glu Ser Pro Leu Leu Ala Ala Leu Ala Ser Gly Tyr Phe Trp Arg Phe
    275                 280                 285

Ile Lys Pro Lys Leu Asn Glu Thr Ala Asp Lys Asp Ile Tyr Trp
290                 295                 300

Val Ser Val Tyr Val Asn Gly Tyr Ala Lys Gln Ala Asn Pro Tyr Tyr
305                 310                 315                 320

Pro Asn Arg Asp Lys Glu Pro Asn His Met Lys Glu Arg Val Gln Met
                325                 330                 335

Leu Ala Val Thr Lys Lys Ala His Gly Ile Val Leu Glu His His His
                340                 345                 350

His His His
        355

<210> SEQ ID NO 58
<211> LENGTH: 352
<212> TYPE: PRT
<213> ORGANISM: unknown
<220> FEATURE:
<223> OTHER INFORMATION: Nigrocine 2-OBPgpLYS

<400> SEQUENCE: 58

Met Gly Leu Leu Ser Lys Val Leu Gly Val Gly Lys Lys Val Leu Cys
1               5                   10                  15

Gly Val Ser Gly Leu Val Cys Gly Ser Lys Asn Ser Glu Lys Asn Ala
            20                  25                  30

Ser Ile Ile Met Ser Ile Gln Arg Thr Leu Ala Ser Leu Ser Leu Tyr
        35                  40                  45

Gly Gly Arg Ile Asp Gly Leu Phe Gly Glu Lys Cys Arg Gly Ala Ile
    50                  55                  60

Ile Leu Met Leu Asn Lys Val Tyr Pro Asn Phe Ser Thr Asn Lys Leu
65                  70                  75                  80

Pro Ser Asn Thr Tyr Glu Ala Glu Ser Val Phe Thr Phe Leu Gln Thr
                85                  90                  95

Ala Leu Ala Gly Val Gly Leu Tyr Thr Ile Thr Ile Asp Gly Lys Trp
            100                 105                 110

Gly Gly Thr Ser Gln Gly Ala Ile Asp Ala Leu Val Lys Ser Tyr Arg
        115                 120                 125

Gln Ile Thr Glu Ala Glu Arg Ala Gly Ser Thr Leu Pro Leu Gly Leu
    130                 135                 140

Ala Thr Val Met Ser Lys His Met Ser Ile Glu Gln Leu Arg Ala Met
145                 150                 155                 160

Leu Pro Thr Asp Arg Gln Gly Tyr Ala Glu Val Tyr Ile Asp Pro Leu
                165                 170                 175

Asn Glu Thr Met Asp Ile Phe Glu Ile Asn Thr Pro Leu Arg Ile Ala
            180                 185                 190

His Phe Met Ala Gln Ile Leu His Glu Thr Ala Cys Phe Lys Tyr Thr
        195                 200                 205

Glu Glu Leu Ala Ser Gly Lys Ala Tyr Glu Gly Arg Ala Asp Leu Gly
    210                 215                 220
```

Asn Thr Arg Pro Gly Asp Gly Pro Leu Phe Lys Gly Arg Gly Leu Leu
225                 230                 235                 240

Gln Ile Thr Gly Arg Leu Asn Tyr Val Lys Cys Gln Val Tyr Leu Arg
            245                 250                 255

Glu Lys Leu Lys Asp Pro Thr Phe Asp Ile Thr Ser Ser Val Thr Cys
        260                 265                 270

Ala Gln Gln Leu Ser Glu Ser Pro Leu Leu Ala Ala Leu Ala Ser Gly
    275                 280                 285

Tyr Phe Trp Arg Phe Ile Lys Pro Lys Leu Asn Glu Thr Ala Asp Lys
290                 295                 300

Asp Asp Ile Tyr Trp Val Ser Val Tyr Val Asn Gly Tyr Ala Lys Gln
305                 310                 315                 320

Ala Asn Pro Tyr Tyr Pro Asn Arg Asp Lys Glu Pro Asn His Met Lys
            325                 330                 335

Glu Arg Val Gln Met Leu Ala Val Thr Lys Lys Ala His Gly Ile Val
        340                 345                 350

<210> SEQ ID NO 59
<211> LENGTH: 360
<212> TYPE: PRT
<213> ORGANISM: unknown
<220> FEATURE:
<223> OTHER INFORMATION: Nigrocine 2-OBPgpLYS with additional His-tag

<400> SEQUENCE: 59

Met Gly Leu Leu Ser Lys Val Leu Gly Val Gly Lys Lys Val Leu Cys
1               5                   10                  15

Gly Val Ser Gly Leu Val Cys Gly Ser Lys Asn Ser Glu Lys Asn Ala
            20                  25                  30

Ser Ile Ile Met Ser Ile Gln Arg Thr Leu Ala Ser Leu Ser Leu Tyr
        35                  40                  45

Gly Gly Arg Ile Asp Gly Leu Phe Gly Glu Lys Cys Arg Gly Ala Ile
    50                  55                  60

Ile Leu Met Leu Asn Lys Val Tyr Pro Asn Phe Ser Thr Asn Lys Leu
65                  70                  75                  80

Pro Ser Asn Thr Tyr Glu Ala Glu Ser Val Phe Thr Phe Leu Gln Thr
            85                  90                  95

Ala Leu Ala Gly Val Gly Leu Tyr Thr Ile Thr Ile Asp Gly Lys Trp
        100                 105                 110

Gly Gly Thr Ser Gln Gly Ala Ile Asp Ala Leu Val Lys Ser Tyr Arg
    115                 120                 125

Gln Ile Thr Glu Ala Glu Arg Ala Gly Ser Thr Leu Pro Leu Gly Leu
130                 135                 140

Ala Thr Val Met Ser Lys His Met Ser Ile Glu Gln Leu Arg Ala Met
145                 150                 155                 160

Leu Pro Thr Asp Arg Gln Gly Tyr Ala Glu Val Tyr Ile Asp Pro Leu
            165                 170                 175

Asn Glu Thr Met Asp Ile Phe Glu Ile Asn Thr Pro Leu Arg Ile Ala
        180                 185                 190

His Phe Met Ala Gln Ile Leu His Glu Thr Ala Cys Phe Lys Tyr Thr
    195                 200                 205

Glu Glu Leu Ala Ser Gly Lys Ala Tyr Glu Gly Arg Ala Asp Leu Gly
210                 215                 220

Asn Thr Arg Pro Gly Asp Gly Pro Leu Phe Lys Gly Arg Gly Leu Leu
225                 230                 235                 240

```
Gln Ile Thr Gly Arg Leu Asn Tyr Val Lys Cys Gln Val Tyr Leu Arg
                245                 250                 255

Glu Lys Leu Lys Asp Pro Thr Phe Asp Ile Thr Ser Ser Val Thr Cys
            260                 265                 270

Ala Gln Gln Leu Ser Glu Ser Pro Leu Leu Ala Ala Leu Ala Ser Gly
        275                 280                 285

Tyr Phe Trp Arg Phe Ile Lys Pro Lys Leu Asn Glu Thr Ala Asp Lys
    290                 295                 300

Asp Asp Ile Tyr Trp Val Ser Val Tyr Val Asn Gly Tyr Ala Lys Gln
305                 310                 315                 320

Ala Asn Pro Tyr Tyr Pro Asn Arg Asp Lys Glu Pro Asn His Met Lys
                325                 330                 335

Glu Arg Val Gln Met Leu Ala Val Thr Lys Lys Ala His Gly Ile Val
            340                 345                 350

Leu Glu His His His His His His
            355                 360

<210> SEQ ID NO 60
<211> LENGTH: 354
<212> TYPE: PRT
<213> ORGANISM: unknown
<220> FEATURE:
<223> OTHER INFORMATION: Pseudin 1-OBPgpLYS

<400> SEQUENCE: 60

Met Gly Leu Asn Thr Leu Lys Lys Val Phe Gln Gly Leu His Glu Ala
1               5                   10                  15

Ile Lys Leu Ile Asn Asn His Val Gln Gly Ser Lys Asn Ser Glu Lys
            20                  25                  30

Asn Ala Ser Ile Ile Met Ser Ile Gln Arg Thr Leu Ala Ser Leu Ser
        35                  40                  45

Leu Tyr Gly Gly Arg Ile Asp Gly Leu Phe Gly Glu Lys Cys Arg Gly
    50                  55                  60

Ala Ile Ile Leu Met Leu Asn Lys Val Tyr Pro Asn Phe Ser Thr Asn
65                  70                  75                  80

Lys Leu Pro Ser Asn Thr Tyr Glu Ala Glu Ser Val Phe Thr Phe Leu
                85                  90                  95

Gln Thr Ala Leu Ala Gly Val Gly Leu Tyr Thr Ile Thr Ile Asp Gly
            100                 105                 110

Lys Trp Gly Gly Thr Ser Gln Gly Ala Ile Asp Ala Leu Val Lys Ser
        115                 120                 125

Tyr Arg Gln Ile Thr Glu Ala Glu Arg Ala Gly Ser Thr Leu Pro Leu
    130                 135                 140

Gly Leu Ala Thr Val Met Ser Lys His Met Ser Ile Glu Gln Leu Arg
145                 150                 155                 160

Ala Met Leu Pro Thr Asp Arg Gln Gly Tyr Ala Glu Val Tyr Ile Asp
                165                 170                 175

Pro Leu Asn Glu Thr Met Asp Ile Phe Glu Ile Asn Thr Pro Leu Arg
            180                 185                 190

Ile Ala His Phe Met Ala Gln Ile Leu His Glu Thr Ala Cys Phe Lys
        195                 200                 205

Tyr Thr Glu Glu Leu Ala Ser Gly Lys Ala Tyr Glu Gly Arg Ala Asp
    210                 215                 220

Leu Gly Asn Thr Arg Pro Gly Asp Gly Pro Leu Phe Lys Gly Arg Gly
225                 230                 235                 240
```

```
Leu Leu Gln Ile Thr Gly Arg Leu Asn Tyr Val Lys Cys Gln Val Tyr
            245                 250                 255

Leu Arg Glu Lys Leu Lys Asp Pro Thr Phe Asp Ile Thr Ser Ser Val
            260                 265                 270

Thr Cys Ala Gln Gln Leu Ser Glu Ser Pro Leu Leu Ala Ala Leu Ala
            275                 280                 285

Ser Gly Tyr Phe Trp Arg Phe Ile Lys Pro Lys Leu Asn Glu Thr Ala
            290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
            325                 330                 335

Met Lys Glu Arg Val Gln Met Leu Ala Val Thr Lys Lys Ala His Gly
            340                 345                 350

Ile Val

<210> SEQ ID NO 61
<211> LENGTH: 362
<212> TYPE: PRT
<213> ORGANISM: unknown
<220> FEATURE:
<223> OTHER INFORMATION: Pseudin 1-OBPgpLYS with additional His-tag

<400> SEQUENCE: 61

Met Gly Leu Asn Thr Leu Lys Lys Val Phe Gln Gly Leu His Glu Ala
1               5                   10                  15

Ile Lys Leu Ile Asn Asn His Val Gln Gly Ser Lys Asn Ser Glu Lys
            20                  25                  30

Asn Ala Ser Ile Ile Met Ser Ile Gln Arg Thr Leu Ala Ser Leu Ser
            35                  40                  45

Leu Tyr Gly Gly Arg Ile Asp Gly Leu Phe Gly Glu Lys Cys Arg Gly
        50                  55                  60

Ala Ile Ile Leu Met Leu Asn Lys Val Tyr Pro Asn Phe Ser Thr Asn
65                  70                  75                  80

Lys Leu Pro Ser Asn Thr Tyr Glu Ala Glu Ser Val Phe Thr Phe Leu
            85                  90                  95

Gln Thr Ala Leu Ala Gly Val Gly Leu Tyr Thr Ile Thr Ile Asp Gly
            100                 105                 110

Lys Trp Gly Gly Thr Ser Gln Gly Ala Ile Asp Ala Leu Val Lys Ser
            115                 120                 125

Tyr Arg Gln Ile Thr Glu Ala Glu Arg Ala Gly Ser Thr Leu Pro Leu
            130                 135                 140

Gly Leu Ala Thr Val Met Ser Lys His Met Ser Ile Glu Gln Leu Arg
145                 150                 155                 160

Ala Met Leu Pro Thr Asp Arg Gln Gly Tyr Ala Glu Val Tyr Ile Asp
            165                 170                 175

Pro Leu Asn Glu Thr Met Asp Ile Phe Glu Ile Asn Thr Pro Leu Arg
            180                 185                 190

Ile Ala His Phe Met Ala Gln Ile Leu His Glu Thr Ala Cys Phe Lys
            195                 200                 205

Tyr Thr Glu Glu Leu Ala Ser Gly Lys Ala Tyr Glu Gly Arg Ala Asp
            210                 215                 220

Leu Gly Asn Thr Arg Pro Gly Asp Gly Pro Leu Phe Lys Gly Arg Gly
225                 230                 235                 240
```

```
Leu Leu Gln Ile Thr Gly Arg Leu Asn Tyr Val Lys Cys Gln Val Tyr
            245                 250                 255

Leu Arg Glu Lys Leu Lys Asp Pro Thr Phe Asp Ile Thr Ser Ser Val
        260                 265                 270

Thr Cys Ala Gln Gln Leu Ser Glu Ser Pro Leu Leu Ala Ala Leu Ala
    275                 280                 285

Ser Gly Tyr Phe Trp Arg Phe Ile Lys Pro Lys Leu Asn Glu Thr Ala
        290                 295                 300

Asp Lys Asp Asp Ile Tyr Trp Val Ser Val Tyr Val Asn Gly Tyr Ala
305                 310                 315                 320

Lys Gln Ala Asn Pro Tyr Tyr Pro Asn Arg Asp Lys Glu Pro Asn His
                325                 330                 335

Met Lys Glu Arg Val Gln Met Leu Ala Val Thr Lys Lys Ala His Gly
            340                 345                 350

Ile Val Leu Glu His His His His His His
            355                 360

<210> SEQ ID NO 62
<211> LENGTH: 369
<212> TYPE: PRT
<213> ORGANISM: unknown
<220> FEATURE:
<223> OTHER INFORMATION: Sarcotoxin IA-OBPgpLYS

<400> SEQUENCE: 62

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Lys Asn Ser Glu Lys Asn
        35                  40                  45

Ala Ser Ile Ile Met Ser Ile Gln Arg Thr Leu Ala Ser Leu Ser Leu
    50                  55                  60

Tyr Gly Gly Arg Ile Asp Gly Leu Phe Gly Glu Lys Cys Arg Gly Ala
65                  70                  75                  80

Ile Ile Leu Met Leu Asn Lys Val Tyr Pro Asn Phe Ser Thr Asn Lys
                85                  90                  95

Leu Pro Ser Asn Thr Tyr Glu Ala Glu Ser Val Phe Thr Phe Leu Gln
            100                 105                 110

Thr Ala Leu Ala Gly Val Gly Leu Tyr Thr Ile Thr Ile Asp Gly Lys
        115                 120                 125

Trp Gly Gly Thr Ser Gln Gly Ala Ile Asp Ala Leu Val Lys Ser Tyr
    130                 135                 140

Arg Gln Ile Thr Glu Ala Glu Arg Ala Gly Ser Thr Leu Pro Leu Gly
145                 150                 155                 160

Leu Ala Thr Val Met Ser Lys His Met Ser Ile Glu Gln Leu Arg Ala
                165                 170                 175

Met Leu Pro Thr Asp Arg Gln Gly Tyr Ala Glu Val Tyr Ile Asp Pro
            180                 185                 190

Leu Asn Glu Thr Met Asp Ile Phe Glu Ile Asn Thr Pro Leu Arg Ile
        195                 200                 205

Ala His Phe Met Ala Gln Ile Leu His Glu Thr Ala Cys Phe Lys Tyr
    210                 215                 220

Thr Glu Glu Leu Ala Ser Gly Lys Ala Tyr Glu Gly Arg Ala Asp Leu
225                 230                 235                 240
```

```
Gly Asn Thr Arg Pro Gly Asp Gly Pro Leu Phe Lys Gly Arg Gly Leu
                245                 250                 255

Leu Gln Ile Thr Gly Arg Leu Asn Tyr Val Lys Cys Gln Val Tyr Leu
            260                 265                 270

Arg Glu Lys Leu Lys Asp Pro Thr Phe Asp Ile Thr Ser Ser Val Thr
        275                 280                 285

Cys Ala Gln Gln Leu Ser Glu Ser Pro Leu Leu Ala Ala Leu Ala Ser
    290                 295                 300

Gly Tyr Phe Trp Arg Phe Ile Lys Pro Lys Leu Asn Glu Thr Ala Asp
305                 310                 315                 320

Lys Asp Asp Ile Tyr Trp Val Ser Val Tyr Val Asn Gly Tyr Ala Lys
                325                 330                 335

Gln Ala Asn Pro Tyr Tyr Pro Asn Arg Asp Lys Glu Pro Asn His Met
            340                 345                 350

Lys Glu Arg Val Gln Met Leu Ala Val Thr Lys Lys Ala His Gly Ile
        355                 360                 365

Val

<210> SEQ ID NO 63
<211> LENGTH: 377
<212> TYPE: PRT
<213> ORGANISM: unknown
<220> FEATURE:
<223> OTHER INFORMATION: Sarcotoxin IA-OBPgpLYS with additional His-tag

<400> SEQUENCE: 63

Met Gly Trp Leu Lys Lys Ile Gly Lys Lys Ile Glu Arg Val Gly Gln
1               5                   10                  15

His Thr Arg Asp Ala Thr Ile Gln Gly Leu Gly Ile Ala Gln Gln Ala
            20                  25                  30

Ala Asn Val Ala Ala Thr Ala Arg Gly Ser Lys Asn Ser Glu Lys Asn
        35                  40                  45

Ala Ser Ile Ile Met Ser Ile Gln Arg Thr Leu Ala Ser Leu Ser Leu
    50                  55                  60

Tyr Gly Gly Arg Ile Asp Gly Leu Phe Gly Glu Lys Cys Arg Gly Ala
65                  70                  75                  80

Ile Ile Leu Met Leu Asn Lys Val Tyr Pro Asn Phe Ser Thr Asn Lys
                85                  90                  95

Leu Pro Ser Asn Thr Tyr Glu Ala Glu Ser Val Phe Thr Phe Leu Gln
            100                 105                 110

Thr Ala Leu Ala Gly Val Gly Leu Tyr Thr Ile Thr Ile Asp Gly Lys
        115                 120                 125

Trp Gly Gly Thr Ser Gln Gly Ala Ile Asp Ala Leu Val Lys Ser Tyr
    130                 135                 140

Arg Gln Ile Thr Glu Ala Glu Arg Ala Gly Ser Thr Leu Pro Leu Gly
145                 150                 155                 160

Leu Ala Thr Val Met Ser Lys His Met Ser Ile Glu Gln Leu Arg Ala
                165                 170                 175

Met Leu Pro Thr Asp Arg Gln Gly Tyr Ala Glu Val Tyr Ile Asp Pro
            180                 185                 190

Leu Asn Glu Thr Met Asp Ile Phe Glu Ile Asn Thr Pro Leu Arg Ile
        195                 200                 205

Ala His Phe Met Ala Gln Ile Leu His Glu Thr Ala Cys Phe Lys Tyr
    210                 215                 220

Thr Glu Glu Leu Ala Ser Gly Lys Ala Tyr Glu Gly Arg Ala Asp Leu
```

```
                225                 230                 235                 240
Gly Asn Thr Arg Pro Gly Asp Gly Pro Leu Phe Lys Gly Arg Gly Leu
                245                 250                 255

Leu Gln Ile Thr Gly Arg Leu Asn Tyr Val Lys Cys Gln Val Tyr Leu
                260                 265                 270

Arg Glu Lys Leu Lys Asp Pro Thr Phe Asp Ile Thr Ser Ser Val Thr
                275                 280                 285

Cys Ala Gln Gln Leu Ser Glu Ser Pro Leu Leu Ala Ala Leu Ala Ser
                290                 295                 300

Gly Tyr Phe Trp Arg Phe Ile Lys Pro Lys Leu Asn Glu Thr Ala Asp
305                 310                 315                 320

Lys Asp Asp Ile Tyr Trp Val Ser Val Tyr Val Asn Gly Tyr Ala Lys
                    325                 330                 335

Gln Ala Asn Pro Tyr Tyr Pro Asn Arg Asp Lys Glu Pro Asn His Met
                340                 345                 350

Lys Glu Arg Val Gln Met Leu Ala Val Thr Lys Lys Ala His Gly Ile
                355                 360                 365

Val Leu Glu His His His His His His
                370                 375

<210> SEQ ID NO 64
<211> LENGTH: 359
<212> TYPE: PRT
<213> ORGANISM: unknown
<220> FEATURE:
<223> OTHER INFORMATION: Sarcotoxin IA-OBPgpLYS

<400> S

```
                210                 215                 220
Glu Gly Arg Ala Asp Leu Gly Asn Thr Arg Pro Gly Asp Gly Pro Leu
225                 230                 235                 240

Phe Lys Gly Arg Gly Leu Leu Gln Ile Thr Gly Arg Leu Asn Tyr Val
                245                 250                 255

Lys Cys Gln Val Tyr Leu Arg Glu Lys Leu Lys Asp Pro Thr Phe Asp
                260                 265                 270

Ile Thr Ser Ser Val Thr Cys Ala Gln Gln Leu Ser Glu Ser Pro Leu
                275                 280                 285

Leu Ala Ala Leu Ala Ser Gly Tyr Phe Trp Arg Phe Ile Lys Pro Lys
                290                 295                 300

Leu Asn Glu Thr Ala Asp Lys Asp Asp Ile Tyr Trp Val Ser Val Tyr
305                 310                 315                 320

Val Asn Gly Tyr Ala Lys Gln Ala Asn Pro Tyr Pro Asn Arg Asp
                325                 330                 335

Lys Glu Pro Asn His Met Lys Glu Arg Val Gln Met Leu Ala Val Thr
                340                 345                 350

Lys Lys Ala His Gly Ile Val
                355

<210> SEQ ID NO 65
<211> LENGTH: 367
<212> TYPE: PRT
<213> ORGANISM: unknown
<220> FEATURE:
<223> OTHER INFORMATION: Sarcotoxin IA-OBPgpLYS with additional His-tag

<400> SEQUENCE: 65

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Lys Asn Ser Glu Lys Asn Ala Ser Ile Ile Met Ser Ile Gln Arg Thr
                35                  40                  45

Leu Ala Ser Leu Ser Leu Tyr Gly Gly Arg Ile Asp Gly Leu Phe Gly
                50                  55                  60

Glu Lys Cys Arg Gly Ala Ile Ile Leu Met Leu Asn Lys Val Tyr Pro
65                  70                  75                  80

Asn Phe Ser Thr Asn Lys Leu Pro Ser Asn Thr Tyr Glu Ala Glu Ser
                85                  90                  95

Val Phe Thr Phe Leu Gln Thr Ala Leu Ala Gly Val Gly Leu Tyr Thr
                100                 105                 110

Ile Thr Ile Asp Gly Lys Trp Gly Gly Thr Ser Gln Gly Ala Ile Asp
                115                 120                 125

Ala Leu Val Lys Ser Tyr Arg Gln Ile Thr Glu Ala Glu Arg Ala Gly
                130                 135                 140

Ser Thr Leu Pro Leu Gly Leu Ala Thr Val Met Ser Lys His Met Ser
145                 150                 155                 160

Ile Glu Gln Leu Arg Ala Met Leu Pro Thr Asp Arg Gln Gly Tyr Ala
                165                 170                 175

Glu Val Tyr Ile Asp Pro Leu Asn Glu Thr Met Asp Ile Phe Glu Ile
                180                 185                 190

Asn Thr Pro Leu Arg Ile Ala His Phe Met Ala Gln Ile Leu His Glu
                195                 200                 205

Thr Ala Cys Phe Lys Tyr Thr Glu Glu Leu Ala Ser Gly Lys Ala Tyr
```

```
            210                 215                 220
Glu Gly Arg Ala Asp Leu Gly Asn Thr Arg Pro Gly Asp Gly Pro Leu
225                 230                 235                 240

Phe Lys Gly Arg Gly Leu Leu Gln Ile Thr Gly Arg Leu Asn Tyr Val
                245                 250                 255

Lys Cys Gln Val Tyr Leu Arg Glu Lys Leu Lys Asp Pro Thr Phe Asp
                    260                 265                 270

Ile Thr Ser Ser Val Thr Cys Ala Gln Gln Leu Ser Glu Ser Pro Leu
                275                 280                 285

Leu Ala Ala Leu Ala Ser Gly Tyr Phe Trp Arg Phe Ile Lys Pro Lys
            290                 295                 300

Leu Asn Glu Thr Ala Asp Lys Asp Ile Tyr Trp Val Ser Val Tyr
305                 310                 315                 320

Val Asn Gly Tyr Ala Lys Gln Ala Asn Pro Tyr Tyr Pro Asn Arg Asp
                    325                 330                 335

Lys Glu Pro Asn His Met Lys Glu Arg Val Gln Met Leu Ala Val Thr
                340                 345                 350

Lys Lys Ala His Gly Ile Val Leu Glu His His His His His
            355                 360                 365

<210> SEQ ID NO 66
<211> LENGTH: 366
<212> TYPE: PRT
<213> ORGANISM: unknown
<220> FEATURE:
<223> OTHER INFORMATION: Cecropin A (A.aegypti)-OBPgpLYS

<400> SEQUENCE: 66

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
                20                  25                  30

Lys Ala Leu Arg Lys Gly Ser Lys Asn Ser Glu Lys Asn Ala Ser Ile
            35                  40                  45

Ile Met Ser Ile Gln Arg Thr Leu Ala Ser Leu Ser Leu Tyr Gly Gly
50                  55                  60

Arg Ile Asp Gly Leu Phe Gly Glu Lys Cys Arg Gly Ala Ile Ile Leu
65                  70                  75                  80

Met Leu Asn Lys Val Tyr Pro Asn Phe Ser Thr Asn Lys Leu Pro Ser
                85                  90                  95

Asn Thr Tyr Glu Ala Glu Ser Val Phe Thr Phe Leu Gln Thr Ala Leu
                100                 105                 110

Ala Gly Val Gly Leu Tyr Thr Ile Thr Ile Asp Gly Lys Trp Gly Gly
            115                 120                 125

Thr Ser Gln Gly Ala Ile Asp Ala Leu Val Lys Ser Tyr Arg Gln Ile
130                 135                 140

Thr Glu Ala Glu Arg Ala Gly Ser Thr Leu Pro Leu Gly Leu Ala Thr
145                 150                 155                 160

Val Met Ser Lys His Met Ser Ile Glu Gln Leu Arg Ala Met Leu Pro
                165                 170                 175

Thr Asp Arg Gln Gly Tyr Ala Glu Val Tyr Ile Asp Pro Leu Asn Glu
                180                 185                 190

Thr Met Asp Ile Phe Glu Ile Asn Thr Pro Leu Arg Ile Ala His Phe
            195                 200                 205

Met Ala Gln Ile Leu His Glu Thr Ala Cys Phe Lys Tyr Thr Glu Glu
```

```
            210                 215                 220
Leu Ala Ser Gly Lys Ala Tyr Glu Gly Arg Ala Asp Leu Gly Asn Thr
225                 230                 235                 240

Arg Pro Gly Asp Gly Pro Leu Phe Lys Gly Arg Gly Leu Leu Gln Ile
                245                 250                 255

Thr Gly Arg Leu Asn Tyr Val Lys Cys Gln Val Tyr Leu Arg Glu Lys
                260                 265                 270

Leu Lys Asp Pro Thr Phe Asp Ile Thr Ser Ser Val Thr Cys Ala Gln
                275                 280                 285

Gln Leu Ser Glu Ser Pro Leu Leu Ala Ala Leu Ala Ser Gly Tyr Phe
            290                 295                 300

Trp Arg Phe Ile Lys Pro Lys Leu Asn Glu Thr Ala Asp Lys Asp Asp
305                 310                 315                 320

Ile Tyr Trp Val Ser Val Tyr Val Asn Gly Tyr Ala Lys Gln Ala Asn
                325                 330                 335

Pro Tyr Tyr Pro Asn Arg Asp Lys Glu Pro Asn His Met Lys Glu Arg
                340                 345                 350

Val Gln Met Leu Ala Val Thr Lys Lys Ala His Gly Ile Val
            355                 360                 365
```

<210> SEQ ID NO 67
<211> LENGTH: 374
<212> TYPE: PRT
<213> ORGANISM: unknown
<220> FEATURE:
<223> OTHER INFORMATION: Cecropin A (A.aegypti)-OBPgpLYS with additional
      His-tag

<400> SEQUENCE: 67

```
Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
                20                  25                  30

Lys Ala Leu Arg Lys Gly Ser Lys Asn Ser Glu Lys Asn Ala Ser Ile
            35                  40                  45

Ile Met Ser Ile Gln Arg Thr Leu Ala Ser Leu Ser Leu Tyr Gly Gly
50                  55                  60

Arg Ile Asp Gly Leu Phe Gly Glu Lys Cys Arg Gly Ala Ile Ile Leu
65                  70                  75                  80

Met Leu Asn Lys Val Tyr Pro Asn Phe Ser Thr Asn Lys Leu Pro Ser
                85                  90                  95

Asn Thr Tyr Glu Ala Glu Ser Val Phe Thr Phe Leu Gln Thr Ala Leu
                100                 105                 110

Ala Gly Val Gly Leu Tyr Thr Ile Thr Ile Asp Gly Lys Trp Gly Gly
            115                 120                 125

Thr Ser Gln Gly Ala Ile Asp Ala Leu Val Lys Ser Tyr Arg Gln Ile
130                 135                 140

Thr Glu Ala Glu Arg Ala Gly Ser Thr Leu Pro Leu Gly Leu Ala Thr
145                 150                 155                 160

Val Met Ser Lys His Met Ser Ile Glu Gln Leu Arg Ala Met Leu Pro
                165                 170                 175

Thr Asp Arg Gln Gly Tyr Ala Glu Val Tyr Ile Asp Pro Leu Asn Glu
                180                 185                 190

Thr Met Asp Ile Phe Glu Ile Asn Thr Pro Leu Arg Ile Ala His Phe
            195                 200                 205
```

-continued

```
Met Ala Gln Ile Leu His Glu Thr Ala Cys Phe Lys Tyr Thr Glu Glu
210                 215                 220

Leu Ala Ser Gly Lys Ala Tyr Glu Gly Arg Ala Asp Leu Gly Asn Thr
225                 230                 235                 240

Arg Pro Gly Asp Gly Pro Leu Phe Lys Gly Arg Gly Leu Leu Gln Ile
                245                 250                 255

Thr Gly Arg Leu Asn Tyr Val Lys Cys Gln Val Tyr Leu Arg Glu Lys
            260                 265                 270

Leu Lys Asp Pro Thr Phe Asp Ile Thr Ser Val Thr Cys Ala Gln
        275                 280                 285

Gln Leu Ser Glu Ser Pro Leu Leu Ala Ala Leu Ala Ser Gly Tyr Phe
290                 295                 300

Trp Arg Phe Ile Lys Pro Lys Leu Asn Glu Thr Ala Asp Lys Asp
305                 310                 315                 320

Ile Tyr Trp Val Ser Tyr Val Asn Gly Tyr Ala Lys Gln Ala Asn
                325                 330                 335

Pro Tyr Tyr Pro Asn Arg Asp Lys Glu Pro Asn His Met Lys Glu Arg
                340                 345                 350

Val Gln Met Leu Ala Val Thr Lys Lys Ala His Gly Ile Val Leu Glu
                355                 360                 365

His His His His His His
370

<210> SEQ ID NO 68
<211> LENGTH: 13
<212> TYPE: PRT
<213> ORGANISM: unknown
<220> FEATURE:
<223> OTHER INFORMATION: antimicrobial peptide Alpha 4

<400> SEQUENCE: 68

Pro Asn Arg Ala Lys Arg Val Ile Thr Thr Phe Arg Thr
1               5                   10

<210> SEQ ID NO 69
<211> LENGTH: 327
<212> TYPE: PRT
<213> ORGANISM: unknown
<220> FEATURE:
<223> OTHER INFORMATION: OBPgpLYS fragment

<400> SEQUENCE: 69

Lys Asn Ser Glu Lys Asn Ala Ser Ile Ile Met Ser Ile Gln Arg Thr
1               5                   10                  15

Leu Ala Ser Leu Ser Leu Tyr Gly Gly Arg Ile Asp Gly Leu Phe Gly
                20                  25                  30

Glu Lys Cys Arg Gly Ala Ile Ile Leu Met Leu Asn Lys Val Tyr Pro
            35                  40                  45

Asn Phe Ser Thr Asn Lys Leu Pro Ser Asn Thr Tyr Glu Ala Glu Ser
        50                  55                  60

Val Phe Thr Phe Leu Gln Thr Ala Leu Ala Gly Val Gly Leu Tyr Thr
65                  70                  75                  80

Ile Thr Ile Asp Gly Lys Trp Gly Gly Thr Ser Gln Gly Ala Ile Asp
                85                  90                  95

Ala Leu Val Lys Ser Tyr Arg Gln Ile Thr Glu Ala Glu Arg Ala Gly
            100                 105                 110

Ser Thr Leu Pro Leu Gly Leu Ala Thr Val Met Ser Lys His Met Ser
        115                 120                 125
```

```
Ile Glu Gln Leu Arg Ala Met Leu Pro Thr Asp Arg Gln Gly Tyr Ala
        130                 135                 140

Glu Val Tyr Ile Asp Pro Leu Asn Glu Thr Met Asp Ile Phe Glu Ile
145                 150                 155                 160

Asn Thr Pro Leu Arg Ile Ala His Phe Met Ala Gln Ile Leu His Glu
                165                 170                 175

Thr Ala Cys Phe Lys Tyr Thr Glu Glu Leu Ala Ser Gly Lys Ala Tyr
            180                 185                 190

Glu Gly Arg Ala Asp Leu Gly Asn Thr Arg Pro Gly Asp Gly Pro Leu
        195                 200                 205

Phe Lys Gly Arg Gly Leu Leu Gln Ile Thr Gly Arg Leu Asn Tyr Val
        210                 215                 220

Lys Cys Gln Val Tyr Leu Arg Glu Lys Leu Lys Asp Pro Thr Phe Asp
225                 230                 235                 240

Ile Thr Ser Ser Val Thr Cys Ala Gln Gln Leu Ser Glu Ser Pro Leu
                245                 250                 255

Leu Ala Ala Leu Ala Ser Gly Tyr Phe Trp Arg Phe Ile Lys Pro Lys
            260                 265                 270

Leu Asn Glu Thr Ala Asp Lys Asp Asp Ile Tyr Trp Val Ser Val Tyr
        275                 280                 285

Val Asn Gly Tyr Ala Lys Gln Ala Asn Pro Tyr Tyr Pro Asn Arg Asp
        290                 295                 300

Lys Glu Pro Asn His Met Lys Glu Arg Val Gln Met Leu Ala Val Thr
305                 310                 315                 320

Lys Lys Ala Leu Gly Ile Val
                325

<210> SEQ ID NO 70
<211> LENGTH: 18
<212> TYPE: PRT
<213> ORGANISM: unknown
<220> FEATURE:
<223> OTHER INFORMATION: antimicropial peptide Artilysin1

<400> SEQUENCE: 70

Gly Phe Phe Ile Pro Ala Val Ile Leu Pro Ser Ile Ala Phe Leu Ile
1               5                   10                  15

Val Pro

<210> SEQ ID NO 71
<211> LENGTH: 25
<212> TYPE: PRT
<213> ORGANISM: unknown
<220> FEATURE:
<223> OTHER INFORMATION: antimicrobial peptide Artilysin2

<400> SEQUENCE: 71

Gly Lys Pro Gly Trp Leu Ile Lys Lys Ala Leu Val Phe Lys Lys Leu
1               5                   10                  15

Ile Arg Arg Pro Leu Lys Arg Leu Ala
            20                  25

<210> SEQ ID NO 72
<211> LENGTH: 19
<212> TYPE: PRT
<213> ORGANISM: unknown
<220> FEATURE:
<223> OTHER INFORMATION: antimicrobial peptide Parasin 1
```

<400> SEQUENCE: 72

Lys Gly Arg Gly Lys Gln Gly Gly Lys Val Arg Ala Lys Ala Lys Thr
1               5                   10                  15

Arg Ser Ser

<210> SEQ ID NO 73
<211> LENGTH: 25
<212> TYPE: PRT
<213> ORGANISM: unknown
<220> FEATURE:
<223> OTHER INFORMATION: antimicrobial peptide Lycotoxin

<400> SEQUENCE: 73

Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25

<210> SEQ ID NO 74
<211> LENGTH: 346
<212> TYPE: PRT
<213> ORGANISM: unknown
<220> FEATURE:
<223> OTHER INFORMATION: Alpha4-OBPgpLYS

<400> SEQUENCE: 74

Met Gly Ser Pro Asn Arg Ala Lys Arg Val Ile Thr Thr Phe Arg Thr
1               5                   10                  15

Gly Ser Ser Lys Asn Ser Glu Lys Asn Ala Ser Ile Ile Met Ser Ile
            20                  25                  30

Gln Arg Thr Leu Ala Ser Leu Ser Leu Tyr Gly Gly Arg Ile Asp Gly
        35                  40                  45

Leu Phe Gly Glu Lys Cys Arg Gly Ala Ile Ile Leu Met Leu Asn Lys
    50                  55                  60

Val Tyr Pro Asn Phe Ser Thr Asn Lys Leu Pro Ser Asn Thr Tyr Glu
65                  70                  75                  80

Ala Glu Ser Val Phe Thr Phe Leu Gln Thr Ala Leu Ala Gly Val Gly
                85                  90                  95

Leu Tyr Thr Ile Thr Ile Asp Gly Lys Trp Gly Gly Thr Ser Gln Gly
            100                 105                 110

Ala Ile Asp Ala Leu Val Lys Ser Tyr Arg Gln Ile Thr Glu Ala Glu
        115                 120                 125

Arg Ala Gly Ser Thr Leu Pro Leu Gly Leu Ala Thr Val Met Ser Lys
    130                 135                 140

His Met Ser Ile Glu Gln Leu Arg Ala Met Leu Pro Thr Asp Arg Gln
145                 150                 155                 160

Gly Tyr Ala Glu Val Tyr Ile Asp Pro Leu Asn Glu Thr Met Asp Ile
                165                 170                 175

Phe Glu Ile Asn Thr Pro Leu Arg Ile Ala His Phe Met Ala Gln Ile
            180                 185                 190

Leu His Glu Thr Ala Cys Phe Lys Tyr Thr Glu Glu Leu Ala Ser Gly
        195                 200                 205

Lys Ala Tyr Glu Gly Arg Ala Asp Leu Gly Asn Thr Arg Pro Gly Asp
    210                 215                 220

Gly Pro Leu Phe Lys Gly Arg Gly Leu Leu Gln Ile Thr Gly Arg Leu
225                 230                 235                 240

Asn Tyr Val Lys Cys Gln Val Tyr Leu Arg Glu Lys Leu Lys Asp Pro

```
                     245                 250                 255
Thr Phe Asp Ile Thr Ser Ser Val Thr Cys Ala Gln Gln Leu Ser Glu
                 260                 265                 270

Ser Pro Leu Leu Ala Ala Leu Ala Ser Gly Tyr Phe Trp Arg Phe Ile
             275                 280                 285

Lys Pro Lys Leu Asn Glu Thr Ala Asp Lys Asp Ile Tyr Trp Val
         290                 295                 300

Ser Val Tyr Val Asn Gly Tyr Ala Lys Gln Ala Asn Pro Tyr Tyr Pro
305                 310                 315                 320

Asn Arg Asp Lys Glu Pro Asn His Met Lys Glu Arg Val Gln Met Leu
                 325                 330                 335

Ala Val Thr Lys Lys Ala His Gly Ile Val
                 340                 345

<210> SEQ ID NO 75
<211> LENGTH: 354
<212> TYPE: PRT
<213> ORGANISM: unknown
<220> FEATURE:
<223> OTHER INFORMATION: Alpha4-OBPgpLYS with additional His-tag

<400> SEQUENCE: 75

Met Gly Ser Pro Asn Arg Ala Lys Arg Val Ile Thr Thr Phe Arg Thr
1               5                   10                  15

Gly Ser Ser Lys Asn Ser Glu Lys Asn Ala Ser Ile Ile Met Ser Ile
             20                  25                  30

Gln Arg Thr Leu Ala Ser Leu Ser Leu Tyr Gly Gly Arg Ile Asp Gly
         35                  40                  45

Leu Phe Gly Glu Lys Cys Arg Gly Ala Ile Ile Leu Met Leu Asn Lys
    50                  55                  60

Val Tyr Pro Asn Phe Ser Thr Asn Lys Leu Pro Ser Asn Thr Tyr Glu
65                  70                  75                  80

Ala Glu Ser Val Phe Thr Phe Leu Gln Thr Ala Leu Ala Gly Val Gly
                 85                  90                  95

Leu Tyr Thr Ile Thr Ile Asp Gly Lys Trp Gly Gly Thr Ser Gln Gly
             100                 105                 110

Ala Ile Asp Ala Leu Val Lys Ser Tyr Arg Gln Ile Thr Glu Ala Glu
         115                 120                 125

Arg Ala Gly Ser Thr Leu Pro Leu Gly Leu Ala Thr Val Met Ser Lys
    130                 135                 140

His Met Ser Ile Glu Gln Leu Arg Ala Met Leu Pro Thr Asp Arg Gln
145                 150                 155                 160

Gly Tyr Ala Glu Val Tyr Ile Asp Pro Leu Asn Glu Thr Met Asp Ile
                 165                 170                 175

Phe Glu Ile Asn Thr Pro Leu Arg Ile Ala His Phe Met Ala Gln Ile
             180                 185                 190

Leu His Glu Thr Ala Cys Phe Lys Tyr Thr Glu Leu Ala Ser Gly
         195                 200                 205

Lys Ala Tyr Glu Gly Arg Ala Asp Leu Gly Asn Thr Arg Pro Gly Asp
    210                 215                 220

Gly Pro Leu Phe Lys Gly Arg Gly Leu Leu Gln Ile Thr Gly Arg Leu
225                 230                 235                 240

Asn Tyr Val Lys Cys Gln Val Tyr Leu Arg Glu Lys Leu Lys Asp Pro
                 245                 250                 255

Thr Phe Asp Ile Thr Ser Ser Val Thr Cys Ala Gln Gln Leu Ser Glu
```

```
            260                 265                 270
Ser Pro Leu Leu Ala Ala Leu Ala Ser Gly Tyr Phe Trp Arg Phe Ile
        275                 280                 285

Lys Pro Lys Leu Asn Glu Thr Ala Asp Lys Asp Asp Ile Tyr Trp Val
290                 295                 300

Ser Val Tyr Val Asn Gly Tyr Ala Lys Gln Ala Asn Pro Tyr Tyr Pro
305                 310                 315                 320

Asn Arg Asp Lys Glu Pro Asn His Met Lys Glu Arg Val Gln Met Leu
                325                 330                 335

Ala Val Thr Lys Lys Ala His Gly Ile Val Lys Gly His His His His
                340                 345                 350

His His

<210> SEQ ID NO 76
<211> LENGTH: 338
<212> TYPE: PRT
<213> ORGANISM: unknown
<220> FEATURE:
<223> OTHER INFORMATION: OBPgpLys

<400> SEQUENCE: 76

Met Gly Ser Phe Phe Val Ala Pro Gly Ser Ser Lys Asn Ser Glu Lys
1               5                   10                  15

Asn Ala Ser Ile Ile Met Ser Ile Gln Arg Thr Leu Ala Ser Leu Ser
            20                  25                  30

Leu Tyr Gly Gly Arg Ile Asp Gly Leu Phe Gly Glu Lys Cys Arg Gly
        35                  40                  45

Ala Ile Ile Leu Met Leu Asn Lys Val Tyr Pro Asn Phe Ser Thr Asn
50                  55                  60

Lys Leu Pro Ser Asn Thr Tyr Glu Ala Glu Ser Val Phe Thr Phe Leu
65                  70                  75                  80

Gln Thr Ala Leu Ala Gly Val Gly Leu Tyr Thr Ile Thr Ile Asp Gly
                85                  90                  95

Lys Trp Gly Gly Thr Ser Gln Gly Ala Ile Asp Ala Leu Val Lys Ser
            100                 105                 110

Tyr Arg Gln Ile Thr Glu Ala Glu Arg Ala Gly Ser Thr Leu Pro Leu
        115                 120                 125

Gly Leu Ala Thr Val Met Ser Lys His Met Ser Ile Glu Gln Leu Arg
130                 135                 140

Ala Met Leu Pro Thr Asp Arg Gln Gly Tyr Ala Glu Val Tyr Ile Asp
145                 150                 155                 160

Pro Leu Asn Glu Thr Met Asp Ile Phe Glu Ile Asn Thr Pro Leu Arg
                165                 170                 175

Ile Ala His Phe Met Ala Gln Ile Leu His Glu Thr Ala Cys Phe Lys
            180                 185                 190

Tyr Thr Glu Glu Leu Ala Ser Gly Lys Ala Tyr Glu Gly Arg Ala Asp
        195                 200                 205

Leu Gly Asn Thr Arg Pro Gly Asp Gly Pro Leu Phe Lys Gly Arg Gly
210                 215                 220

Leu Leu Gln Ile Thr Gly Arg Leu Asn Tyr Val Lys Cys Gln Val Tyr
225                 230                 235                 240

Leu Arg Glu Lys Leu Lys Asp Pro Thr Phe Asp Ile Thr Ser Ser Val
                245                 250                 255

Thr Cys Ala Gln Gln Leu Ser Glu Ser Pro Leu Leu Ala Ala Leu Ala
            260                 265                 270
```

```
Ser Gly Tyr Phe Trp Arg Phe Ile Lys Pro Lys Leu Asn Glu Thr Ala
        275                 280                 285

Asp Lys Asp Asp Ile Tyr Trp Val Ser Val Tyr Val Asn Gly Tyr Ala
290                 295                 300

Lys Gln Ala Asn Pro Tyr Tyr Pro Asn Arg Asp Lys Glu Pro Asn His
305                 310                 315                 320

Met Lys Glu Arg Val Gln Met Leu Ala Val Thr Lys Lys Ala His Gly
                325                 330                 335

Ile Val

<210> SEQ ID NO 77
<211> LENGTH: 346
<212> TYPE: PRT
<213> ORGANISM: unknown
<220> FEATURE:
<223> OTHER INFORMATION: OBPgpLys with additional His-tag

<400> SEQUENCE: 77

Met Gly Ser Phe Phe Val Ala Pro Gly Ser Ser Lys Asn Ser Glu Lys
1               5                   10                  15

Asn Ala Ser Ile Ile Met Ser Ile Gln Arg Thr Leu Ala Ser Leu Ser
            20                  25                  30

Leu Tyr Gly Gly Arg Ile Asp Gly Leu Phe Gly Glu Lys Cys Arg Gly
        35                  40                  45

Ala Ile Ile Leu Met Leu Asn Lys Val Tyr Pro Asn Phe Ser Thr Asn
    50                  55                  60

Lys Leu Pro Ser Asn Thr Tyr Glu Ala Glu Ser Val Phe Thr Phe Leu
65                  70                  75                  80

Gln Thr Ala Leu Ala Gly Val Gly Leu Tyr Thr Ile Thr Ile Asp Gly
                85                  90                  95

Lys Trp Gly Gly Thr Ser Gln Gly Ala Ile Asp Ala Leu Val Lys Ser
            100                 105                 110

Tyr Arg Gln Ile Thr Glu Ala Glu Arg Ala Gly Ser Thr Leu Pro Leu
        115                 120                 125

Gly Leu Ala Thr Val Met Ser Lys His Met Ser Ile Glu Gln Leu Arg
    130                 135                 140

Ala Met Leu Pro Thr Asp Arg Gln Gly Tyr Ala Glu Val Tyr Ile Asp
145                 150                 155                 160

Pro Leu Asn Glu Thr Met Asp Ile Phe Glu Ile Asn Thr Pro Leu Arg
                165                 170                 175

Ile Ala His Phe Met Ala Gln Ile Leu His Glu Thr Ala Cys Phe Lys
            180                 185                 190

Tyr Thr Glu Glu Leu Ala Ser Gly Lys Ala Tyr Glu Gly Arg Ala Asp
        195                 200                 205

Leu Gly Asn Thr Arg Pro Gly Asp Gly Pro Leu Phe Lys Gly Arg Gly
    210                 215                 220

Leu Leu Gln Ile Thr Gly Arg Leu Asn Tyr Val Lys Cys Gln Val Tyr
225                 230                 235                 240

Leu Arg Glu Lys Leu Lys Asp Pro Thr Phe Asp Ile Thr Ser Ser Val
                245                 250                 255

Thr Cys Ala Gln Gln Leu Ser Glu Ser Pro Leu Leu Ala Ala Leu Ala
            260                 265                 270

Ser Gly Tyr Phe Trp Arg Phe Ile Lys Pro Lys Leu Asn Glu Thr Ala
        275                 280                 285
```

```
Asp Lys Asp Asp Ile Tyr Trp Val Ser Val Tyr Val Asn Gly Tyr Ala
    290                 295                 300

Lys Gln Ala Asn Pro Tyr Tyr Pro Asn Arg Asp Lys Glu Pro Asn His
305                 310                 315                 320

Met Lys Glu Arg Val Gln Met Leu Ala Val Thr Lys Lys Ala His Gly
                325                 330                 335

Ile Val Lys Gly His His His His His His
                340                 345

<210> SEQ ID NO 78
<211> LENGTH: 351
<212> TYPE: PRT
<213> ORGANISM: unknown
<220> FEATURE:
<223> OTHER INFORMATION: Artilys1-OBPgpLys

<400> SEQUENCE: 78

Met Gly Ser Gly Phe Phe Ile Pro Ala Val Ile Leu Pro Ser Ile Ala
1               5                   10                  15

Phe Leu Ile Val Pro Gly Ser Ser Lys Asn Ser Glu Lys Asn Ala Ser
            20                  25                  30

Ile Ile Met Ser Ile Gln Arg Thr Leu Ala Ser Leu Ser Leu Tyr Gly
        35                  40                  45

Gly Arg Ile Asp Gly Leu Phe Gly Glu Lys Cys Arg Gly Ala Ile Ile
50                  55                  60

Leu Met Leu Asn Lys Val Tyr Pro Asn Phe Ser Thr Asn Lys Leu Pro
65                  70                  75                  80

Ser Asn Thr Tyr Glu Ala Glu Ser Val Phe Thr Phe Leu Gln Thr Ala
                85                  90                  95

Leu Ala Gly Val Gly Leu Tyr Thr Ile Thr Ile Asp Gly Lys Trp Gly
            100                 105                 110

Gly Thr Ser Gln Gly Ala Ile Asp Ala Leu Val Lys Ser Tyr Arg Gln
        115                 120                 125

Ile Thr Glu Ala Glu Arg Ala Gly Ser Thr Leu Pro Leu Gly Leu Ala
130                 135                 140

Thr Val Met Ser Lys His Met Ser Ile Glu Gln Leu Arg Ala Met Leu
145                 150                 155                 160

Pro Thr Asp Arg Gln Gly Tyr Ala Glu Val Tyr Ile Asp Pro Leu Asn
                165                 170                 175

Glu Thr Met Asp Ile Phe Glu Ile Asn Thr Pro Leu Arg Ile Ala His
            180                 185                 190

Phe Met Ala Gln Ile Leu His Glu Thr Ala Cys Phe Lys Tyr Thr Glu
        195                 200                 205

Glu Leu Ala Ser Gly Lys Ala Tyr Glu Gly Arg Ala Asp Leu Gly Asn
210                 215                 220

Thr Arg Pro Gly Asp Gly Pro Leu Phe Lys Gly Arg Gly Leu Leu Gln
225                 230                 235                 240

Ile Thr Gly Arg Leu Asn Tyr Val Lys Cys Gln Val Tyr Leu Arg Glu
                245                 250                 255

Lys Leu Lys Asp Pro Thr Phe Asp Ile Thr Ser Ser Val Thr Cys Ala
            260                 265                 270

Gln Gln Leu Ser Glu Ser Pro Leu Leu Ala Ala Leu Ala Ser Gly Tyr
        275                 280                 285

Phe Trp Arg Phe Ile Lys Pro Lys Leu Asn Glu Thr Ala Asp Lys Asp
290                 295                 300
```

-continued

```
Asp Ile Tyr Trp Val Ser Val Tyr Val Asn Gly Tyr Ala Lys Gln Ala
305                 310                 315                 320

Asn Pro Tyr Tyr Pro Asn Arg Asp Lys Glu Pro Asn His Met Lys Glu
            325                 330                 335

Arg Val Gln Met Leu Ala Val Thr Lys Lys Ala His Gly Ile Val
        340                 345                 350

<210> SEQ ID NO 79
<211> LENGTH: 359
<212> TYPE: PRT
<213> ORGANISM: unknown
<220> FEATURE:
<223> OTHER INFORMATION: Artilys1-OBPgpLys with additional His-tag

<400> SEQUENCE: 79

Met Gly Ser Gly Phe Phe Ile Pro Ala Val Ile Leu Pro Ser Ile Ala
1               5                   10                  15

Phe Leu Ile Val Pro Gly Ser Ser Lys Asn Ser Glu Lys Asn Ala Ser
            20                  25                  30

Ile Ile Met Ser Ile Gln Arg Thr Leu Ala Ser Leu Ser Leu Tyr Gly
        35                  40                  45

Gly Arg Ile Asp Gly Leu Phe Gly Glu Lys Cys Arg Gly Ala Ile Ile
50                  55                  60

Leu Met Leu Asn Lys Val Tyr Pro Asn Phe Ser Thr Asn Lys Leu Pro
65                  70                  75                  80

Ser Asn Thr Tyr Glu Ala Glu Ser Val Phe Thr Phe Leu Gln Thr Ala
                85                  90                  95

Leu Ala Gly Val Gly Leu Tyr Thr Ile Thr Ile Asp Gly Lys Trp Gly
            100                 105                 110

Gly Thr Ser Gln Gly Ala Ile Asp Ala Leu Val Lys Ser Tyr Arg Gln
        115                 120                 125

Ile Thr Glu Ala Glu Arg Ala Gly Ser Thr Leu Pro Leu Gly Leu Ala
130                 135                 140

Thr Val Met Ser Lys His Met Ser Ile Glu Gln Leu Arg Ala Met Leu
145                 150                 155                 160

Pro Thr Asp Arg Gln Gly Tyr Ala Glu Val Tyr Ile Asp Pro Leu Asn
                165                 170                 175

Glu Thr Met Asp Ile Phe Glu Ile Asn Thr Pro Leu Arg Ile Ala His
            180                 185                 190

Phe Met Ala Gln Ile Leu His Glu Thr Ala Cys Phe Lys Tyr Thr Glu
        195                 200                 205

Glu Leu Ala Ser Gly Lys Ala Tyr Glu Gly Arg Ala Asp Leu Gly Asn
    210                 215                 220

Thr Arg Pro Gly Asp Gly Pro Leu Phe Lys Gly Arg Gly Leu Leu Gln
225                 230                 235                 240

Ile Thr Gly Arg Leu Asn Tyr Val Lys Cys Gln Val Tyr Leu Arg Glu
                245                 250                 255

Lys Leu Lys Asp Pro Thr Phe Asp Ile Thr Ser Ser Val Thr Cys Ala
            260                 265                 270

Gln Gln Leu Ser Glu Ser Pro Leu Leu Ala Ala Leu Ala Ser Gly Tyr
        275                 280                 285

Phe Trp Arg Phe Ile Lys Pro Lys Leu Asn Glu Thr Ala Asp Lys Asp
    290                 295                 300

Asp Ile Tyr Trp Val Ser Val Tyr Val Asn Gly Tyr Ala Lys Gln Ala
305                 310                 315                 320
```

```
Asn Pro Tyr Tyr Pro Asn Arg Asp Lys Glu Pro Asn His Met Lys Glu
                325                 330                 335

Arg Val Gln Met Leu Ala Val Thr Lys Lys Ala His Gly Ile Val Lys
            340                 345                 350

Gly His His His His His
        355

<210> SEQ ID NO 80
<211> LENGTH: 358
<212> TYPE: PRT
<213> ORGANISM: unknown
<220> FEATURE:
<223> OTHER INFORMATION: Artilys2-OBPgpLYS

<400> SEQUENCE: 80

Met Gly Ser Gly Lys Pro Gly Trp Leu Ile Lys Lys Ala Leu Val Phe
1               5                   10                  15

Lys Lys Leu Ile Arg Arg Pro Leu Lys Arg Leu Ala Gly Ser Ser Lys
            20                  25                  30

Asn Ser Glu Lys Asn Ala Ser Ile Ile Met Ser Ile Gln Arg Thr Leu
        35                  40                  45

Ala Ser Leu Ser Leu Tyr Gly Gly Arg Ile Asp Gly Leu Phe Gly Glu
    50                  55                  60

Lys Cys Arg Gly Ala Ile Ile Leu Met Leu Asn Lys Val Tyr Pro Asn
65                  70                  75                  80

Phe Ser Thr Asn Lys Leu Pro Ser Asn Thr Tyr Glu Ala Glu Ser Val
                85                  90                  95

Phe Thr Phe Leu Gln Thr Ala Leu Ala Gly Val Gly Leu Tyr Thr Ile
            100                 105                 110

Thr Ile Asp Gly Lys Trp Gly Gly Thr Ser Gln Gly Ala Ile Asp Ala
        115                 120                 125

Leu Val Lys Ser Tyr Arg Gln Ile Thr Glu Ala Glu Arg Ala Gly Ser
    130                 135                 140

Thr Leu Pro Leu Gly Leu Ala Thr Val Met Ser Lys His Met Ser Ile
145                 150                 155                 160

Glu Gln Leu Arg Ala Met Leu Pro Thr Asp Arg Gln Gly Tyr Ala Glu
                165                 170                 175

Val Tyr Ile Asp Pro Leu Asn Glu Thr Met Asp Ile Phe Glu Ile Asn
            180                 185                 190

Thr Pro Leu Arg Ile Ala His Phe Met Ala Gln Ile Leu His Glu Thr
        195                 200                 205

Ala Cys Phe Lys Tyr Thr Glu Glu Leu Ala Ser Gly Lys Ala Tyr Glu
    210                 215                 220

Gly Arg Ala Asp Leu Gly Asn Thr Arg Pro Gly Asp Gly Pro Leu Phe
225                 230                 235                 240

Lys Gly Arg Gly Leu Leu Gln Ile Thr Gly Arg Leu Asn Tyr Val Lys
                245                 250                 255

Cys Gln Val Tyr Leu Arg Glu Lys Leu Lys Asp Pro Thr Phe Asp Ile
            260                 265                 270

Thr Ser Ser Val Thr Cys Ala Gln Gln Leu Ser Glu Ser Pro Leu Leu
        275                 280                 285

Ala Ala Leu Ala Ser Gly Tyr Phe Trp Arg Phe Ile Lys Pro Lys Leu
    290                 295                 300

Asn Glu Thr Ala Asp Lys Asp Asp Ile Tyr Trp Val Ser Val Tyr Val
305                 310                 315                 320
```

```
Asn Gly Tyr Ala Lys Gln Ala Asn Pro Tyr Tyr Pro Asn Arg Asp Lys
                325                 330                 335

Glu Pro Asn His Met Lys Glu Arg Val Gln Met Leu Ala Val Thr Lys
            340                 345                 350

Lys Ala His Gly Ile Val
        355

<210> SEQ ID NO 81
<211> LENGTH: 366
<212> TYPE: PRT
<213> ORGANISM: unknown
<220> FEATURE:
<223> OTHER INFORMATION: Artilys2-OBPgpLYS with additional His-tag

<400> SEQUENCE: 81

Met Gly Ser Gly Lys Pro Gly Trp Leu Ile Lys Lys Ala Leu Val Phe
1               5                   10                  15

Lys Lys Leu Ile Arg Arg Pro Leu Lys Arg Leu Ala Gly Ser Ser Lys
            20                  25                  30

Asn Ser Glu Lys Asn Ala Ser Ile Ile Met Ser Ile Gln Arg Thr Leu
        35                  40                  45

Ala Ser Leu Ser Leu Tyr Gly Gly Arg Ile Asp Gly Leu Phe Gly Glu
    50                  55                  60

Lys Cys Arg Gly Ala Ile Ile Leu Met Leu Asn Lys Val Tyr Pro Asn
65                  70                  75                  80

Phe Ser Thr Asn Lys Leu Pro Ser Asn Thr Tyr Glu Ala Glu Ser Val
                85                  90                  95

Phe Thr Phe Leu Gln Thr Ala Leu Ala Gly Val Gly Leu Tyr Thr Ile
            100                 105                 110

Thr Ile Asp Gly Lys Trp Gly Gly Thr Ser Gln Gly Ala Ile Asp Ala
        115                 120                 125

Leu Val Lys Ser Tyr Arg Gln Ile Thr Glu Ala Glu Arg Ala Gly Ser
    130                 135                 140

Thr Leu Pro Leu Gly Leu Ala Thr Val Met Ser Lys His Met Ser Ile
145                 150                 155                 160

Glu Gln Leu Arg Ala Met Leu Pro Thr Asp Arg Gln Gly Tyr Ala Glu
                165                 170                 175

Val Tyr Ile Asp Pro Leu Asn Glu Thr Met Asp Ile Phe Glu Ile Asn
            180                 185                 190

Thr Pro Leu Arg Ile Ala His Phe Met Ala Gln Ile Leu His Glu Thr
        195                 200                 205

Ala Cys Phe Lys Tyr Thr Glu Glu Leu Ala Ser Gly Lys Ala Tyr Glu
    210                 215                 220

Gly Arg Ala Asp Leu Gly Asn Thr Arg Pro Gly Asp Gly Pro Leu Phe
225                 230                 235                 240

Lys Gly Arg Gly Leu Leu Gln Ile Thr Gly Arg Leu Asn Tyr Val Lys
                245                 250                 255

Cys Gln Val Tyr Leu Arg Glu Lys Leu Lys Asp Pro Thr Phe Asp Ile
            260                 265                 270

Thr Ser Ser Val Thr Cys Ala Gln Gln Leu Ser Glu Ser Pro Leu Leu
        275                 280                 285

Ala Ala Leu Ala Ser Gly Tyr Phe Trp Arg Phe Ile Lys Pro Lys Leu
    290                 295                 300

Asn Glu Thr Ala Asp Lys Asp Asp Ile Tyr Trp Val Ser Val Tyr Val
305                 310                 315                 320
```

Asn Gly Tyr Ala Lys Gln Ala Asn Pro Tyr Tyr Pro Asn Arg Asp Lys
                    325                 330                 335

Glu Pro Asn His Met Lys Glu Arg Val Gln Met Leu Ala Val Thr Lys
                340                 345                 350

Lys Ala His Gly Ile Val Lys Gly His His His His His His
            355                 360                 365

<210> SEQ ID NO 82
<211> LENGTH: 352
<212> TYPE: PRT
<213> ORGANISM: unknown
<220> FEATURE:
<223> OTHER INFORMATION: Parasin1-OBPgpLys

<400> SEQUENCE: 82

Met Gly Ser Lys Gly Arg Gly Lys Gln Gly Gly Lys Val Arg Ala Lys
1               5                   10                  15

Ala Lys Thr Arg Ser Ser Gly Ser Ser Lys Asn Ser Glu Lys Asn Ala
                20                  25                  30

Ser Ile Ile Met Ser Ile Gln Arg Thr Leu Ala Ser Leu Ser Leu Tyr
            35                  40                  45

Gly Gly Arg Ile Asp Gly Leu Phe Gly Glu Lys Cys Arg Gly Ala Ile
        50                  55                  60

Ile Leu Met Leu Asn Lys Val Tyr Pro Asn Phe Ser Thr Asn Lys Leu
65                  70                  75                  80

Pro Ser Asn Thr Tyr Glu Ala Glu Ser Val Phe Thr Phe Leu Gln Thr
                85                  90                  95

Ala Leu Ala Gly Val Gly Leu Tyr Thr Ile Thr Ile Asp Gly Lys Trp
            100                 105                 110

Gly Gly Thr Ser Gln Gly Ala Ile Asp Ala Leu Val Lys Ser Tyr Arg
        115                 120                 125

Gln Ile Thr Glu Ala Glu Arg Ala Gly Ser Thr Leu Pro Leu Gly Leu
130                 135                 140

Ala Thr Val Met Ser Lys His Met Ser Ile Glu Gln Leu Arg Ala Met
145                 150                 155                 160

Leu Pro Thr Asp Arg Gln Gly Tyr Ala Glu Val Tyr Ile Asp Pro Leu
                165                 170                 175

Asn Glu Thr Met Asp Ile Phe Glu Ile Asn Thr Pro Leu Arg Ile Ala
            180                 185                 190

His Phe Met Ala Gln Ile Leu His Glu Thr Ala Cys Phe Lys Tyr Thr
        195                 200                 205

Glu Glu Leu Ala Ser Gly Lys Ala Tyr Glu Gly Arg Ala Asp Leu Gly
    210                 215                 220

Asn Thr Arg Pro Gly Asp Gly Pro Leu Phe Lys Gly Arg Gly Leu Leu
225                 230                 235                 240

Gln Ile Thr Gly Arg Leu Asn Tyr Val Lys Cys Gln Val Tyr Leu Arg
                245                 250                 255

Glu Lys Leu Lys Asp Pro Thr Phe Asp Ile Thr Ser Val Thr Cys
            260                 265                 270

Ala Gln Gln Leu Ser Glu Ser Pro Leu Leu Ala Ala Leu Ala Ser Gly
        275                 280                 285

Tyr Phe Trp Arg Phe Ile Lys Pro Lys Leu Asn Glu Thr Ala Asp Lys
    290                 295                 300

Asp Asp Ile Tyr Trp Val Ser Tyr Val Asn Gly Tyr Ala Lys Gln
305                 310                 315                 320

Ala Asn Pro Tyr Tyr Pro Asn Arg Asp Lys Glu Pro Asn His Met Lys
                325                 330                 335

Glu Arg Val Gln Met Leu Ala Val Thr Lys Lys Ala His Gly Ile Val
            340                 345                 350

<210> SEQ ID NO 83
<211> LENGTH: 360
<212> TYPE: PRT
<213> ORGANISM: unknown
<220> FEATURE:
<223> OTHER INFORMATION: Parasin1-OBPgpLys with additional His-tag

<400> SEQUENCE: 83

Met Gly Ser Lys Gly Arg Gly Lys Gln Gly Gly Lys Val Arg Ala Lys
1               5                   10                  15

Ala Lys Thr Arg Ser Ser Gly Ser Ser Lys Asn Ser Glu Lys Asn Ala
            20                  25                  30

Ser Ile Ile Met Ser Ile Gln Arg Thr Leu Ala Ser Leu Ser Leu Tyr
        35                  40                  45

Gly Gly Arg Ile Asp Gly Leu Phe Gly Lys Cys Arg Gly Ala Ile
    50                  55                  60

Ile Leu Met Leu Asn Lys Val Tyr Pro Asn Phe Ser Thr Asn Lys Leu
65                  70                  75                  80

Pro Ser Asn Thr Tyr Glu Ala Glu Ser Val Phe Thr Phe Leu Gln Thr
                85                  90                  95

Ala Leu Ala Gly Val Gly Leu Tyr Thr Ile Thr Ile Asp Gly Lys Trp
            100                 105                 110

Gly Gly Thr Ser Gln Gly Ala Ile Asp Ala Leu Val Lys Ser Tyr Arg
        115                 120                 125

Gln Ile Thr Glu Ala Glu Arg Ala Gly Ser Thr Leu Pro Leu Gly Leu
    130                 135                 140

Ala Thr Val Met Ser Lys His Met Ser Ile Glu Gln Leu Arg Ala Met
145                 150                 155                 160

Leu Pro Thr Asp Arg Gln Gly Tyr Ala Glu Val Tyr Ile Asp Pro Leu
                165                 170                 175

Asn Glu Thr Met Asp Ile Phe Glu Ile Asn Thr Pro Leu Arg Ile Ala
            180                 185                 190

His Phe Met Ala Gln Ile Leu His Glu Thr Ala Cys Phe Lys Tyr Thr
        195                 200                 205

Glu Glu Leu Ala Ser Gly Lys Ala Tyr Glu Gly Arg Ala Asp Leu Gly
    210                 215                 220

Asn Thr Arg Pro Gly Asp Gly Pro Leu Phe Lys Gly Arg Gly Leu Leu
225                 230                 235                 240

Gln Ile Thr Gly Arg Leu Asn Tyr Val Lys Cys Gln Val Tyr Leu Arg
                245                 250                 255

Glu Lys Leu Lys Asp Pro Thr Phe Asp Ile Thr Ser Ser Val Thr Cys
            260                 265                 270

Ala Gln Gln Leu Ser Glu Ser Pro Leu Leu Ala Ala Leu Ala Ser Gly
        275                 280                 285

Tyr Phe Trp Arg Phe Ile Lys Pro Lys Leu Asn Glu Thr Ala Asp Lys
    290                 295                 300

Asp Asp Ile Tyr Trp Val Ser Val Tyr Val Asn Gly Tyr Ala Lys Gln
305                 310                 315                 320

Ala Asn Pro Tyr Tyr Pro Asn Arg Asp Lys Glu Pro Asn His Met Lys
                325                 330                 335

```
Glu Arg Val Gln Met Leu Ala Val Thr Lys Lys Ala His Gly Ile Val
                340                 345                 350
Lys Gly His His His His His His
        355                 360

<210> SEQ ID NO 84
<211> LENGTH: 358
<212> TYPE: PRT
<213> ORGANISM: unknown
<220> FEATURE:
<223> OTHER INFORMATION: Lycotoxin-OBPgLys

<400> SEQUENCE: 84

Met Gly Ser Ile Trp Leu Thr Ala Leu Lys Phe Leu Gly Lys His Ala
1               5                   10                  15
Ala Lys Lys Leu Ala Lys Gln Gln Leu Ser Lys Leu Gly Ser Ser Lys
                20                  25                  30
Asn Ser Glu Lys Asn Ala Ser Ile Ile Met Ser Ile Gln Arg Thr Leu
            35                  40                  45
Ala Ser Leu Ser Leu Tyr Gly Gly Arg Ile Asp Gly Leu Phe Gly Glu
        50                  55                  60
Lys Cys Arg Gly Ala Ile Ile Leu Met Leu Asn Lys Val Tyr Pro Asn
65                  70                  75                  80
Phe Ser Thr Asn Lys Leu Pro Ser Asn Thr Tyr Glu Ala Glu Ser Val
                85                  90                  95
Phe Thr Phe Leu Gln Thr Ala Leu Ala Gly Val Gly Leu Tyr Thr Ile
                100                 105                 110
Thr Ile Asp Gly Lys Trp Gly Gly Thr Ser Gln Gly Ala Ile Asp Ala
            115                 120                 125
Leu Val Lys Ser Tyr Arg Gln Ile Thr Glu Ala Glu Arg Ala Gly Ser
        130                 135                 140
Thr Leu Pro Leu Gly Leu Ala Thr Val Met Ser Lys His Met Ser Ile
145                 150                 155                 160
Glu Gln Leu Arg Ala Met Leu Pro Thr Asp Arg Gln Gly Tyr Ala Glu
                165                 170                 175
Val Tyr Ile Asp Pro Leu Asn Glu Thr Met Asp Ile Phe Glu Ile Asn
                180                 185                 190
Thr Pro Leu Arg Ile Ala His Phe Met Ala Gln Ile Leu His Glu Thr
            195                 200                 205
Ala Cys Phe Lys Tyr Thr Glu Glu Leu Ala Ser Gly Lys Ala Tyr Glu
        210                 215                 220
Gly Arg Ala Asp Leu Gly Asn Thr Arg Pro Gly Asp Gly Pro Leu Phe
225                 230                 235                 240
Lys Gly Arg Gly Leu Leu Gln Ile Thr Gly Arg Leu Asn Tyr Val Lys
                245                 250                 255
Cys Gln Val Tyr Leu Arg Glu Lys Leu Lys Asp Pro Thr Phe Asp Ile
                260                 265                 270
Thr Ser Ser Val Thr Cys Ala Gln Gln Leu Ser Glu Ser Pro Leu Leu
            275                 280                 285
Ala Ala Leu Ala Ser Gly Tyr Phe Trp Arg Phe Ile Lys Pro Lys Leu
        290                 295                 300
Asn Glu Thr Ala Asp Lys Asp Ile Tyr Trp Val Ser Val Tyr Val
305                 310                 315                 320
Asn Gly Tyr Ala Lys Gln Ala Asn Pro Tyr Tyr Pro Asn Arg Asp Lys
                325                 330                 335
```

```
Glu Pro Asn His Met Lys Glu Arg Val Gln Met Leu Ala Val Thr Lys
                340                 345                 350
Lys Ala His Gly Ile Val
            355

<210> SEQ ID NO 85
<211> LENGTH: 366
<212> TYPE: PRT
<213> ORGANISM: unknown
<220> FEATURE:
<223> OTHER INFORMATION: Lycotoxin-OBPgLys with additional His-tag

<400> SEQUENCE: 85

Met Gly Ser Ile Trp Leu Thr Ala Leu Lys Phe Leu Gly Lys His Ala
1               5                   10                  15
Ala Lys Lys Leu Ala Lys Gln Gln Leu Ser Lys Leu Gly Ser Ser Lys
                20                  25                  30
Asn Ser Glu Lys Asn Ala Ser Ile Ile Met Ser Ile Gln Arg Thr Leu
            35                  40                  45
Ala Ser Leu Ser Leu Tyr Gly Gly Arg Ile Asp Gly Leu Phe Gly Glu
        50                  55                  60
Lys Cys Arg Gly Ala Ile Ile Leu Met Leu Asn Lys Val Tyr Pro Asn
65                  70                  75                  80
Phe Ser Thr Asn Lys Leu Pro Ser As

```
Glu Pro Asn His Met Lys Glu Arg Val Gln Met Leu Ala Val Thr Lys
                340                 345                 350
Lys Ala His Gly Ile Val Lys Gly His His His His His His
            355                 360                 365
```

<210> SEQ ID NO 86
<211> LENGTH: 328
<212> TYPE: PRT
<213> ORGANISM: unknown
<220> FEATURE:
<223> OTHER INFORMATION: OBPgpLYS

<400> SEQUENCE: 86

```
Met Lys Asn Ser Glu Lys Asn Ala Ser Ile Ile Met Ser Ile Gln Arg
1               5                   10                  15
Thr Leu Ala Ser Leu Ser Leu Tyr Gly Gly Arg Ile Asp Gly Leu Phe
                20                  25                  30
Gly Glu Lys Cys Arg Gly Ala Ile Ile Leu Met Leu Asn Lys Val Tyr
            35                  40                  45
Pro Asn Phe Ser Thr Asn Lys Leu Pro Ser Asn Thr Tyr Glu Ala Glu
        50                  55                  60
Ser Val Phe Thr Phe Leu Gln Thr Ala Leu Ala Gly Val Gly Leu Tyr
65                  70                  75                  80
Thr Ile Thr Ile Asp Gly Lys Trp Gly Gly Thr Ser Gln Gly Ala Ile
                85                  90                  95
Asp Ala Leu Val Lys Ser Tyr Arg Gln Ile Thr Glu Ala Glu Arg Ala
            100                 105                 110
Gly Ser Thr Leu Pro Leu Gly Leu Ala Thr Val Met Ser Lys His Met
        115                 120                 125
Ser Ile Glu Gln Leu Arg Ala Met Leu Pro Thr Asp Arg Gln Gly Tyr
130                 135                 140
Ala Glu Val Tyr Ile Asp Pro Leu Asn Glu Thr Met Asp Ile Phe Glu
145                 150                 155                 160
Ile Asn Thr Pro Leu Arg Ile Ala His Phe Met Ala Gln Ile Leu His
                165                 170                 175
Glu Thr Ala Cys Phe Lys Tyr Thr Glu Glu Leu Ala Ser Gly Lys Ala
            180                 185                 190
Tyr Glu Gly Arg Ala Asp Leu Gly Asn Thr Arg Pro Gly Asp Gly Pro
        195                 200                 205
Leu Phe Lys Gly Arg Gly Leu Leu Gln Ile Thr Gly Arg Leu Asn Tyr
    210                 215                 220
Val Lys Cys Gln Val Tyr Leu Arg Glu Lys Leu Lys Asp Pro Thr Phe
225                 230                 235                 240
Asp Ile Thr Ser Ser Val Thr Cys Ala Gln Gln Leu Ser Glu Ser Pro
                245                 250                 255
Leu Leu Ala Ala Leu Ala Ser Gly Tyr Phe Trp Arg Phe Ile Lys Pro
            260                 265                 270
Lys Leu Asn Glu Thr Ala Asp Lys Asp Ile Tyr Trp Val Ser Val
        275                 280                 285
Tyr Val Asn Gly Tyr Ala Lys Gln Ala Asn Pro Tyr Tyr Pro Asn Arg
    290                 295                 300
Asp Lys Glu Pro Asn His Met Lys Glu Arg Val Gln Met Leu Ala Val
305                 310                 315                 320
Thr Lys Lys Ala His Gly Ile Val
                325
```

<210> SEQ ID NO 87
<211> LENGTH: 327
<212> TYPE: PRT
<213> ORGANISM: unknown
<220> FEATURE:
<223> OTHER INFORMATION: OBPgpLYS

<400> SEQUENCE: 87

Lys Asn Ser Glu Lys Asn Ala Ser Ile Ile Met Ser Ile Gln Arg Thr
1               5                   10                  15

Leu Ala Ser Leu Ser Leu Tyr Gly Gly Arg Ile Asp Gly Leu Phe Gly
            20                  25                  30

Glu Lys Cys Arg Gly Ala Ile Ile Leu Met Leu Asn Lys Val Tyr Pro
        35                  40                  45

Asn Phe Ser Thr Asn Lys Leu Pro Ser Asn Thr Tyr Glu Ala Glu Ser
    50                  55                  60

Val Phe Thr Phe Leu Gln Thr Ala Leu Ala Gly Val Gly Leu Tyr Thr
65                  70                  75                  80

Ile Thr Ile Asp Gly Lys Trp Gly Gly Thr Ser Gln Gly Ala Ile Asp
                85                  90                  95

Ala Leu Val Lys Ser Tyr Arg Gln Ile Thr Glu Ala Gly Arg Ala Gly
            100                 105                 110

Ser Thr Leu Pro Leu Gly Leu Ala Thr Val Met Ser Lys His Met Ser
        115                 120                 125

Ile Glu Gln Leu Arg Ala Met Leu Pro Thr Asp Arg Gln Gly Tyr Ala
    130                 135                 140

Glu Val Tyr Ile Asp Pro Leu Asn Glu Thr Met Asp Ile Phe Glu Ile
145                 150                 155                 160

Asn Thr Pro Leu Arg Ile Ala His Phe Met Ala Gln Ile Leu His Glu
                165                 170                 175

Thr Ala Cys Phe Lys Tyr Thr Glu Gly Leu Ala Ser Gly Lys Ala Tyr
            180                 185                 190

Glu Gly Arg Ala Asp Leu Gly Asn Thr Arg Pro Gly Asp Gly Pro Leu
        195                 200                 205

Phe Lys Gly Arg Gly Leu Leu Gln Ile Thr Gly Arg Leu Asn Tyr Val
    210                 215                 220

Lys Cys Gln Val Tyr Leu Arg Glu Lys Leu Lys Asp Pro Thr Phe Asp
225                 230                 235                 240

Ile Thr Ser Ser Val Thr Cys Ala Gln Gln Leu Ser Glu Ser Pro Leu
                245                 250                 255

Leu Ala Ala Leu Ala Ser Gly Tyr Phe Trp Arg Phe Ile Lys Pro Lys
            260                 265                 270

Leu Asn Glu Thr Ala Asp Lys Asp Asp Ile Tyr Trp Val Ser Val Tyr
        275                 280                 285

Val Asn Gly Tyr Ala Lys Gln Ala Asn Pro Tyr Tyr Pro Asn Arg Asp
    290                 295                 300

Lys Glu Pro Asn His Met Lys Glu Arg Val Gln Met Leu Ala Val Thr
305                 310                 315                 320

Lys Lys Ala His Gly Ile Val
                325

<210> SEQ ID NO 88
<211> LENGTH: 336
<212> TYPE: PRT
<213> ORGANISM: unknown
<220> FEATURE:

<223> OTHER INFORMATION: OBPgpLYS derivative with His-tag

<400> SEQUENCE: 88

| Met | Lys | Asn | Ser | Glu | Lys | Asn | Ala | Ser | Ile | Ile | Met | Ser | Ile | Gln | Arg |
|---|---|---|---|---|---|---|---|---|---|---|---|---|---|---|---|
| 1 | | | | 5 | | | | | 10 | | | | | 15 | |

| Thr | Leu | Ala | Ser | Leu | Ser | Leu | Tyr | Gly | Gly | Arg | Ile | Asp | Gly | Leu | Phe |
|---|---|---|---|---|---|---|---|---|---|---|---|---|---|---|---|
| | | | 20 | | | | | 25 | | | | | 30 | | |

| Gly | Glu | Lys | Cys | Arg | Gly | Ala | Ile | Ile | Leu | Met | Leu | Asn | Lys | Val | Tyr |
|---|---|---|---|---|---|---|---|---|---|---|---|---|---|---|---|
| | | 35 | | | | | 40 | | | | | 45 | | | |

| Pro | Asn | Phe | Ser | Thr | Asn | Lys | Leu | Pro | Ser | Asn | Thr | Tyr | Glu | Ala | Glu |
|---|---|---|---|---|---|---|---|---|---|---|---|---|---|---|---|
| 50 | | | | | 55 | | | | | 60 | | | | | |

| Ser | Val | Phe | Thr | Phe | Leu | Gln | Thr | Ala | Leu | Ala | Gly | Val | Gly | Leu | Tyr |
|---|---|---|---|---|---|---|---|---|---|---|---|---|---|---|---|
| 65 | | | | | 70 | | | | | 75 | | | | | 80 |

| Thr | Ile | Thr | Ile | Asp | Gly | Lys | Trp | Gly | Gly | Thr | Ser | Gln | Gly | Ala | Ile |
|---|---|---|---|---|---|---|---|---|---|---|---|---|---|---|---|
| | | | | 85 | | | | | 90 | | | | | 95 | |

| Asp | Ala | Leu | Val | Lys | Ser | Tyr | Arg | Gln | Ile | Thr | Glu | Ala | Glu | Arg | Ala |
|---|---|---|---|---|---|---|---|---|---|---|---|---|---|---|---|
| | | | 100 | | | | | 105 | | | | | 110 | | |

| Gly | Ser | Thr | Leu | Pro | Leu | Gly | Leu | Ala | Thr | Val | Met | Ser | Lys | His | Met |
|---|---|---|---|---|---|---|---|---|---|---|---|---|---|---|---|
| | | | 115 | | | | | 120 | | | | | 125 | | |

| Ser | Ile | Glu | Gln | Leu | Arg | Ala | Met | Leu | Pro | Thr | Asp | Arg | Gln | Gly | Tyr |
|---|---|---|---|---|---|---|---|---|---|---|---|---|---|---|---|
| | 130 | | | | | 135 | | | | | 140 | | | | |

| Ala | Glu | Val | Tyr | Ile | Asp | Pro | Leu | Asn | Glu | Thr | Met | Asp | Ile | Phe | Glu |
|---|---|---|---|---|---|---|---|---|---|---|---|---|---|---|---|
| 145 | | | | | 150 | | | | | 155 | | | | | 160 |

| Ile | Asn | Thr | Pro | Leu | Arg | Ile | Ala | His | Phe | Met | Ala | Gln | Ile | Leu | His |
|---|---|---|---|---|---|---|---|---|---|---|---|---|---|---|---|
| | | | | 165 | | | | | 170 | | | | | 175 | |

| Glu | Thr | Ala | Cys | Phe | Lys | Tyr | Thr | Glu | Glu | Leu | Ala | Ser | Gly | Lys | Ala |
|---|---|---|---|---|---|---|---|---|---|---|---|---|---|---|---|
| | | | 180 | | | | | 185 | | | | | 190 | | |

| Tyr | Glu | Gly | Arg | Ala | Asp | Leu | Gly | Asn | Thr | Arg | Pro | Gly | Asp | Gly | Pro |
|---|---|---|---|---|---|---|---|---|---|---|---|---|---|---|---|
| | | 195 | | | | | 200 | | | | | 205 | | | |

| Leu | Phe | Lys | Gly | Arg | Gly | Leu | Leu | Gln | Ile | Thr | Gly | Arg | Leu | Asn | Tyr |
|---|---|---|---|---|---|---|---|---|---|---|---|---|---|---|---|
| | 210 | | | | | 215 | | | | | 220 | | | | |

| Val | Lys | Cys | Gln | Val | Tyr | Leu | Arg | Glu | Lys | Leu | Lys | Asp | Pro | Thr | Phe |
|---|---|---|---|---|---|---|---|---|---|---|---|---|---|---|---|
| 225 | | | | | 230 | | | | | 235 | | | | | 240 |

| Asp | Ile | Thr | Ser | Ser | Val | Thr | Cys | Ala | Gln | Gln | Leu | Ser | Glu | Ser | Pro |
|---|---|---|---|---|---|---|---|---|---|---|---|---|---|---|---|
| | | | | 245 | | | | | 250 | | | | | 255 | |

| Leu | Leu | Ala | Ala | Leu | Ala | Ser | Gly | Tyr | Phe | Trp | Arg | Phe | Ile | Lys | Pro |
|---|---|---|---|---|---|---|---|---|---|---|---|---|---|---|---|
| | | | 260 | | | | | 265 | | | | | 270 | | |

| Lys | Leu | Asn | Glu | Thr | Ala | Asp | Lys | Asp | Ile | Tyr | Trp | Val | Ser | Val |
|---|---|---|---|---|---|---|---|---|---|---|---|---|---|---|
| | 275 | | | | | 280 | | | | | 285 | | | |

| Tyr | Val | Asn | Gly | Tyr | Ala | Lys | Gln | Ala | Asn | Pro | Tyr | Tyr | Pro | Asn | Arg |
|---|---|---|---|---|---|---|---|---|---|---|---|---|---|---|---|
| | 290 | | | | | 295 | | | | | 300 | | | | |

| Asp | Lys | Glu | Pro | Asn | His | Met | Lys | Glu | Arg | Val | Gln | Met | Leu | Ala | Val |
|---|---|---|---|---|---|---|---|---|---|---|---|---|---|---|---|
| 305 | | | | | 310 | | | | | 315 | | | | | 320 |

| Thr | Lys | Lys | Ala | His | Gly | Ile | Val | Lys | Gly | His | His | His | His | His | His |
|---|---|---|---|---|---|---|---|---|---|---|---|---|---|---|---|
| | | | | 325 | | | | | 330 | | | | | 335 | |

<210> SEQ ID NO 89
<211> LENGTH: 1011
<212> TYPE: DNA
<213> ORGANISM: unknown
<220> FEATURE:
<223> OTHER INFORMATION: OBPgpLYS derivative with additional His-tag

<400> SEQUENCE: 89
atgaaaaata gcgagaagaa tgcatcgata attatgtcga tacagagaac gctcgcttca    60

```
ctctcactct atggaggccg catcgacggc ctctttggag agaagtgtcg tggggctatc      120
atcttgatgc tgaataaggt ctatcctaat ttcagcacca acaaacttcc gagtaacaca      180
tatgaagcgg aatccgtgtt cacgtttctc cagactgctt tggctggtgt tggtctttat      240
accattacta ttgatggtaa atggggtggt acttctcaag gtgctattga cgccctcgtc      300
aagtcttacc gtcaaattac cgaagcggag cgagctgggt cgacgttgcc attaggtctt      360
gctactgtga tgtctaagca tatgtctatt gaacagttga gagcaatgct ccctaccgat      420
agacaaggat atgctgaagt ttatatcgat cctttaaatg acgcgatgga tatatttgaa      480
ataaatactc cattacgaat tgctcatttc atggcccaaa tcctccacga aacggcgtgt      540
tttaaatata ccgaagaact ggcgagcggt aaggcttatg agggtcgtgc tgatttaggt      600
aatactcgac caggtgatgg accactgttt aaaggtcgtg gattattaca aattaccggg      660
cgactgaatt atgtgaaatg ccaagtgtat ttgagagaga agttaaagga ccctactttc      720
gacattacgt cgtctgtaac ttgtgcccaa cagctctccg aaagtccact tcttgctgca      780
ttggcatcgg gctacttctg gagattcatc aaacctaaac tcaatgaaac ggctgataaa      840
gacgatatct attgggtttc tgtttatgtc aatggttacg ctaaacaagc gaatccttat      900
taccctaacc gggataagga acccaaccat atgaaagaac gtgtccaaat gcttgcagtg      960
acaaagaaag cacacggaat agttaagggt catcatcacc atcaccattg a              1011
```

<210> SEQ ID NO 90
<211> LENGTH: 72
<212> TYPE: DNA
<213> ORGANISM: unknown
<220> FEATURE:
<223> OTHER INFORMATION: antimicrobial peptide ascaphine

<400> SEQUENCE: 90

```
ggtatcaaag attggatcaa aggcgcagcg aaaaaactga tcaaaaccgt tgcctctcac      60
attgctaacc ag                                                         72
```

<210> SEQ ID NO 91
<211> LENGTH: 51
<212> TYPE: DNA
<213> ORGANISM: unknown
<220> FEATURE:
<223> OTHER INFORMATION: antimicrobial peptide apidaecine

<400> SEQUENCE: 91

```
gcgaaccgtc cggtctacat ccccaccgcca cgtccaccgc acccacgtct g              51
```

<210> SEQ ID NO 92
<211> LENGTH: 117
<212> TYPE: DNA
<213> ORGANISM: unknown
<220> FEATURE:
<223> OTHER INFORMATION: antimicrobial peptide Sarcotoxin IA

<400> SEQUENCE: 92

```
ggatggctca aaaagattgg caagaaaatc gagcgagtcg gtcagcatac gcgtgatgca      60
actatccagg gtttaggtat cgcacagcaa gcagctaatg tagcagctac tgctcgg        117
```

<210> SEQ ID NO 93
<211> LENGTH: 87
<212> TYPE: DNA
<213> ORGANISM: unknown
<220> FEATURE:
<223> OTHER INFORMATION: antimicrobial peptide SMAP-29

<400> SEQUENCE: 93
cgtggtctgc gtcgcctggg tcgcaaaatt gcgcacggcg tcaaaaaata cggcccgacc    60
gtgctgcgca ttatccgcat cgctggt    87

<210> SEQ ID NO 94
<211> LENGTH: 120
<212> TYPE: DNA
<213> ORGANISM: unknown
<220> FEATURE:
<223> OTHER INFORMATION: antimicrobial peptide Cecropin A (A.aegypti)

<400> SEQUENCE: 94
ggctggctga aaaaaattgg caaaaaaatc gaacgcgtgg gccagcacac gcgtgatgca    60
accatccagg gtctgggtat cccacagcag gcagctaacg tagccgcgac tgctcgtggt    120

<210> SEQ ID NO 95
<211> LENGTH: 39
<212> TYPE: DNA
<213> ORGANISM: unknown
<220> FEATURE:
<223> OTHER INFORMATION: antimicrobial peptide Alpha 4

<400> SEQUENCE: 95
ccgaaccgtg caaaacgtgt aatcaccacc ttccgtacc    39

<210> SEQ ID NO 96
<211> LENGTH: 15
<212> TYPE: DNA
<213> ORGANISM: unknown
<220> FEATURE:
<223> OTHER INFORMATION: synthetic peptide

<400> SEQUENCE: 96
ttcttcgtag caccg    15

<210> SEQ ID NO 97
<211> LENGTH: 54
<212> TYPE: DNA
<213> ORGANISM: unknown
<220> FEATURE:
<223> OTHER INFORMATION: antimicropial peptide Artilysin1

<400> SEQUENCE: 97
ggcttcttca tcccggcagt aatcctgccc tccatcgcat tcctgatcgt accg    54

<210> SEQ ID NO 98
<211> LENGTH: 75
<212> TYPE: DNA
<213> ORGANISM: unknown
<220> FEATURE:
<223> OTHER INFORMATION: antimicropial peptide Artilysin2

<400> SEQUENCE: 98
ggcaaaccgg gctggctgat caaaaaggca ctggtattca agaaactgat ccgtcgtccg    60
ctgaagagac tggca    75

<210> SEQ ID NO 99
<211> LENGTH: 57
<212> TYPE: DNA
<213> ORGANISM: unknown
<220> FEATURE:
<223> OTHER INFORMATION: antimicrobial peptide Parasin 1

```
<400> SEQUENCE: 99
aaaggccgtg gcaagcaggg aggcaaagta cgtgcaaaag caaagacccg ttcctca      57

<210> SEQ ID NO 100
<211> LENGTH: 75
<212> TYPE: DNA
<213> ORGANISM: unknown
<220> FEATURE:
<223> OTHER INFORMATION: antimicrobial peptide Lycotoxin

<400> SEQUENCE: 100
atctggctga ccgcactgaa attcctcggc aaacacgccg caaagaaact ggcaaaacag   60
caattatcca aactg                                                    75

<210> SEQ ID NO 101
<211> LENGTH: 984
<212> TYPE: DNA
<213> ORGANISM: unknown
<220> FEATURE:
<223> OTHER INFORMATION: OBPgpLYS

<400> SEQUENCE: 101
atgaaaaata gcgagaagaa tgcatcgata attatgtcga tacagagaac gctcgcttca   60
ctctcactct atggaggccg catcgacggc ctctttggag agaagtgtcg tggggctatc  120
atcttgatgc tgaataaggt ctatcctaat ttcagcacca caaacttcc gagtaacaca   180 tatgaagcgg aatccgtgtt cacgtttctc cagactgctt ggctggtgt tggtctttat   240 accattacta ttgatggtaa atggggtggt acttctcaag gtgctattga cgccctcgtc  300
aagtcttacc gtcaaattac cgaagcggag cgagctgggt cgacgttgcc attaggtctt  360
gctactgtga tgtctaagca tatgtctatt gaacagttga gagcaatgct ccctaccgat  420
agacaaggat atgctgaagt ttatatcgat cctttaaatg agacgatgga tatatttgaa  480
ataaatactc cattacgaat tgctcatttc atggcccaaa tcctccacga aacggcgtgt  540
tttaaatata ccgaagaact ggcgagcggt aaggcttatg agggtcgtgc tgatttaggt  600
aatactcgac caggtgatgg accactgttt aaaggtcgtg gattattaca aattaccggg  660
cgactgaatt atgtgaaatg ccaagtgtat ttgagagaga agttaaagga ccctactttc  720
gacattacgt cgtctgtaac ttgtgcccaa cagctctccg aaagtccact tcttgctgca  780
ttggcatcgg gctacttctg gagattcatc aaacctaaac tcaatgaaac ggctgataaa  840
gacgatatct attgggtttc tgtttatgtc aatggttacg ctaaacaagc gaatccttat  900
taccctaacc gggataagga acccaaccat atgaaagaac gtgtccaaat gcttgcagtg  960
acaaagaaag cacacggaat agtt                                        984

<210> SEQ ID NO 102
<211> LENGTH: 33
<212> TYPE: DNA
<213> ORGANISM: Artificial Sequence
<220> FEATURE:
<223> OTHER INFORMATION: forward primer

<400> SEQUENCE: 102
ggaatgggga gctcctccaa aaatagcgag aag                                33

<210> SEQ ID NO 103
<211> LENGTH: 24
<212> TYPE: DNA
<213> ORGANISM: Artificial Sequence
```

```
<220> FEATURE:
<223> OTHER INFORMATION: reverse primer

<400> SEQUENCE: 103
aactattccg tgtgctttct ttgt                                          24

<210> SEQ ID NO 104
<211> LENGTH: 48
<212> TYPE: DNA
<213> ORGANISM: Artificial Sequence
<220> FEATURE:
<223> OTHER INFORMATION: extended forward primer

<400> SEQUENCE: 104
atgggatcct tcttcgtagc accgggctcc tccaaaaata gcgagaag               48

<210> SEQ ID NO 105
<211> LENGTH: 39
<212> TYPE: DNA
<213> ORGANISM: Artificial sequence
<220> FEATURE:
<223> OTHER INFORMATION: forward primer alpha4

<400> SEQUENCE: 105
ttggaatggg gagcccgaac cgtgcaaaac gtgtaatca                          39

<210> SEQ ID NO 106
<211> LENGTH: 42
<212> TYPE: DNA
<213> ORGANISM: Artificial Sequence
<220> FEATURE:
<223> OTHER INFORMATION: reverse primer alpha4

<400> SEQUENCE: 106 tattttgga ggagccggta cggaaggtgg tgattacacg tt                      42

<210> SEQ ID NO 107
<211> LENGTH: 39
<212> TYPE: DNA
<213> ORGANISM: Artificial Sequence
<220> FEATURE:
<223> OTHER INFORMATION: forward primer artilys1

<400> SEQUENCE: 107
ttatgggctt cttcatcccg gcagtaatcc tgccctcca                          39

<210> SEQ ID NO 108
<211> LENGTH: 53
<212> TYPE: DNA
<213> ORGANISM: Artificial Sequence
<220> FEATURE:
<223> OTHER INFORMATION: reverse primer artilys1

<400> SEQUENCE: 108 tattttgga tctgccgccc ggtacgatca ggaatgcgat ggagggcagg att          53

<210> SEQ ID NO 109
<211> LENGTH: 47
<212> TYPE: DNA
<213> ORGANISM: Artificial Sequence
<220> FEATURE:
<223> OTHER INFORMATION: forward primer artilys2

<400> SEQUENCE: 109
ttatgggcaa accgggctgg ctgatcaaaa ggcactggta ttcaaga                47
```

<210> SEQ ID NO 110
<211> LENGTH: 64
<212> TYPE: DNA
<213> ORGANISM: Artificial Sequence
<220> FEATURE:
<223> OTHER INFORMATION: revers primer artilys2

<400> SEQUENCE: 110 tattttttgga tctgccgcct gccagtctct tcagcggacg acggatcagt ttcttgaata    60
ccag                                                                  64

<210> SEQ ID NO 111
<211> LENGTH: 48
<212> TYPE: DNA
<213> ORGANISM: Artificial Sequence
<220> FEATURE:
<223> OTHER INFORMATION: forward primer Parasin1

<400> SEQUENCE: 111
ttggaatggg gagcaaaggc cgtggcaagc agggaggcaa agtacgtg                  48

<210> SEQ ID NO 112
<211> LENGTH: 51
<212> TYPE: DNA
<213> ORGANISM: Artificial Sequence
<220> FEATURE:
<223> OTHER INFORMATION: reverse primer Parasin1

<400> SEQUENCE: 112 tattttttgga ggagcctgag gaacgggtct tgcttttgc acgtactttg c              51

<210> SEQ ID NO 113
<211> LENGTH: 55
<212> TYPE: DNA
<213> ORGANISM: Artificial Sequence
<220> FEATURE:
<223> OTHER INFORMATION: forward primer Lycotoxin

<400> SEQUENCE: 113
ggaatgggga gcatctggct gaccgcactg aaattcctcg gcaaacacgc cgcaa          55

<210> SEQ ID NO 114
<211> LENGTH: 60
<212> TYPE: DNA
<213> ORGANISM: Artificial Sequence
<220> FEATURE:
<223> OTHER INFORMATION: reverse primer Lycotoxin

<400> SEQUENCE: 114 tattttttgga ggagcccagt ttggataatt gctgttttgc cagtttctttt gcggcgtgtt  60

<210> SEQ ID NO 115
<211> LENGTH: 339
<212> TYPE: PRT
<213> ORGANISM: unknown
<220> FEATURE:
<223> OTHER INFORMATION: PKOBPgpLYS derivative

<400> SEQUENCE: 115

Met Gly Ser Lys Arg Lys Lys Arg Lys Lys Arg Lys Lys Asn Ser Glu
1               5                   10                  15

Lys Asn Ala Ser Ile Ile Met Ser Ile Gln Arg Thr Leu Ala Ser Leu
            20                  25                  30

Ser Leu Tyr Gly Gly Arg Ile Asp Gly Leu Phe Gly Glu Lys Cys Arg

```
                35                  40                  45
Gly Ala Ile Ile Leu Met Leu Asn Lys Val Tyr Pro Asn Phe Ser Thr
 50                  55                  60
Asn Lys Leu Pro Ser Asn Thr Tyr Glu Ala Glu Ser Val Phe Thr Phe
 65                  70                  75                  80
Leu Gln Thr Ala Leu Ala Gly Val Gly Leu Tyr Thr Ile Thr Ile Asp
                 85                  90                  95
Gly Lys Trp Gly Gly Thr Ser Gln Gly Ala Ile Asp Ala Leu Val Lys
            100                 105                 110
Ser Tyr Arg Gln Ile Thr Glu Ala Glu Arg Ala Gly Ser Thr Leu Pro
            115                 120                 125
Leu Gly Leu Ala Thr Val Met Ser Lys His Met Ser Ile Glu Gln Leu
130                 135                 140
Arg Ala Met Leu Pro Thr Asp Arg Gln Gly Tyr Ala Glu Val Tyr Ile
145                 150                 155                 160
Asp Pro Leu Asn Glu Thr Met Asp Ile Phe Glu Ile Asn Thr Pro Leu
                165                 170                 175
Arg Ile Ala His Phe Met Ala Gln Ile Leu His Glu Thr Ala Cys Phe
            180                 185                 190
Lys Tyr Thr Glu Glu Leu Ala Ser Gly Lys Ala Tyr Glu Gly Arg Ala
            195                 200                 205
Asp Leu Gly Asn Thr Arg Pro Gly Asp Gly Pro Leu Phe Lys Gly Arg
210                 215                 220
Gly Leu Leu Gln Ile Thr Gly Arg Leu Asn Tyr Val Lys Cys Gln Val
225                 230                 235                 240
Tyr Leu Arg Glu Lys Leu Lys Asp Pro Thr Phe Asp Ile Thr Ser Ser
                245                 250                 255
Val Thr Cys Ala Gln Gln Leu Ser Glu Ser Pro Leu Leu Ala Ala Leu
            260                 265                 270
Ala Ser Gly Tyr Phe Trp Arg Phe Ile Lys Pro Lys Leu Asn Glu Thr
            275                 280                 285
Ala Asp Lys Asp Asp Ile Tyr Trp Val Ser Val Tyr Val Asn Gly Tyr
290                 295                 300
Ala Lys Gln Ala Asn Pro Tyr Tyr Pro Asn Arg Asp Lys Glu Pro Asn
305                 310                 315                 320
His Met Lys Glu Arg Val Gln Met Leu Ala Val Thr Lys Lys Ala His
                325                 330                 335
Gly Ile Val

<210> SEQ ID NO 116
<211> LENGTH: 347
<212> TYPE: PRT
<213> ORGANISM: unknown
<220> FEATURE:
<223> OTHER INFORMATION: PKOBPgpLYS derivative with additional His-tag

<400> SEQUENCE: 116

Met Gly Ser Lys Arg Lys Lys Arg Lys Arg Lys Lys Asn Ser Glu
 1               5                  10                  15
Lys Asn Ala Ser Ile Ile Met Ser Ile Gln Arg Thr Leu Ala Ser Leu
                 20                  25                  30
Ser Leu Tyr Gly Gly Arg Ile Asp Gly Leu Phe Gly Glu Lys Cys Arg
             35                  40                  45
Gly Ala Ile Ile Leu Met Leu Asn Lys Val Tyr Pro Asn Phe Ser Thr
 50                  55                  60
```

```
Asn Lys Leu Pro Ser Asn Thr Tyr Glu Ala Glu Ser Val Phe Thr Phe
 65                  70                  75                  80

Leu Gln Thr Ala Leu Ala Gly Val Gly Leu Tyr Thr Ile Thr Ile Asp
                 85                  90                  95

Gly Lys Trp Gly Gly Thr Ser Gln Gly Ala Ile Asp Ala Leu Val Lys
            100                 105                 110

Ser Tyr Arg Gln Ile Thr Glu Ala Glu Arg Ala Gly Ser Thr Leu Pro
        115                 120                 125

Leu Gly Leu Ala Thr Val Met Ser Lys His Met Ser Ile Glu Gln Leu
    130                 135                 140

Arg Ala Met Leu Pro Thr Asp Arg Gln Gly Tyr Ala Glu Val Tyr Ile
145                 150                 155                 160

Asp Pro Leu Asn Glu Thr Met Asp Ile Phe Glu Ile Asn Thr Pro Leu
                165                 170                 175

Arg Ile Ala His Phe Met Ala Gln Ile Leu His Glu Thr Ala Cys Phe
                180                 185                 190

Lys Tyr Thr Glu Glu Leu Ala Ser Gly Lys Ala Tyr Glu Gly Arg Ala
        195                 200                 205

Asp Leu Gly Asn Thr Arg Pro Gly Asp Gly Pro Leu Phe Lys Gly Arg
    210                 215                 220

Gly Leu Leu Gln Ile Thr Gly Arg Leu Asn Tyr Val Lys Cys Gln Val
225                 230                 235                 240

Tyr Leu Arg Glu Lys Leu Lys Asp Pro Thr Phe Asp Ile Thr Ser Ser
                245                 250                 255

Val Thr Cys Ala Gln Gln Leu Ser Glu Ser Pro Leu Leu Ala Ala Leu
                260                 265                 270

Ala Ser Gly Tyr Phe Trp Arg Phe Ile Lys Pro Lys Leu Asn Glu Thr
            275                 280                 285

Ala Asp Lys Asp Asp Ile Tyr Trp Val Ser Val Tyr Val Asn Gly Tyr
        290                 295                 300

Ala Lys Gln Ala Asn Pro Tyr Tyr Pro Asn Arg Asp Lys Glu Pro Asn
305                 310                 315                 320

His Met Lys Glu Arg Val Gln Met Leu Ala Val Thr Lys Lys Ala His
                325                 330                 335

Gly Ile Val Lys Gly His His His His His
            340                 345

<210> SEQ ID NO 117
<211> LENGTH: 18
<212> TYPE: PRT
<213> ORGANISM: unknown
<220> FEATURE:
<223> OTHER INFORMATION: antimicrobial peptide Ranalexin

<400> SEQUENCE: 117

Phe Leu Gly Gly Leu Ile Val Pro Ala Met Ile Cys Ala Val Thr Lys
 1               5                  10                  15

Lys Cys

<210> SEQ ID NO 118
<211> LENGTH: 27
<212> TYPE: PRT
<213> ORGANISM: unknown
<220> FEATURE:
<223> OTHER INFORMATION: peptide stretch WLBU2 variant

<400> SEQUENCE: 118
```

```
Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 119
<211> LENGTH: 26
<212> TYPE: PRT
<213> ORGANISM: unknown
<220> FEATURE:
<223> OTHER INFORMATION: antimicrobial peptide Melittin

<400> SEQUENCE: 119

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```